(12) United States Patent
Dow et al.

(10) Patent No.: US 10,206,983 B2
(45) Date of Patent: Feb. 19, 2019

(54) METHODS AND COMPOSITIONS FOR ENHANCING AN IMMUNE RESPONSE, BLOCKING MONOCYTE MIGRATION, AMPLIFYING VACCINE IMMUNITY AND INHIBITING TUMOR GROWTH AND METASTASIS

(71) Applicant: Colorado State University Research Foundation, Fort Collins, CO (US)

(72) Inventors: Steven W. Dow, Littleton, CO (US); Daniel P. Regan, Fort Collins, CO (US); Amanda Guth, Fort Collins, CO (US); Leah Mitchell, San Diego, CA (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

(21) Appl. No.: 15/400,645

(22) Filed: Jan. 6, 2017

(65) Prior Publication Data

US 2017/0348400 A1    Dec. 7, 2017

Related U.S. Application Data

(62) Division of application No. 14/609,146, filed on Jan. 29, 2015, now Pat. No. 9,539,314, which is a division of application No. 14/195,688, filed on Mar. 3, 2014, now Pat. No. 8,975,290.

(60) Provisional application No. 61/771,738, filed on Mar. 1, 2013, provisional application No. 61/771,744, filed on Mar. 1, 2013.

(51) Int. Cl.
| | |
|---|---|
| A61K 31/405 | (2006.01) |
| A61K 39/00 | (2006.01) |
| A61K 39/39 | (2006.01) |
| A61K 45/06 | (2006.01) |
| A61K 31/404 | (2006.01) |
| A61K 31/4178 | (2006.01) |
| A61K 31/437 | (2006.01) |

(52) U.S. Cl.
CPC ........ *A61K 39/0005* (2013.01); *A61K 31/404* (2013.01); *A61K 31/4178* (2013.01); *A61K 31/437* (2013.01); *A61K 39/39* (2013.01); *A61K 45/06* (2013.01); *A61K 2039/55511* (2013.01)

(58) Field of Classification Search
CPC .................................................. C07D 209/88
USPC ....................................................... 514/411
See application file for complete search history.

(56) References Cited

U.S. PATENT DOCUMENTS

| | | | |
|---|---|---|---|
| 8,168,758 B2 * | 5/2012 | Tamburini | ........... A61K 39/395 |
| | | | 530/387.1 |
| 8,710,191 B2 | 4/2014 | Gladue et al. | |
| 8,759,014 B2 | 6/2014 | Kammula | |
| 8,975,290 B2 | 3/2015 | Dow et al. | |
| 9,320,735 B2 | 4/2016 | Dow et al. | |
| 9,539,314 B2 | 1/2017 | Dow et al. | |
| 2002/0042370 A1 | 4/2002 | Hancock | |
| 2007/0021466 A1 | 1/2007 | Ungashe et al. | |
| 2007/0025960 A1 | 2/2007 | Pauza et al. | |
| 2008/0194494 A1 | 8/2008 | Martinez et al. | |
| 2009/0196887 A1 | 8/2009 | Morita et al. | |
| 2009/0253792 A1 * | 10/2009 | Mickle | ................. A61K 31/195 |
| | | | 514/561 |
| 2010/0247623 A1 | 9/2010 | Bystryn | |
| 2012/0156280 A1 | 6/2012 | Dow et al. | |
| 2012/0189664 A1 | 7/2012 | Yu | |
| 2014/0248315 A1 | 9/2014 | Dow et al. | |
| 2016/0287686 A1 | 10/2016 | Dow et al. | |

FOREIGN PATENT DOCUMENTS

| | | |
|---|---|---|
| CN | 101612400 A | 12/2009 |
| WO | WO 2005/021708 A2 | 3/2005 |
| WO | WO 2007/124274 A1 | 11/2007 |
| WO | WO 2011/053789 A2 | 5/2011 |
| WO | WO 2011/116299 A2 | 9/2011 |
| WO | WO 2012/030234 A1 | 3/2012 |
| WO | WO 2012/054807 A2 | 4/2012 |
| WO | WO 2012/068531 A2 | 5/2012 |
| WO | WO 2012/094703 A1 | 7/2012 |

(Continued)

OTHER PUBLICATIONS

Extended European Search Report for European Application No. 11757071.3, dated Jul. 8, 2013, 11 pages.
PCT/US2011/029022, International Search Report and Written Opinion, dated Dec. 27, 2011, 8 pages.
PCT/US2011/029022, International Preliminary Report on Patentability, dated Sep. 18, 2012, 6 pages.
PCT/US2014/020018, International Search Report and Written Opinion, dated Aug. 13, 2014, 14 pages.
PCT/US2014/020018, International Preliminary Report on Patentability, dated Sep. 1, 2015, 7 pages.

(Continued)

*Primary Examiner* — Rei Tsang Shiao
(74) *Attorney, Agent, or Firm* — Polsinelli PC

(57) ABSTRACT

Provided are methods of enhancing an immune response and methods for reducing the recruitment of monocytes to a lymph node by administering to an individual an angiotensin II receptor blocker or a compound of Formula (I) in conjunction with an antigen. The invention also provides relate methods for amplifying vaccine immunity by administering to an individual an angiotensin II receptor blocker or a compound of Formula (I) in conjunction with a vaccine. The invention also provides related methods of inhibiting tumor growth and metastasis by administering to an individual with cancer an angiotensin II receptor blocker or a compound of Formula (I) in conjunction with an anti-tumor preparation. In addition, related compositions comprising an ARB or a compound of Formula (I) and an antigen, vaccine, or anti-tumor preparation are provided.

13 Claims, 17 Drawing Sheets

(56) References Cited

FOREIGN PATENT DOCUMENTS

| WO | WO 2014/134621 A2 | 9/2014 |
|---|---|---|
| WO | WO 2016/161309 A1 | 10/2016 |

OTHER PUBLICATIONS

PCT/US2016/025596, International Search Report and Written Opinion, dated Jul. 12, 2016, 9 pages.
Affolter, V. et al., "Canine Cutaneous and Systemic Histiocytosis", *The American Journal of Dermatopathology* (2000), 22(1): 40-48.
Affolter, V. et al., "Localized and Disseminated histiocytic Sarcoma of Dendritic Cell Origin in Dogs", *Vet Pathol* (2002), 39:74-83.
Aguzzi, A., et al., "Pathogenesis of Prion Diseases: Current Status and Future Outlook", *Nature Reviews, Microbiology* (2006),4:765-775.
Aguzzi, A., et al., "Immune System and Peripheral Nerves in Propagation of Prions to CNS" *British Medical Bulletin* (2003), 66:141-159.
Almand, B., et al., "Increased Production of Immature Myeloid Cells in Cancer Patients: A Mechanism of Immunosuppression in Cancer", *J Immunol* (2001), 166:678-689.
Alves-Rosa, F., et al., "Treatment with Liposome-Encapsulated Clodronate as a New Strategic Approach in the Management of Immune Thrombocytopenic Purpura in a Mouse Model", *Blood*. (Oct. 15, 2000), 96:2834-2840.
Arbel, M., et al., "Generation of Antibodies Against Prion Protein in Wild-Type Mice Via Helix 1 Peptide Immunization", *Journal of Neuroimmunology* (2003), 144:38-45.
Banzhoff, A., et al., "A New MF59-Adjuvanted Influenza Vaccine Enhances the Immune Response in the Elderly with Chronic Diseases: Results from an Immunogenicity Meta-Analysis", *Gerontology* (2003), 49:177-184.
Bhangoo, et al., "Delayed Functional Expression of Neuronal Chemokine Receptors Following Focal Nerve Demyelination in the Rat: a Mechanism for the Development of Chronic Sensitization of Peripheral Nociceptors", *Molecular Pain*, BioMed Central Ltd., (2007), 3:38, pp. 1-20.
Bird, R., et al., "An Allogeneic Hybrid-Cell Fusion Vaccine Against Canine Mammary Cancer", *Veterinary Immunology and Immunopathology* (2008), 128: 289-304.
Brando, C., et al., "Murine Immune Responses to Liver-Stage Antigen 1 Protein FMP011, a Malaria Vaccine Candidate, Delivered with Adjuvant AS01B or AS02A", *Infection and Immunity*, Feb. 2007, p. 838-845.
Brodmerkel et al., "Imaging musculoskeletal infection with (111) indium labeled anti-E-selectin monoclonal antibody 1.2 B6 as an alternative to (111) indium labeled leukocyte scintigraphy." Arthritis and Rheumatism, 50(9):5263, vol. 5, No. 9 (2004).
Bronte, V., "Myeloid-derived suppressor cells in inflammation: Uncovering cell subsets with enhanced immunosuppressive functions," Eur. J. Immunol. (2009), 39:2670-2672.
Bucksky, P., et al., "Malignant Histiocytic Disorders in Children, Clinical and Therapeutic Approaches with a Nostalgic Discussion," Hematol Oncol Clin North Am (Apr. 1998), 12:465-471.
Caglar, K. et al., "Effect of monophosphoryl lipid A on antibody response to diphtheria toxin and its subunits," APMIS (2005), 113:256-63.
Caughey, B., et al., "Prions and their partners in crime", *Nature* (Oct. 2006), 443:803-810.
Cecchini, M., et al., "Effect of Bisphosphonates on Proliferation and Viability of Mouse Bone Marrow-Derived Macrophages", *Journal of Bone and Mineral Research* (1987),2(2):135-142.
"Cellular Immunotherapy for Acute Myeloid Leukemia using Dendritic Cells Pulsed with WT1 Peptide and Zoledronate", International Clinical Trials Registry Platform, Jul. 1, 2007.
Clark, R., et al., "Synthesis and Antihypertensive Activity of 4'-Substituted Spiro[4H-3,1-benzoxazine-4,4'-piperidin]-2(1H)-ones", *J. Med. Chem.* (1983), 26:657-661.

Clezardin, P., et al., "In Vitro and In Vivo Antitumor Effects of Bisphosphonates" *Current Medicinal Chemistry* (2003), 10:173-180.
Condamine, T., et al., "Molecular mechanisms regulating myeloid-derived suppressor cell differentiation and function", *Trends Immunol.* (2011), 32(1):19-25.
Desai, M., et al., "Immune response with biodegradable nanospheres and alum: studies in rabbits using staphylococcal enterotoxin B-toxoid", *J. Microencapsulation* (2000), 17(2):215-225.
DeSanto, C., et al., "Nitroaspirin corrects immune dysfunction in tumor-bearing hosts and promotes tumor eradication by cancer vaccination", *National Academy of Sciences of the USA* (Mar. 15, 2005),102(11):4185-4190.
de Souza Matos, D., et al., "Immunostimulatory effects of polar glycopeptidolipids of *Mycobacterium chelonae* for inactivated rabies vaccine", *Vaccine* (2000), 18:2125-2131.
Diaz-Montero, C.M., et al., "Increased circulating myeloid-derived suppressor cells correlate with clinical cancer stage, metastatic tumor burden, and doxorubicin-cyclophosphamide chemotherapy", *Cancer Immunol Immunother*. (Jan. 2009), 58(1):49-59.
Dow, S., et al., "In Vivo Tumor Transfection with Superantigen plus Cytokine Genes Induces Tumor Regression and Prolongs Survival in Dogs with Malignant Melanoma", *J. Clin. Invest.* vol. 101, No. 11, Jun. 1998, 2406-2414.
Eldridge, J., et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies", *Infection and Immunity* (Sep. 1991), 59(9):2978-2986.
European Patent Application No. EP 14756530.3, Partial European Search Report dated Sep. 27, 2016, 10 pages.
European Patent Application No. EP 14756530.3, Extended European Search Report dated Feb. 23, 2017, 17 pages.
Enari, M., et al., "Scrapie prion protein accumulation by scrapie-infected neuroblastoma cells abrogated by exposure to a prion protein antibody", *Proc. Natl. Acad. Sci.* (2001), 98(16):9295-9299.
Flick-Smith, H., et al., "Mucosal or Parenteral Administration of Microsphere-Associated Bacillus anthracis Protective Antigen Protects against Anthrax Infection in Mice", *Infection and Immunity* (Apr. 2002), 70(4):2022-2028.
Fridlender et al., "CCL2 Blockade Augments Cancer Immunotherapy," Cancer Research (Jan. 2010), 70(1):109-118.
Frith, J. et al., "The Molecular Mechanism of Action of the Antiresorptive and Antiinflammatory Drug Clodronate," Arthritis & Rheumatism (Sep. 2001), 44(9):2201-2210.
Frith, J. et al., "Clodronate and Liposome-Encapsulated Clodronate Are Metabolized to a Toxic ATP Analog, Adenosine 5'-($\beta,\gamma$-Dichloromethylene) Triphosphate, by Mammalian Cells In Vitro," Journal of Bone and Mineral Research (1997), 12(9):1358-1367.
Gabrilovich, D.I. et al, "Myeloid-derived suppressor cells as regulators of the immune system", *Nat Rev Immunol* (Mar. 2009), 9(3):162-174.
Gabrilovich, D.I. et al, "Coordinated Regulation of Myeloid Cells by Tumours", *Nature Reviews, Immunology*, Apr. 2012, pp. 253-268, vol. 12, Macmillan Publishers Limited.
Garin, et al., "Chemokines as Targets for Therapy", Experimental Cell Research 317, ScienceDirect (2011), pp. 602-612.
Gazzaniga, S., et al., "Targeting tumor-associated macrophages and inhibition of MCP-1 reduce angiogenesis and tumor growth in a human melanoma xenograft", *Journal of Investigative Dermatology* (2007), 127:2031-2041.
Gilch, S., et al., "Polyclonal anti-PrP auto-antibodies induced with dimeric PrP interfere efficiently with PrPSc propagation in prion-infected cells", *J. Biol. Chem.* (2003), 278:18524-18531.
Guth, A.M., et al., "Comparison of cancer stem cell antigen expression by tumor cell lines and by tumor biopsies from dogs with melanoma and osteosarcoma." Veterinary Immunology and Immunopathology (2014); 161.(0): 132-140, 18 pages.
Green, J., "Antitumor Effects of Bisphosphonates", *Cancer* Supplement (Feb. 2003), 97(3):840-847.

(56) References Cited

OTHER PUBLICATIONS

Griffiths, G., et al., "Liposomally-encapsulated ricin toxoid vaccine delivered intratracheally elicits a good immune response and protects against a lethal pulmonary dose of ricin toxin", *Vaccine* (1997) 15:1933-1939.
Hanan, E., et al., "Immunomodulation of the Human Prion Peptide 106-126 Aggregation", *Biochemical and Biophysical Research Communications* (2001), 280:115-120.
Hanan, E., et al., "Antiaggregating Antibody Raised Against Human PrP 106-126 Recognizes Pathological and Normal Isoforms of the Whole Prion Protein", *Cellular and Molecular Neurobiology* (2001), 21:693-703.
Hedlund, J., et al., "Negligible adjuvant effect for antibody responses and frequent adverse events associated with IL-12 treatment in humans vaccinagted with pneumococcal polysaccharide", *Vaccine* (2002), 20:164-169.
Higgins, D., et al., "MF59 adjuvant enhances the immunogenicity of influenza vaccine in both young and old mice", *Vaccine* (1996), 14(6):478-484.
Higgins, P., et al., "Small molecule CCR2 antagonists" *Chemokine Biology—Basic Research and Clinical Application* (2007), vol. II., pp. 115-123.
Howarth, D., et al., "Langerhans Cell Histiocytosis", *Cancer* (May 15, 1999), 85:2278-90.
Hughes, R.O. et al., "Discovery of ((1S,3R)-1-isopropyl-3-((3S,4S)-3-methoxy-tetrahydro-2H-pyran-4-ylamino)cyclopentyl)(4-(5-(trifluoromethyl)pyridazin-3-y1)piperazin-1-yl)methanone, PF-4254196, a CCR2 antagonist with an improved cardiovascular profile", Bioorganic & Medicinal Chemistry Letters (2011), 21: 2626-2630.
Hughes, D., et al., "Bisphosphonates Promote Apoptosis in Murine Osteoclasts In Vitro and In Vivo", *Journal of Bone and Mineral Research* (1995), vol. 10, No. 10, pp. 1478-1487.
Jaganathan, K.S., et al., "Strong systemic and mucosal immune responses tosurface-modified PLGA microspheres containing recombinant Hepatitis B antigen administered intranasally", *Vaccine* (2006), 24:4201-4211.
Jakubzick, C., et al., "Blood monocyte subsets differentially give rise to CD103+ and CD103− pulmonary dendritic cell populations", *J Immunol* (2008), 180(2):3019-3027.
Jakubzick, C., et al., "Optimization of methods to study pulmonary dendritic cell migration reveals distinct capacities of DC subsets to acquire soluble versus particulate antigen". *J Immunol Methods.* (2008), 337:121-131.
Jordan, M., et al., "Liposomal clodronate as a novel agent for treating autoimmune hemolytic anemia in a mouse model", *Blood.* (Jan. 2003), 101(2):594-601.
Kende, M., et al., "Enhancement of intranasal vaccination in mice with deglycosylated chain A ricin by LTR72, a novel mucosal adjuvant", *Vaccine* (2006), 24:2213-2221.
Kenney, R., et al., "Protective Immunity Using Recombinannt Human IL-12 and Alum as Adjuvants in a Primate Model of Cutaneous Leishmaniasis", *The Journal of Immunology* (1999), 163:4481-4488.
Kitawaki, T. et al., "A Phase I/IIa clinical trial of immunotherapy for Elderly Patients with Acute Myeloid Leukaemia Using Dendritic Cells co-Pulsed with WT1 Peptide and Zoledronate," Br. J. Haematology (2011), 153(6):796-799.
Koller, M., et al., "Induction of antibodies against murine full-length prion protein in wild-type mice", *Journal of Neuroimmunology* (2002), 132:113-116.
Kosugi, M., et al., "Effect of angiotensin II type 1 receptor antagonist on tumor growth and angiogenesis in a xenograft model of human bladder cancer." Human Cell (2007); 20(1): 1-9.
Kusmartsev, S., et al., "Role of immature myeloid cells in mechanisms of immune evasion in cancer", *Cancer Immunol Immunother.* (2006), 55(3): 237-245.
Kusmartsev, S., et al., "Reversal of myeloid cell-mediated immunosuppression in patients with metastatic renal cell carcinoma", *Clin Cancer Res* (Dec. 15, 2008), 14(24):8270-8278.
Langermans, J., et al., "Effect of adjuvant on reactogenicity and long-term immunogenicity of the malaria Vaccine ICC-1132 in macaques", *Vaccine* (2005) 23:4935-4943.
Lauren, L., et al., "Pharmacokinetics of Clodronate after Single Intravenous, Intramuscular and Subcutaneous Injections in Rats", *Pharmacology & Toxicology* (1991), vol. 69, 365-368.
Lehenkari, P., et al., "Further Insight into Mechanism of Action of Clodronate: Inhibition of Mitochondrial ADP/ATP Translocase by a Nonhydrolyzable, Adenine-Containing Metabolite", *Mol. Pharmacol.* (2002), 62(5):1255-1262.
Levesque, P., et al., "Association Between Immunogenicity and Adsorption of a Recombinant *Streptococcus pneumoniae* Vaccine Antigen by an Aluminum Adjuvant", *Human Vaccines* (2006), 2(2):74-77.
Lin, J., "Bisphosphonates: A review of Their Pharmacokinetic Properties", *Bone* (Feb. 1996), vol. 18, No. 2, pp. 75-85.
Lin, K.L. et al., "CCR2-Antagonist Prophylaxis Reduces Pulmonary Immune Pathology and Markedly Improves Survival during Influenza Infection", The Journal of Immunology (2011), 186: 508-515.
Loike, J., et al., "A Fluorescense Quenching Technique Using Trypan Blue to Differentiate between Attached and Ingested Glutaraldehyde-Fixed Red Blood Cells in Phagocytosing Murine Macrophages", *Journal of Immunological Methods* (1983), 57:373-379.
Maeda, A., et al., "Immunosuppressive effect of angiotensin receptor blocker on stimulation of mice CTLs by angiotensin II." International Immunopharmacology (2009); 9(10): 1183-1188.
Mantovani, A., et al., "Macrophages, innate immunity and cancer: balance, tolerance, and diversity", *Current Opinion in Immunology* (2010), 22:231-237.
Mantovani, A., "Molecular pathways linking inflammation and cancer", *Curr. Mol. Med.* (2010), 10(4):369-373.
Martin, J., "Development of an Adjuvant to Enhance the Immune Response to Influenza Vaccine in the Elderly", *Biologicals* (1997), 25:209-213.
Mathes, M., et al., "Evaluation of liposomal clodronate in experimental spontaneous autoimmune hemolytic anemia in dogs", *Experimental Hermatology* (2006), 34:1393-1402.
Melani, C. et al., "Amino-Biphosphonate-Mediated MMP-9 Inhibition Breaks the Tumor-Bone Marrow Axis Responsible for Myeloid-Derived Suppressor Cell Expansion and Macrophase Infiltration in Tumor Stroma," Cancer Research, (2007), 67(23):11438-11446.
Mendez, S., et al., "Coinjection with CpG-Containing Immunostimulatory Oligodeoxynucleotides Reduces the Pathogencity of a Live Vaccine against Cutaneous Leishmaniasis but Maintains Its Potency and Durability", *Infection and Immunity*, Sep. 2003, p. 5121-5129.
Miyazaki, A., et al., "Anti-inflammatory effect of angiotensin type 1 receptor antagonist on endotoxin-induced uveitis in rats." Graefe's Archive for Clinical and Experimental Opthalmology (2008); 246(5): 747-757.
Mirzadegan, T., et al., "Identification of the binding site for a novel class of CCR2b chemokine receptor antagonists: binding to a common chemokine receptor motif within the helical bundle", *The Journal of Biological Chemistry* (Aug. 18, 2000), 275(33):25562-25571.
Mitchell, Leah A., et al., "Suppression of Vaccine Immunity by Inflammatory Monocytes", *The Journal of Immunology*, Nov. 7, 2012, pp. 1-10, J Immunol published online.
Mitchell, Leah A., et al., "Optimized Dosing of CCR2 Antagonist for Amplification of Vaccine Immunity", *International Immunopharmacolog* (2013), vol. 15, pp. 357-363, Elsevier.
Monkkonen, J., et al., "The Effects of Liposome-Encapsulated and Free Clodronate on the Growth of Macrophage-like Cells In Vitro: The Role of Calcium and Iron", *Calcif Tissue Int* (1993), 53:139-146.
Monkkonen, J., et al., "Growth Inhibition of Macrophage-Like and Other Cell Types by Liposome-Encapsulated, Calcium-Bound, and Free Bisphosphonates In Vitro", *Journal of Drug Targeting* (1994) vol. 2, No. 4, pp. 299-308.
Moore, K., et al., "Intracellular Infection by Leishmania donovani Inhibits Macrophage Apoptosis", *Journal of Immunology* (1994), 152:2930-2937.

(56) References Cited

OTHER PUBLICATIONS

Moore, P., et al., "Canine Hemophagocytic Histiocytic Sarcoma: A Proliferative Disorder of CD11d+ Macrophages", *Vet Pathol.* (2006), 43(5):632-645.

Mullen, G., et al., "Enhancement of functional antibody responses to AMA1-C1/Alhydrogel®, a Plasmodium falciparum malaria vaccine, with CpG oligodeoxynucleotide", *Vaccine* (2006), 24:2497-2505.

Nakano, H., et al., "Blood-derived inflammatory dendritic cells in lymph nodes stimulate acute T helper type 1 immune responses", *Nature Immunology* (Apr. 2009), 10(4):394-402.

Noguchi, R., et al., "Synergistic inhibitory effect of gemcitabine and angiotensin type-1 receptor blocker, losartan, on murine pancreatic tumor growth via anti-angiogenic activities." Oncology Reports (2009); 22.2: 355-360.

Ostrand-Rosenberg et al., "Antagonists of tumor-specific immunity: tumor-induced immune suppression and host genes that co-opt the anti-tumor immune response", *Breast Disease* (2004), 20:127-135, IOS Press.

Ostrand-Rosenberg et al., "Myeloid-derived suppressor cells: linking inflammation and cancer", *J Immunol* (2009), 182:4499-4506.

Palese, P., "Making Better Influenza Virus Vaccines?", *Emerging Infectious Diseases* (2006), 12(1):61-65.

Peng, M., et al., "Novel vaccines for the treatment of chronic HBV infection based on mycobacterial heat shock protein 70", *Vaccine* (2006), 24:887-896.

Peretz, D., et al., "Antibodies inhibit prion propagation and clear cell cultures of prion infectivity", *Nature* (Aug. 16, 2001), 412:739-743.

Petrik, M., et al., "Aluminum Adjuvant Linked to Gulf War Illness Induces Motor Neuron Death in Mice", *NeuroMolecular Medicine* (2007), 9(1):83-100.

Pimenta, F., et al., "Intranasal Immunization with the Cholera Toxin B Subunit-Pneumococcal Surface Antigen A Fusion Protein Induces Protection against Colonization with *Streptococcus pneumoniae* and Has Negligible Impact on the Nasopharyngeal and Oral Microbiota of Mice", *Infection and Immunity*(Aug. 2006), 74(8):4939-4944.

Pollard, J.W., "Tumour-educated macrophages promote tumour progression and metastasis", *Nature Reviews Cancer* (Jan. 2004) 4:71-78.

Polymenidou, M., et al., "Humoral immune response to native eukaryotic prion protein correlates with anti-prion protection", *Proc. Natl. Acad. Sci.* (Oct. 5, 2004), 101(Suppl. 2):14670-14676.

Qian, Bin-Zhi, et al., "CCL2 recruits inflammatory monocytes to facilitate breast-tumour metastasis", *Nature.* (2011), 475(7355):222-225.

Qin, W., et al., "CpG ODN Enhances Immunization Effects of Hepatitis B Vaccine in Aged Mice", *Cellular & Molecular Immunology* (2004), 1(2):148-152.

Randolph, G.J., et al., "A soluble gradient of endogenous monocyte chemoattractant protein-1 promotes the transendothelial migration of monocytes in vitro", *The Journal of Immunology* (1995), 155:3610-3618.

Randolph, G.J., et al., "Differentiation of phagocytic monocytes into lymph node dendritic cells in vivo", *Immunity* (Dec. 1999), 11:753-761.

Roelofs, A. J. et al., "Molecular Mechanisms of Action of Bisphosphonates: Current Status," *Clin. Cancer Res.* (Oct. 15, 2006), 12(20 Pt. 2)::62225-6230s.

Rogers, M., et al., "Cellular and Molecular Mechanisms of Action of Bisphosphonates", *Cancer* Supplemental (2000), 88(12):2961-2978.

Rosado-Vallado, M., et al., "Aluminium phosphate potentiates the efficacy of DNA vaccines against Leishmania mexicana", *Vaccine* (2005), 23:5372-5379.

Rosset, M., et al., "Breaking Immune Tolerance to the Prion Protein Using Prion Protein Peptides Plus Oligodeoxynucleotide-CpG in Mice", *The Journal of Immunology* (2004), 172:5168-5174.

Sabirov, A., et al., "Intranasal vaccination of neonatal mice with polysaccharide conjugate vaccine for protection against pneumococcal otitis media", *Vaccine* (2006), 24:5584-5592.

Sagawa, K., et al., "Angiotensin Receptor Blockers Suppress Antigen-Specific T Cell Responses and Ameliorate Collagen-Induced Arthritis in Mice." Arthritis & Rheumatism (2005); 52(6): 1920-1928.

Schwarz, A., et al., "Immunisation with a synthetic prion protein-derived peptide prolongs survival times of mice orally exposed to the scrapie agent", *Neuroscience Letters* (2003), 350:187-189.

Segura-Velazquez, R., et al., "A novel synthetic adjuvant effectively enhances the immunogenicity of the influenza vaccine", *Vaccine* (2006), 24:1073-1080.

Selander, K., et al., "The Effects of bisphosphonates on the Resorption Cycle of Isolated Osteoclasts", *Calcified Tissue International* (1994), 55:368-375.

Selander, K., et al., "Characteristics of Clodronate-Induced Apoptosis in Osteoclasts and Macrophages", *Molecular Pharmacology* (1996), 50:1127-1138.

Sen, G., et al., "Immunization of Aged Mice with a Pneumococcal Conjugate Vaccine Combined with an Unmethylated CpG-Containing Oligodeoxynucleotide Restores Defective Immunoglobulin G Antipolysaccharide Responses and Specific CD4+-T-Cell Priming to Young Adult Levels", *Infection and Immunity* (2006), 74(4):2177-2186.

Serafini, P., et al., "Myeloid suppressor cells in cancer: recruitment, phenotype, properties, and mechanisms of immune suppression", *Seminars in Cancer Biology* (2006)16:53-65.

Sica, A., "Role of tumour-associated macrophages in cancer-related inflammation", *Experimental Oncology* (Sep. 2010), 32(3):153-158.

Sigurdsson, E., et al., "Immunization Delays the Onset of Prion Disease in Mice", *American Journal of Pathology* (Jul. 2002), 161(1):13-17.

Skorupski, K., et al., "CCNU for the Treatment of Dogs with Histiocytic Sarcoma", *J Vet Intern Med* (2007), 21:121-126.

Solinas, G., et al., "Inflammation-mediated promotion of invasion and metastasis", *Cancer Metastasis Rev* (2010), 29:243-248.

Souan, L., et al., "Modulation of proteinase-K resistant prion protein by prion peptide immunization", *Eur. J. Immunol.* (2001), 31:2338-2346.

Stewart, V., et al., "Pre-clinical evaluation of new adjuvant formulations to improve the immunogenicity of the malaria vaccine RTS,S/ASO2A", *Vaccine* (2006), 24:6483-6492.

Sugai, T., et al., "A CpG-containing oligodeoxynucleotide as an efficient adjuvant counterbalancing the Th1/Th2 immune response in diphtheria-tetanus-pertussis vaccine", *Vaccine* (2005), 23:5450-5456.

Suli, J., et al., "Experimental squalene adjuvant I. Preparation and testing of its effectiveness", *Vaccine* (2004), 22:3464-3469.

Tacke, F., et al., "Monocyte subsets differentially employ CCR2, CCR5, and CX3CR1 to accumulate within atherosclerotic plaques", *The Journal of Clinical Investigation* (Jan. 2007), 117(1):185-194.

The Australasian Gene Therapy Society, 4th Society Meeting, Apr. 27-29, 2005, The Journal of Gene Medicine (2005), 7(8):1113-1143.

Theeten, H., et al., "Effects of lowering the aluminium content of a dTpa vaccine on its immunogenicity and reactogenicity when given as a booster to adolescents", *Vaccine* (2005), 23:1515-1521.

Twentyman, P.R., et al., "A study of some variables in a tetrazolium dye (MTT) based assay for cell growth and chemosensitivity", *Br. J. Cancer* (1987), 56:279-285.

van Engeland, M., et al., "Annexin V-Affinity Assay: A Review on an Apoptosis Detection System Based on Phosphatidylserine Exposure", *Cytometry* (1998), 31:1-9.

van Rooijen, N., et al., "Effects of Intracellular Diphosphonates on Cells of the Mononuclear Phagocyte System: In Vivo Effects of Liposome-Encapsulated Diphosphonates on Different Macrophage Subpopulations in the Spleen", *Calcif Tissue Int* (1989), 45(3):153-156.

van Rooijen, N., et al., "In vitro and in vivo elimination of macrophage tumor cells using liposome-encapsulated dichloromethylene diphosphonate", *Virchows Archiv B Cell Pathol* (1988), 54(4):241-245.

(56) References Cited

OTHER PUBLICATIONS van Rooijen, N., et al., "Liposome mediated depletion of macrophages: mechanism of action, preparation of liposomes and applications", *Journal of Immunological Methods* (1994), 174:83-93.

van Rooijen, N., et al., "Apoptosis of macrophages induced by liposome-mediated intracellular delivery of clodronate and propamidine", *Journal of Immunological Methods* (1996), 193:93-99.

Vermes, I., et al., "A novel assay for apoptosis Flow cytometric detection of phosphatidylserine expression on early apoptotic cells using fluorescein labelled Annexin V", *Journal of Immunological Methods* (1995), 184:39-51.

Villikka, K., et al., "The Absolute Bioavailability of Clodronate From Two Different Oral Doses", *Bone* (Sep. 2002), 31(3) 418-421.

Vitetta, E., et al., "A pilot clinical trial of a recombinant ricin vaccine in normal humans", *Proc. Natl. Acad. Sci.* (Feb. 14, 2006), 103(7):2268-2273.

Wellman, M., et al., "A Macrophage-Monocyte Cell Line From a Dog with Malignant Histiocytosis", *In Vitro Cellular & Developmental Biology* (Mar. 1988), vol. 24, No. 3, Part I, pp. 223-229.

Witz, I. P., "Tumor-microenvironment interactions: dangerous liaisons," *Advances in Cancer Research* (2008), 100:203-229.

Xia, et al., "Recent Developments in CCR2 Antagonists", *Expert Opin. Ther. Patents*, Johnson & Johnson Pharmaceutical Research and Development, Cranbury, New Jersey, USA, (2009), 19(3):295-303.

Youn, J-I et al., "The biology of myeloid-derived suppressor cells: the blessing and the curse of morphological and functional heterogeneity," *Eur J Immunol.* (Nov. 2010), 40(11):2969-2975.

Zavodovskaya, R., et al., "Evaluation of dysregulation of the receptor tyrosine kinases Kit, Flt3, and Met in histiocytic sarcomas of dogs", *J Am Vet Med Assoc* (2006), 67(4):633-641.

Zeisberger, SM, et al., "Clodronate-liposome-mediated depletion of tumour-associated macrophages: a new and highly effective antiangiogenic therapy approach", *British Journal of Cancer* (2006), 95:272-281.

\* cited by examiner

METHODS AND COMPOSITIONS FOR ENHANCING AN IMMUNE RESPONSE, BLOCKING MONOCYTE MIGRATION, AMPLIFYING VACCINE IMMUNITY AND INHIBITING TUMOR GROWTH AND METASTASIS

CROSS REFERENCE TO RELATED APPLICATIONS

This application is a divisional of U.S. application Ser. No. 14/609,146, filed Jan. 29, 2015, now issued U.S. Pat. No. 9,539,314, granted Jan. 10, 2017; which is a divisional of U.S. patent application Ser. No. 14/195,688, filed Mar. 3, 2014, now issued U.S. Pat. No. 8,975,290, granted Mar. 10, 2015; which claims priority to U.S. Provisional Application No. 61/771,738, filed on Mar. 1, 2013, and U.S. Provisional Application No. 61/771,744, filed on Mar. 1, 2013, each of which is incorporated by reference herein in its entirety.

FIELD OF THE INVENTION

The present invention provides methods for enhancing an immune response, decreasing monocyte recruitment to lymph nodes, amplifying vaccine immunity, and reducing tumor growth or metastasis. The invention also includes compositions and kits used to practice these methods.

BACKGROUND OF THE INVENTION

Vaccine adjuvant-induced inflammation augments vaccine immunity in part by recruiting antigen presenting myeloid cells (monocytes and neutrophils) to vaccine draining lymph nodes (LNs) (Serafini et al. (2004) Cancer Res. 64:6337-6343; Martino et al. (2010) J. Immunol. 184: 2038-2047). However, recent evidence indicates that monocyte recruitment to LNs suppresses local B cell and T cell activation and proliferation (Mitchell et al. (2012) J. Immunology 189: 5612-5621; Mitchell et al. (2012) Int. Immunopharmacol. 15: 357-363). Lowered immune responses following vaccination can lead to decreased vaccine efficacy.

Moreover, the role of immature and immune suppressive myeloid cells, including neutrophils, monocytes, and tumor-associated macrophages, in promoting the growth of primary tumors is well established[1-10]. Additionally, myeloid cells, and especially monocytes play an important role in creating favorable conditions for the seeding and growth of tumor metastases in the lungs, in part by establishing the so-called metastatic niche[15-17]. Inflammatory monocytes recruited in response to tumor-derived signals have been shown to play a key role in promoting the growth of tumor metastases. The major chemokine regulating monocyte recruitment is MCP-1 (CCL2), which signals primarily via activation of the receptor CCR2 expressed principally on inflammatory monocytes.

What are needed in the art, are methods for administering vaccines and related vaccine compositions that enhance the immune response to an antigen and augment vaccine efficacy by inhibiting the suppressive effects of monocytes at LNs and enhancing B cell and T cell responses. What is also needed in the art, are methods for inhibiting the migration of myeloid cells, and in particular inflammatory monocytes, to the site of tumors where they act to promote tumor growth and metastasis. The present invention is directed to overcoming these deficiencies in the art.

BRIEF SUMMARY OF THE INVENTION

In one aspect, the invention provides a method of enhancing an immune response against an antigen in an individual, the method comprising:
  (a) administering to the individual an effective amount of the antigen in conjunction with a compound of Formula (I):

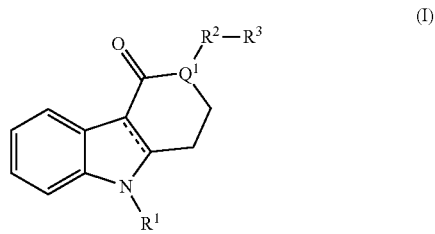

wherein
  $R^1$ is hydrogen or $C_{1-6}$ alkyl;
  ⸺ is a single bond or double bond;
  $Q^1$ is N or CH;
  $R^2$ is selected from hydrogen and $C_{1-6}$ alkylene, wherein one carbon unit of said alkylene is optionally replaced with —O—, —S—, —SO—, —SO$_2$—, —NR$^a$—, or —CO—; wherein $R^a$ is hydrogen or $C_{1-6}$ alkyl; and
  $R^3$ is hydrogen or an optionally substituted 5-membered heteroaryl ring; wherein the heteroaryl ring is optionally substituted with $C_{1-6}$ alkyl;
or pharmaceutically acceptable salts thereof; or
  (b) administering to the individual an effective amount of an angiotensin II receptor blocker (ARB) in conjunction with the antigen, thereby enhancing the immune response.

In some embodiments, the compound of Formula (I) is a compound of Formula (II), Formula (III), or Formula (IV), as described herein. In certain embodiments, the compound of Formula (I) is Ondansteron or Alosetron. In certain embodiments, the ARB is Losartan, Candesartan, Eprosartan, Irbesartan, Olmesartan, Telmisartan, Azilsartan, or Valsartan.

In certain embodiments, the enhanced immune response comprises an enhanced humoral immune response. In certain embodiments, the enhanced humoral immune response comprises an increased antibody titer against the antigen. In certain embodiments, the enhanced immune response comprises an enhanced cellular immune response. In certain embodiments, the enhanced cellular immune response comprises increased release of IFNγ in response to the antigen. In certain embodiments, the enhanced immune response comprises an enhanced humoral immune response and an enhanced cellular immune response.

In certain embodiments, the antigen comprises live whole virus, killed whole virus, attenuated whole virus, killed bacteria, attenuated bacteria, a virus-like particle, a bacterial, viral, or parasite protein, a recombinant protein, or a peptide.

In certain embodiments comprising administering an ARB, the individual receiving an ARB does not have hypertension, congestive heart failure, a history of myocardial infarction, or diabetic nephropathy. In certain embodiments, the individual receiving an ARB has not taken the ARB for the treatment of hypertension, congestive heart failure, or diabetic nephropathy. In certain embodiments, the individual receiving an ARB does not have a detectable level of the ARB in their blood or urine prior to administration of the ARB in conjunction with the antigen.

In certain embodiments, the antigen and the ARB are present in a single pharmaceutical composition. In certain embodiments, the antigen and the compound of Formula (I) are present in a single pharmaceutical composition. In certain embodiments, the single pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally.

In certain embodiments, the ARB is present in a first pharmaceutical composition, and the antigen is present in a second pharmaceutical composition. In certain embodiments, the compound of Formula (I) is present in a first pharmaceutical composition, and the antigen is present in a second pharmaceutical composition. In certain embodiments, the first pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally. In certain embodiments, the second pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally. In certain embodiments, the first pharmaceutical composition is administered before the second pharmaceutical composition. In certain embodiments, the first pharmaceutical composition is administered after the second pharmaceutical composition. In certain embodiments, the first and second pharmaceutical compositions are administered within a time period of less than 12 hours of one another. In certain embodiments, the first pharmaceutical composition and the second pharmaceutical compositions are administered simultaneously.

In certain embodiments, the ARB is Losartan, and the Losartan is administered at a dosage of 30 mg/kg. In certain embodiments, the ARB is Losartan, and the Losartan is administered at a dosage of less than 25 mg. In certain embodiments, the ARB is Candesartan, and the Candesartan is administered at a dosage of less than 4 mg. In certain embodiments, the ARB is Eprosartan, and the Eprosartan is administered at a dosage of less than 400 mg. In certain embodiments, the ARB is Irbesartan, and the Irbesartan is administered at a dosage of less than 150 mg. In certain embodiments, the ARB is Olmesartan, and the Olmesartan is administered at a dosage of less than 20 mg. In certain embodiments, the ARB is Telmisartan, and the Telmisartan is administered at a dosage of less than 20 mg. In certain embodiments, the ARB is Valsartan, and the Valsartan is administered at a dosage of less than 20 mg. In certain embodiments, the ARB is Azilsartan, and the Azilsartan is administered at a dosage of less than 80 mg.

In some embodiments, the compound of Formula (I) is a compound of Formula (II):

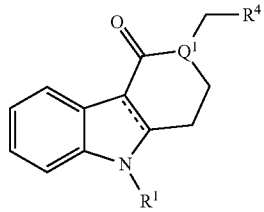

wherein $R^1$ is hydrogen or $C_{1-6}$ alkyl;

$\text{---}$ is a single bond or double bond;

$Q^1$ is N or CH; and $R^4$ is an optionally substituted 5-membered heteroaryl ring; wherein the heteroaryl ring is optionally substituted with $C_{1-6}$ alkyl;

or pharmaceutically acceptable salts thereof.

In some embodiments, the compound of Formula (I) is a compound of Formula (III):

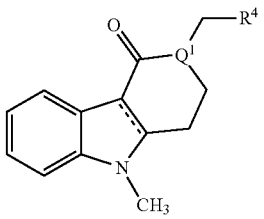

wherein $\text{---}$ is a single bond or double bond;

$Q^1$ is N or CH; and $R^4$ is an optionally substituted 5-membered heteroaryl ring; wherein the heteroaryl ring is optionally substituted with $C_{1-6}$ alkyl;

or pharmaceutically acceptable salts thereof.

In some embodiments, the compound of Formula (I) is a compound of Formula (IV):

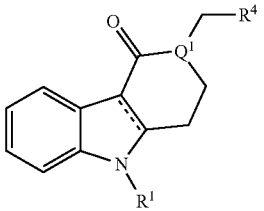

wherein $R^1$ is hydrogen or $C_{1-6}$ alkyl;

$\text{---}$ is a single bond or double bond;

$Q^1$ is N or CH; and $R^4$ is selected from and H

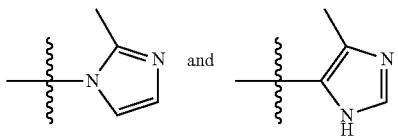

or pharmaceutically acceptable salts thereof.

In some embodiments, the compound of Formula (I) is a compound of Formula (V):

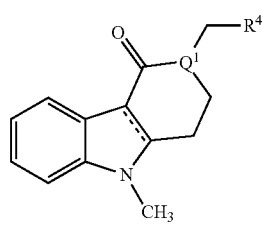

wherein

┅ is a single bond or double bond;

Q is N or CH, and $R^4$ is selected from

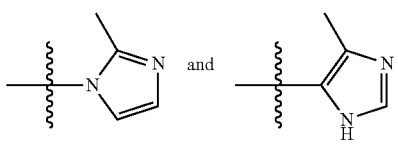

or pharmaceutically acceptable salts thereof.

In some embodiments, the compound of Formula (I) is Ondansetron. In some embodiments, the Ondansetron is administered at a dosage of 3 mg/kg. In some embodiments, the Ondansetron is administered at a dosage of less than 12 mg. In some embodiments, the compound of Formula (I) is Alosetron. In some embodiments, the Alosetron is administered at a dosage of less than 0.5 mg.

In some embodiments comprising administering a Ondansetron or Alosetron, the individual has not taken the Ondansetron or the Alosetron for the treatment of irritable bowel syndrome (IBS), post-operative nausea and vomiting (PONV), radiation-induced nausea and vomiting (RINV), or chemotherapy-induced nausea and vomiting (CINV). In some embodiments, the individual does not have a detectable level of the Ondansetron or the Alosetron in their blood or urine prior to administration of the Ondansetron or the Alosetron in conjunction with the antigen In some embodiments, the present invention provides a method of decreasing recruitment of monocytes to a lymph node in an individual, the method comprising:

(a) administering to the individual an antigen in conjunction with an effective amount of a compound of Formula (I):

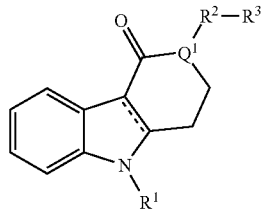

wherein $R^1$ is hydrogen or $C_{1-6}$ alkyl;

┅ is a single bond or double bond;

$Q^1$ is N or CH;

$R^2$ is selected from hydrogen and $C_{1-6}$ alkylene, wherein one carbon unit of said alkylene is optionally replaced with —O—, —S—, —SO—, —SO$_2$—, —NR$^a$—, or —CO—; wherein $R^a$ is hydrogen or $C_{1-6}$ alkyl; and $R^3$ is hydrogen or an optionally substituted 5-membered heteroaryl ring; wherein the heteroaryl ring is optionally substituted with $C_{1-6}$ alkyl;

or pharmaceutically acceptable salts thereof; or (b) administering to the individual an effective amount of an angiotensin II receptor blocker (ARB) in conjunction with an antigen, thereby decreasing the recruitment of the monocytes to lymph node.

In some embodiments, the compound of Formula (I) is a compound of Formula (II), Formula (III), or Formula (IV), as described herein. In certain embodiments, the compound of Formula (I) is Ondansteron or Alosetron.

In certain embodiments, the ARB is Losartan, Candesartan, Eprosartan, Irbesartan, Olmesartan, Telmisartan, Azilsartan, or Valsartan.

In certain embodiments, the monocytes are inflammatory monocytes or CD14$^{hi}$CD16$^-$ human monocytes. In certain embodiments, the lymph node is a draining lymph node. In certain embodiments, the draining lymph node is a vaccine draining lymph node.

In certain embodiments comprising administering an ARB, the enhanced immune response comprises an enhanced humoral immune response. In certain embodiments, the enhanced humoral immune response comprises an increased antibody titer against the antigen. In certain embodiments, the enhanced immune response comprises an enhanced cellular immune response. In certain embodiments, the enhanced cellular immune response comprises increased release of IFNγ in response to the antigen. In certain embodiments, the enhanced immune response comprises an enhanced humoral immune response and an enhanced cellular immune response.

In certain embodiments, the antigen comprises live whole virus, killed whole virus, attenuated whole virus, killed bacteria, attenuated bacteria, a virus-like particle, a bacterial, viral, or parasite protein, a recombinant protein, or a peptide.

In certain embodiments comprising administering an ARB, the individual receiving an ARB does not have hypertension, congestive heart failure, a history of myocardial infarction, or diabetic nephropathy. In certain embodiments, the individual receiving an ARB has not taken the ARB for the treatment of hypertension, congestive heart failure, or diabetic nephropathy. In certain embodiments, the individual receiving an ARB does not have a detectable level of the ARB in their blood or urine prior to administration of the ARB in conjunction with the antigen.

In certain embodiments, the antigen and the ARB are present in a single pharmaceutical composition. In certain embodiments, the antigen and the compound of Formula (I) are present in a single pharmaceutical composition. In certain embodiments, the single pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally.

In certain embodiments, the ARB is present in a first pharmaceutical composition and the antigen is present in a second pharmaceutical composition. In certain embodiments, the compound of Formula (I) is present in a first pharmaceutical composition and the antigen is present in a second pharmaceutical composition. In certain embodiments, the first pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally. In certain embodiments, the second pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally. In certain embodiments, the first pharmaceutical composition is administered before the second pharmaceutical composition. In certain embodiments, the first pharmaceutical composition is administered after the second pharmaceutical composition. In certain embodiments, the first and second pharmaceutical compositions are administered within a time period of less than 12 hours of one another. In certain embodiments, the first pharmaceutical composition and the second pharmaceutical compositions are administered simultaneously.

In certain embodiments, the ARB is Losartan, and the Losartan is administered at a dosage of 30 mg/kg. In certain embodiments, the ARB is Losartan, and the Losartan is administered at a dosage of less than 25 mg. In certain embodiments, the ARB is Candesartan, and the Candesartan is administered at a dosage of less than 4 mg. In certain embodiments, the ARB is Eprosartan, and the Eprosartan is administered at a dosage of less than 400 mg. In certain embodiments, the ARB is Irbesartan, and the Irbesartan is administered at a dosage of less than 150 mg. In certain embodiments, the ARB is Olmesartan, and the Olmesartan is administered at a dosage of less than 20 mg. In certain embodiments, the ARB is Telmisartan, and the Telmisartan is administered at a dosage of less than 20 mg. In certain embodiments, the ARB is Valsartan, and the Valsartan is administered at a dosage of less than 20 mg. In certain embodiments, the ARB is Azilsartan, and the Azilsartan is administered at a dosage of less than 80 mg.

In some embodiments, the compound of Formula (I) is a compound of Formula (II):

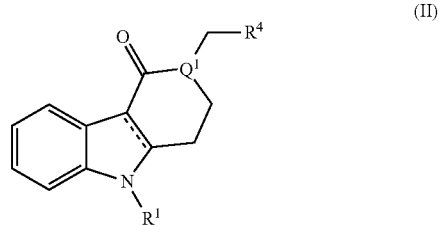

wherein $R^1$ is hydrogen or $C_{1-6}$ alkyl;

$\text{---}$ is a single bond or double bond;

$Q^1$ is N or CH; and $R^4$ is an optionally substituted 5-membered heteroaryl ring; wherein the heteroaryl ring is optionally substituted with $C_{1-6}$ alkyl;

or pharmaceutically acceptable salts thereof.

In some embodiments, the compound of Formula (I) is a compound of Formula (III):

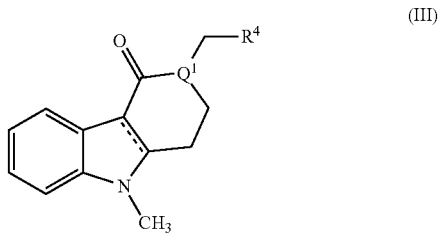

wherein $\text{---}$ is a single bond or double bond;

$Q^1$ is N or CH; and $R^4$ is an optionally substituted 5-membered heteroaryl ring; wherein the heteroaryl ring is optionally substituted with $C_{1-6}$ alkyl;

or pharmaceutically acceptable salts thereof.

In some embodiments, the compound of Formula (I) is s a compound of Formula (IV):

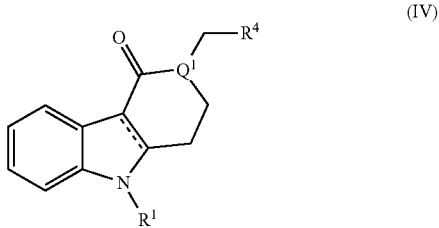

wherein $R^1$ is hydrogen or $C_{1-6}$ alkyl;

$\text{---}$ is a single bond or double bond;

$Q^1$ is N or CH;

$R^4$ is selected from

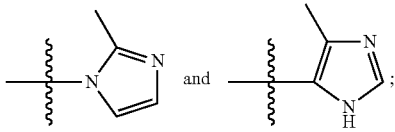

or pharmaceutically acceptable salts thereof.

In some embodiments, the compound of Formula (I) is a compound of Formula (V):

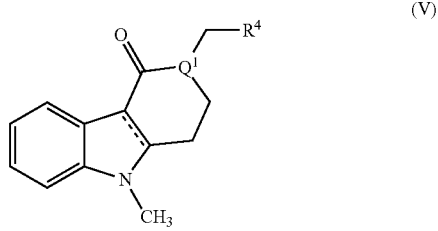

wherein

---- is a single bond or double bond;

$Q^1$ is N or CH; and $R^4$ is selected from

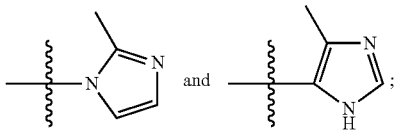

or pharmaceutically acceptable salts thereof.

In some embodiments, the compound of Formula (I) is Ondansetron. In some embodiments, the Ondansetron is administered at a dosage of 3 mg/kg. In some embodiments, the Ondansetron is administered at a dosage of less than 12 mg. In some embodiments, the compound of Formula (I) is Alosetron. In some embodiments, the Alosetron is administered at a dosage of less than 0.5 mg.

In some embodiments, comprising administering a Ondansetron or Alosetron, the individual has not taken the Ondansetron or the Alosetron for the treatment of irritable bowel syndrome (IBS), post-operative nausea and vomiting (PONV), radiation-induced nausea and vomiting (RINV), or chemotherapy-induced nausea and vomiting (CINV). In some embodiments, the individual does not have a detectable level of the Ondansetron or the Alosetron in their blood or urine prior to administration of the Ondansetron or the Alosetron in conjunction with the antigen In some embodiments, the present invention provides a method of amplifying vaccine immunity in an individual, the method comprising (a) administering to the individual the vaccine in conjunction with an effective amount of an ARB or a compound of Formula (I):

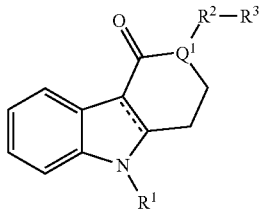

wherein $R^1$ is hydrogen or $C_{1-6}$ alkyl;

---- is a single bond or double bond;

$Q^1$ is N or CH;

$R^2$ is selected from hydrogen and $C_{1-6}$ alkylene, wherein one carbon unit of said alkylene is optionally replaced with —O—, —S—, —SO—, —SO$_2$—, —NR$^a$—, or —CO—; wherein R$^a$ is hydrogen or $C_{1-6}$ alkyl; and $R^3$ is hydrogen or an optionally substituted 5-membered heteroaryl ring; wherein the heteroaryl ring is optionally substituted with $C_{1-6}$ alkyl;

or pharmaceutically acceptable salts thereof; or (b) administering to the individual the vaccine in conjunction with an effective amount of an angiotensin receptor blocker (ARB), thereby amplifying the immunity of the vaccine in the individual.

In some embodiments, the compound of Formula (I) is a compound of Formula (II), Formula (III), or Formula (IV), as described herein. In certain embodiments, the compound of Formula (I) is Ondansteron or Alosetron. In certain embodiments, the ARB is Losartan, Candesartan, Eprosartan, Irbesartan, Olmesartan, Telmisartan, Azilsartan, or Valsartan.

In certain embodiments, the vaccine comprises live whole virus, killed whole virus, attenuated whole virus, killed bacteria, attenuated bacteria, a virus-like particle, a bacterial, viral, or parasite protein, a recombinant protein, or a peptide.

In certain embodiments comprising administering an ARB, the individual receiving an ARB does not have hypertension, congestive heart failure, a history of myocardial infarction, or diabetic nephropathy. In certain embodiments, the individual receiving an ARB has not taken the ARB for the treatment of hypertension, congestive heart failure, or diabetic nephropathy. In certain embodiments, the individual receiving an ARB does not have a detectable level of the ARB in their blood or urine prior to administration of the ARB in conjunction with the antigen or vaccine.

In certain embodiments, the antigen or vaccine and the ARB are present in a single pharmaceutical composition. In certain embodiments, the vaccine and the compound of Formula (I) are present in a single pharmaceutical composition. In certain embodiments, the single pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally.

In certain embodiments, the ARB is present in a first pharmaceutical composition and the antigen or vaccine is present in a second pharmaceutical composition. In certain embodiments, the compound of Formula (I) is present in a first pharmaceutical composition and the vaccine is present in a second pharmaceutical composition. In certain embodiments, the first pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally. In certain embodiments, the second pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally. In certain embodiments, the first pharmaceutical composition is administered before the second pharmaceutical composition. In certain embodiments, the first pharmaceutical composition is administered after the second pharmaceutical composition. In certain embodiments, the first and second pharmaceutical compositions are administered within a time period of less than 12 hours of one another. In certain embodiments, the first pharmaceutical composition and the second pharmaceutical compositions are administered simultaneously.

In certain embodiments, the ARB is Losartan, and the Losartan is administered at a dosage of 30 mg/kg. In certain embodiments, the ARB is Losartan, and the Losartan is administered at a dosage of less than 25 mg. In certain embodiments, the ARB is Candesartan, and the Candesartan is administered at a dosage of less than 4 mg. In certain embodiments, the ARB is Eprosartan, and the Eprosartan is administered at a dosage of less than 400 mg. In certain embodiments, the ARB is Irbesartan, and the Irbesartan is administered at a dosage of less than 150 mg. In certain embodiments, the ARB is Olmesartan, and the Olmesartan is administered at a dosage of less than 20 mg. In certain embodiments, the ARB is Telmisartan, and the Telmisartan is administered at a dosage of less than 20 mg. In certain embodiments, the ARB is Valsartan, and the Valsartan is administered at a dosage of less than 20 mg. In certain embodiments, the ARB is Azilsartan, and the Azilsartan is administered at a dosage of less than 80 mg.

In some embodiments, the compound of Formula (I) is a compound of Formula (II):

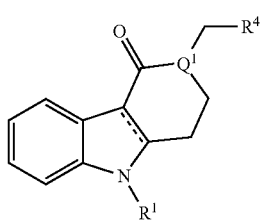

(II)

wherein
$R^1$ is hydrogen or $C_{1-6}$ alkyl;
⸺ is a single bond or double bond;
$Q^1$ is N or CH;
$R^4$ is an optionally substituted 5-membered heteroaryl ring; wherein the heteroaryl ring is optionally substituted with $C_{1-6}$ alkyl;
or pharmaceutically acceptable salts thereof.

In some embodiments, the compound of Formula (I) is a compound of Formula (III):

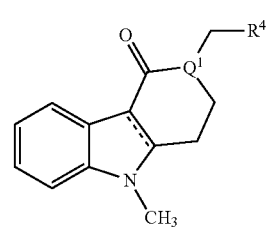

(III)

wherein
⸺ is a single bond or double bond;
$Q^1$ is N or CH; and
$R^4$ is an optionally substituted 5-membered heteroaryl ring; wherein the heteroaryl ring is optionally substituted with $C_{1-6}$ alkyl;
or pharmaceutically acceptable salts thereof.

In some embodiments, the compound of Formula (I) is a compound of Formula (IV):

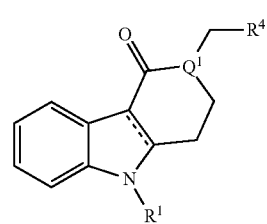

(IV)

wherein
$R^1$ is hydrogen or $C_{1-6}$ alkyl;
⸺ is a single bond or double bond;
$Q^1$ is N or CH; and
$R^4$ is selected from

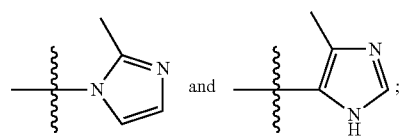

or pharmaceutically acceptable salts thereof.

In some embodiments, the compound of Formula (I) is a compound of Formula (V):

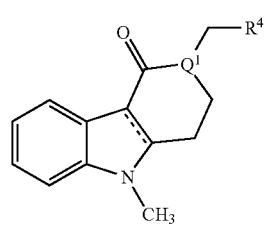

(V)

wherein
  ---- is a single bond or double bond;
  $Q^1$ is N or CH; and
  $R^4$ is selected from

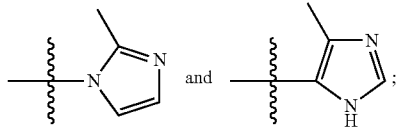

or pharmaceutically acceptable salts thereof.

In some embodiments, the compound of Formula (I) is Ondansetron. In some embodiments, the Ondansetron is administered at a dosage of 3 mg/kg. In some embodiments, the Ondansetron is administered at a dosage of less than 12 mg. In some embodiments, the compound of Formula (I) is Alosetron. In some embodiments, the Alosetron is administered at a dosage of less than 0.5 mg.

In some embodiments comprising administering a Ondansetron or Alosetron, the individual has not taken the Ondansetron or the Alosetron for the treatment of irritable bowel syndrome (IBS), post-operative nausea and vomiting (PONV), radiation-induced nausea and vomiting (RINV), or chemotherapy-induced nausea and vomiting (CINV). In some embodiments, the individual does not have a detectable level of the Ondansetron or the Alosetron in their blood or urine prior to administration of the Ondansetron or the Alosetron in conjunction with the antigen or vaccine.

In some embodiments, the present invention provides a method of inhibiting tumor growth or metastasis in an individual with cancer, the method comprising
  (a) administering to the individual an anti-tumor preparation in conjunction with an effective amount of a compound of Formula (I):

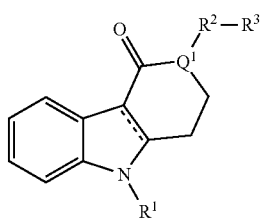

wherein
  $R^1$ is hydrogen or $C_{1-6}$ alkyl;
  ---- is a single bond or double bond;
  $Q^1$ is N or CH;
  $R^2$ is selected from hydrogen and $C_{1-6}$ alkylene, wherein one carbon unit of said alkylene is optionally replaced with —O—, —S—, —SO—, —SO$_2$—, —NR$^a$—, or —CO—; wherein $R^a$ is hydrogen or $C_{1-6}$ alkyl; and
  $R^3$ is hydrogen or an optionally substituted 5-membered heteroaryl ring; wherein the heteroaryl ring is optionally substituted with $C_{1-6}$ alkyl;
or pharmaceutically acceptable salts thereof, or
  (b) administering to the individual an anti-tumor preparation in conjunction with an effective amount of an angiotensin II receptor blocker (ARB), thereby inhibiting tumor growth or metastasis in the individual.

In some embodiments, the compound of Formula (I) is a compound of Formula (II), Formula (III), or Formula (IV), as described herein. In certain embodiments, the compound of Formula (I) is Ondansteron or Alosetron. In certain embodiments, the ARB is Losartan, Candesartan, Eprosartan, Irbesartan, Olmesartan, Telmisartan, Azilsartan, or Valsartan.

In certain embodiments, the anti-tumor preparation comprises a therapeutic antibody, a topoisomerase inhibitor, an antimetabolite, a platinum-based agent, an alkylating agent, a tyrosine kinase inhibitor, an Anthracycline antibiotic, an anti-angiogenic agent, or a vinca alkaloid. In certain embodiments, the tyrosine kinase inhibitor is Sunitinib.

In certain embodiments, the cancer is an epithelial cancer, breast cancer, prostate cancer, colon cancer, a hematopoietic cancer, leukemia, lymphoma, a sarcoma, melanoma, a head sarcoma, a neck sarcoma, a squamous cell carcinoma, an osteosarcoma, or a brain tumor.

In certain embodiments comprising administering an ARB, the individual receiving an ARB does not have hypertension, congestive heart failure, a history of myocardial infarction, or diabetic nephropathy. In certain embodiments, the individual receiving an ARB has not taken the ARB for the treatment of hypertension, congestive heart failure, or diabetic nephropathy. In certain embodiments, the individual receiving an ARB does not have a detectable level of the ARB in their blood or urine prior to administration of the ARB in conjunction with the antigen or anti-tumor preparation.

In certain embodiments, the anti-tumor preparation and the ARB are present in a single pharmaceutical composition. In certain embodiments, the anti-tumor preparation and the compound of Formula (I) are present in a single pharmaceutical composition. In certain embodiments, the single pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally.

In certain embodiments, the ARB is present in a first pharmaceutical composition, and the anti-tumor preparation is present in a second pharmaceutical composition. In certain embodiments, the compound of Formula (I) is present in a first pharmaceutical composition, and the anti-tumor preparation is present in a second pharmaceutical composition. In certain embodiments, the first pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally. In certain embodiments, the second pharmaceutical composition is administered orally, via topical application, inhalation, intravenous injection, intra-arterial injection, intramuscular injection, application to a wound site, application to a surgical site, intracavitary injection, by suppository, subcutaneously, intradermally, transcutaneously, by nebulization, intraplurally, intraperitoneally, intraventricularly, intra-articularly, intraocularly, or intraspinally. In certain embodiments, the first pharmaceutical composition is administered before the second pharmaceutical composition. In certain embodiments, the first pharmaceutical composition is administered after the second pharmaceutical composition. In certain embodiments, the first and second pharmaceutical compositions are administered within a time period of less than 12 hours of one another. In certain embodiments, the first pharmaceutical composition and the second pharmaceutical compositions are administered simultaneously.

In certain embodiments, the ARB is Losartan, and the Losartan is administered at a dosage of 30 mg/kg. In certain embodiments, the ARB is Losartan, and the Losartan is administered at a dosage of less than 25 mg. In certain embodiments, the ARB is Candesartan, and the Candesartan is administered at a dosage of less than 4 mg. In certain embodiments, the ARB is Eprosartan, and the Eprosartan is administered at a dosage of less than 400 mg. In certain embodiments, the ARB is Irbesartan, and the Irbesartan is administered at a dosage of less than 150 mg. In certain embodiments, the ARB is Olmesartan, and the Olmesartan is administered at a dosage of less than 20 mg. In certain embodiments, the ARB is Telmisartan, and the Telmisartan is administered at a dosage of less than 20 mg. In certain embodiments, the ARB is Valsartan, and the Valsartan is administered at a dosage of less than 20 mg. In certain embodiments, the ARB is Azilsartan, and the Azilsartan is administered at a dosage of less than 80 mg.

In some embodiments, the ARB is losartan, and the anti-tumor preparation is a tyrosine kinase inhibitor. In one certain embodiment, the ARB is losartan and the anti-tumor preparation is the tyrosine kinase inhibitor sunitinib.

In some embodiments, the compound of Formula (I) is a compound of Formula (II):

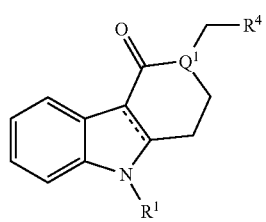

(II)

wherein
R$^1$ is hydrogen or C$_{1-6}$ alkyl;
⋯ is a single bond or double bond;
Q$^1$ is N or CH; and
R$^4$ is an optionally substituted 5-membered heteroaryl ring; wherein the heteroaryl ring is optionally substituted with C$_{1-6}$ alkyl;
or pharmaceutically acceptable salts thereof.

In some embodiments, the compound of Formula (I) is a compound of Formula (III):

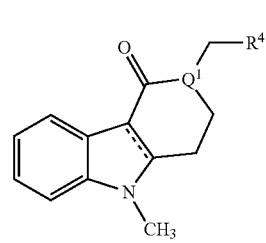

(III)

wherein
⋯ is a single bond or double bond;
Q$^1$ is N or CH; and

R$^4$ is an optionally substituted 5-membered heteroaryl ring; wherein the heteroaryl ring is optionally substituted with C$_{1-6}$ alkyl;
or pharmaceutically acceptable salts thereof.

In some embodiments, the compound of Formula (I) is a compound of Formula (IV):

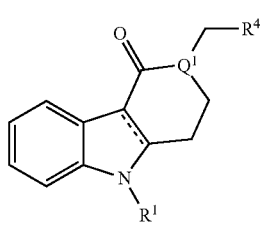

(IV)

wherein
R$^1$ is hydrogen or C$_{1-6}$ alkyl;
⋯ is a single bond or double bond;
Q$^1$ is N or CH; and
R$^4$ is selected from

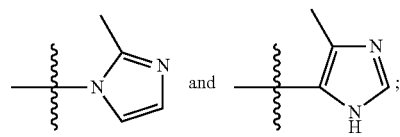

or pharmaceutically acceptable salts thereof.

In some embodiments, the compound of Formula (I) is a compound of Formula (V):

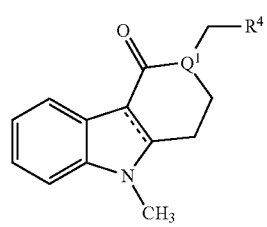

(V)

wherein
⋯ is a single bond or double bond;
Q$^1$ is N or CH; and
R$^4$ is selected from

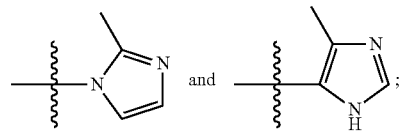

or pharmaceutically acceptable salts thereof.

In some embodiments, the compound of Formula (I) is Ondansetron. In some embodiments, the Ondansetron is administered at a dosage of 3 mg/kg. In some embodiments, the Ondansetron is administered at a dosage of less than 12 mg. In some embodiments, the compound of Formula (I) is Alosetron. In some embodiments, the Alosetron is administered at a dosage of less than 0.5 mg.

In some embodiments, comprising administering Ondansetron or Alosetron, the individual has not taken the Ondansetron or the Alosetron for the treatment of irritable bowel syndrome (IBS), post-operative nausea and vomiting (PONV), radiation-induced nausea and vomiting (RINV), or chemotherapy-induced nausea and vomiting (CINV). In some embodiments, the individual does not have a detectable level of the Ondansetron or the Alosetron in their blood or urine prior to administration of the Ondansetron or the Alosetron in conjunction with the antigen or anti-tumor preparation.

In some embodiments, the present invention provides a composition comprising (i) an angiotensin II receptor blocker (ARB) and (ii) an antigen or a vaccine. In certain embodiments, the ARB is Azilsartan, Losartan, Candesartan, Eprosartan, Irbesartan, Olmesartan, Telmisartan, or Valsartan. Also provided by the invention is a (pharmaceutical) composition comprising (i) an angiotensin II receptor blocker (ARB), (ii) an antigen or a vaccine, and (iii) a pharmaceutically acceptable carrier. In certain embodiments, the antigen comprises live whole virus, killed whole virus, attenuated whole virus, killed bacteria, attenuated bacteria, a virus-like particle, a bacterial, viral, or parasite protein, a recombinant protein, or a peptide.

In some embodiments, the invention also provides compositions comprising (i) an antigen or a vaccine, and (ii) a compound of Formula (I):

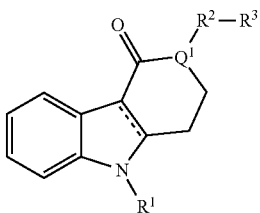

(I)

wherein
R$^1$ is hydrogen or C$_{1-6}$ alkyl;
≈ is a single bond or double bond;
Q$^1$ is N or CH;
R$^2$ is selected from hydrogen and C$_{1-6}$ alkylene, wherein one carbon unit of said alkylene is optionally replaced with —O—, —S—, —SO—, —SO$_2$—, —NR$^a$—, or —CO—; wherein R$^a$ is hydrogen or C$_{1-6}$ alkyl; and
R$^3$ is hydrogen or an optionally substituted 5-membered heteroaryl ring; wherein the heteroaryl ring is optionally substituted with C$_{1-6}$ alkyl;
or pharmaceutically acceptable salts thereof.

In some embodiments, the composition further comprises (iii) a pharmaceutically acceptable carrier. In some embodiments, the compound of Formula (I) is a compound of Formula (II), Formula (III), or Formula (IV), as described herein. In some embodiments, the compound of Formula (I) is Alosetron or Ondansetron. In some embodiments, the antigen or the vaccine comprises live whole virus, killed whole virus, attenuated whole virus, killed bacteria, attenuated bacteria, a virus-like particle, a bacterial, viral, or parasite protein, a recombinant protein, or a peptide.

In some embodiments, the invention provides a composition comprising (i) an anti-tumor preparation and (ii) an angiotensin II receptor blocker (ARB). In certain embodiments, the ARB is Azilsartan, Losartan, Candesartan, Eprosartan, Irbesartan, Olmesartan, Telmisartan, or Valsartan.

The invention also provides pharmaceutical compositions comprising (i) an anti-tumor preparation, (ii) an angiotensin II receptor blocker (ARB), and (iii) a pharmaceutically acceptable carrier. In certain embodiments, the anti-tumor preparation comprises a therapeutic antibody, a topoisomerase inhibitor, an antimetabolite, a platinum-based agent, an alkylating agent, a tyrosine kinase inhibitor, an Anthracycline antibiotic, an anti-angiogenic agent, or a vinca alkaloid. In certain embodiments, the anti-tumor preparation comprises the tyrosine kinase inhibitor sunitinib.

In some embodiments, the invention provides compositions comprising (i) an anti-tumor preparation and (ii) a compound of Formula (I):

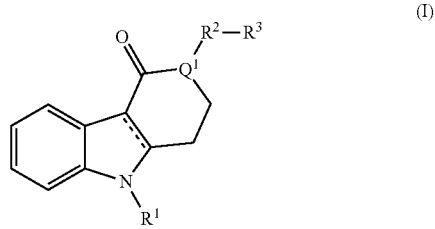

(I)

wherein
R$^1$ is hydrogen or C$_{1-6}$ alkyl;
≈ is a single bond or double bond;
Q$^1$ is N or CH;
R$^2$ is selected from hydrogen and C$_{1-6}$ alkylene, wherein one carbon unit of said alkylene is optionally replaced with —O—, —S—, —SO—, —SO$_2$—, —NR$^a$—, or —CO—; wherein R$^a$ is hydrogen or C$_{1-6}$ alkyl; and
R$^1$ is hydrogen or an optionally substituted 5-membered heteroaryl ring; wherein the heteroaryl ring is optionally substituted with C$_{1-6}$ alkyl;
or pharmaceutically acceptable salts thereof.

In some embodiments, the composition further comprises (iii) a pharmaceutically acceptable carrier. In certain embodiments, the anti-tumor preparation comprises a therapeutic antibody, a topoisomerase inhibitor, an antimetabolite, a platinum-based agent, an alkylating agent, a tyrosine kinase inhibitor, an Anthracycline antibiotic, an anti-angiogenic agent, or a vinca alkaloid. In certain embodiments the compound of Formula (I) is Alosetron or Ondansetron. In certain embodiments, the tyrosine kinase inhibitor is sunitinib.

The invention also provides kits comprising a composition described herein and instructions for use.

The invention also provides kits comprising (i) a vaccine, an antigen, or an anti-tumor preparation, and (ii) a compound of Formula (I)

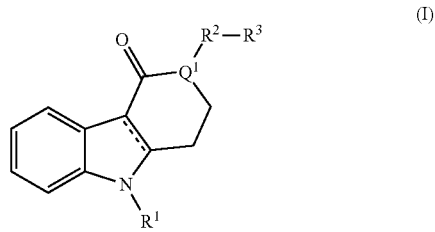

(I)

wherein
R¹ is hydrogen or $C_{1-6}$ alkyl;
⸺ is a single bond or double bond;
$Q^1$ is N or CH,
R² is selected from hydrogen and $C_{1-6}$ alkylene, wherein one carbon unit of said alkylene is optionally replaced with —O—, —S—, —SO—, —SO₂—, —NR$^a$—, or —CO—; wherein R$^a$ is hydrogen or $C_{1-6}$ alkyl; and
R³ is hydrogen or an optionally substituted 5-membered heteroaryl ring; wherein the heteroaryl ring is optionally substituted with $C_{1-6}$ alkyl;
or pharmaceutically acceptable salts thereof, wherein (i) the compound of Formula (I) is provided in a first container, and wherein (ii) the vaccine, antigen, or anti-tumor preparation is provided in a second container. In some embodiments, the compound of Formula (I) is a compound of Formula (II), Formula (III), or Formula (IV), as described herein. In some embodiments, the compound of Formula (I) is Alosetron or Ondansetron.

In certain embodiments, the kit optionally further comprises (iii) instructions for use.

In certain embodiments, kits of the invention comprise (i) an ARB and (ii) a vaccine, an antigen, or an anti-tumor preparation, wherein the ARB is provided in a first container, and wherein the vaccine, antigen, or anti-tumor preparation is provided in a second container. In some embodiments of the kits, the ARB is Azilsartan, Losartan, Candesartan, Eprosartan, Irbesartan, Olmesartan, Telmisartan, or Valsartan.

It is to be understood that one, some, or all of the properties of the various embodiments described herein may be combined to form other embodiments of the present invention. These and other aspects of the invention will become apparent to one of skill in the art.

DETAILED DESCRIPTION OF THE INVENTION

Figure 1:
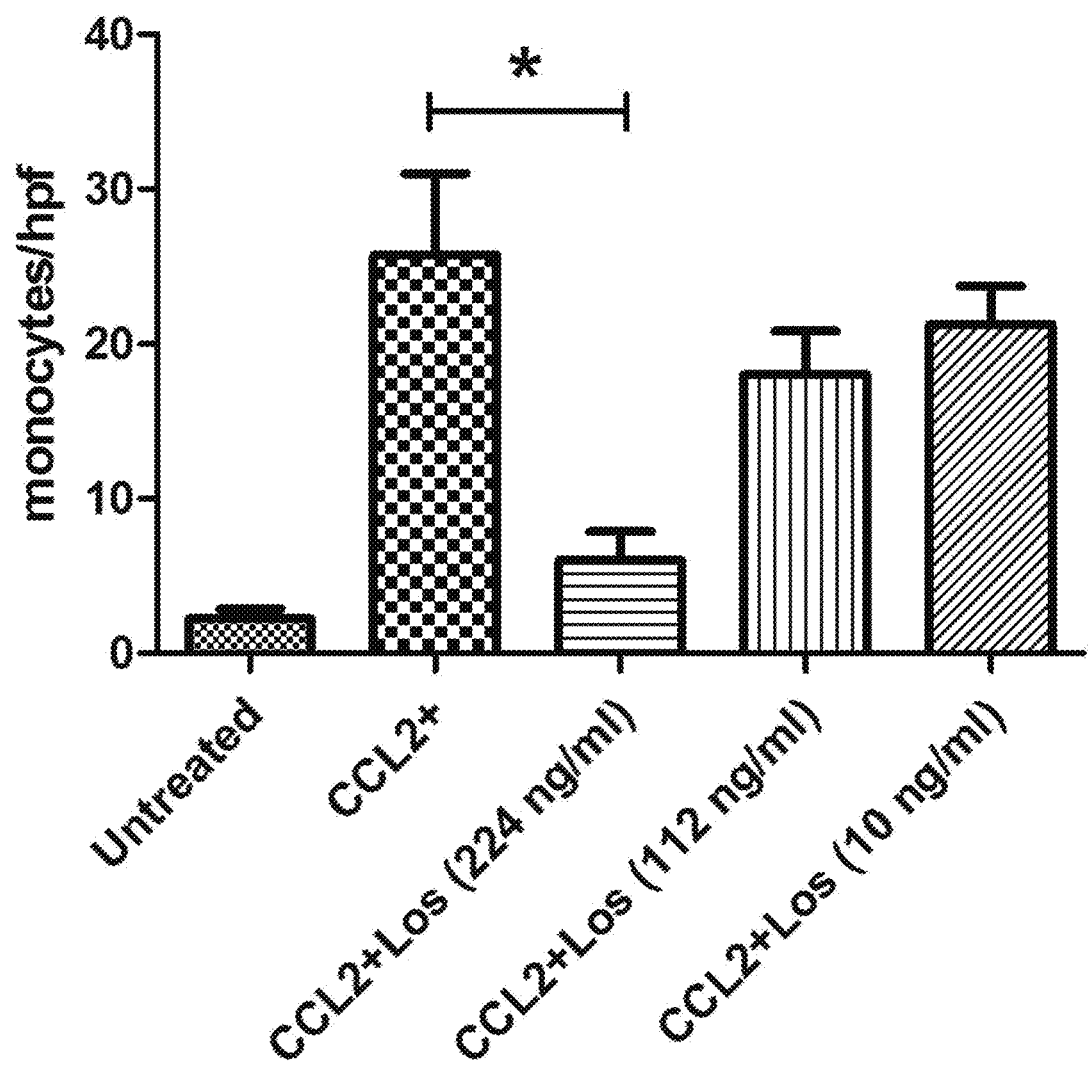
FIG. 1 shows the results of experiments conducted to assess the ability of Losartan to inhibit human monocyte migration in vitro.

The invention provides, inter alia, compositions, methods, and kits for enhancing an immune response in an individual, decreasing the recruitment of monocytes to a lymph node in an individual, amplifying vaccine immunity in an individual, and reducing tumor growth or metastasis in an individual with cancer.

Certain embodiments are based in part on the observation that compounds of Formula

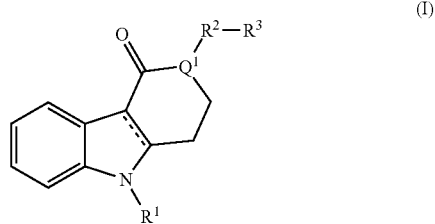

(I)

wherein
R¹ is hydrogen or $C_{1-6}$ alkyl;
⸺ 0 is a single bond or double bond;
$Q^1$ is N or CH;
R² is selected from hydrogen and $C_{1-6}$ alkylene, wherein one carbon unit of said alkylene is optionally replaced with —O—, —S—, —SO—, —SO₂—, —NR$^a$—, or —CO—; wherein R$^a$ is hydrogen or $C_{1-6}$ alkyl; and
R³ is hydrogen or an optionally substituted 5-membered heteroaryl ring; wherein the heteroaryl ring is optionally substituted with $C_{1-6}$ alkyl;
or pharmaceutically acceptable salts thereof, which are typically indicated for treating nausea and vomiting, certain forms of psychosis, symptoms of severe irritable bowel syndrome, tardive dyskinesia, and forms of gastroenteritis, inhibit the migration of monocytes (e.g., migration to vaccine draining lymph nodes), inhibit the suppressive effects of monocytes on vaccine immunity, and inhibit tumor growth and metastasis.

Certain embodiments of the invention are based in part on the observation that angiotensin II receptor blockers (ARBs), which are typically indicated for the treatment of hypertension, inhibit the migration of monocytes (e.g., migration to vaccine draining lymph nodes), inhibit the suppressive effects of monocytes on vaccine immunity, and inhibit tumor growth and metastasis.

General Methods

The practice of the present invention will employ, unless otherwise indicated, conventional techniques of cell culturing, molecular biology (including recombinant techniques), microbiology, cell biology, biochemistry and immunology, which are within the skill of the art. Such techniques are explained fully in the literature, such as, *Molecular Cloning: A Laboratory Manual*, third edition (Sambrook et al., 2001) Cold Spring Harbor Press; *Oligonucleotide Synthesis* (P. Herdewijn, ed., 2004); Animal Cell Culture (R. I. Freshney), ed., 1987), *Methods in Enzymology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Mfolecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Manual of Clinical Laboratory Immunology* (B. Detrick, N. R. Rose, and J. D. Folds eds., 2006); *Immunochemical Protocols* (J. Pound, ed., 2003); *Lab Manual in Biochemistry: Immunology and Biotechnology* (A. Nigam and A. Ayyagari, eds. 2007); *Immunology Methods Manual: The Comprehensive Sourcebook of Techniques* (Ivan Lefkovits, ed., 1996); Using Antibodies: A Laboratory Manual (E. Harlow and D. Lane, eds., 1988); and others.

Definitions

Unless defined otherwise, all technical and scientific terms used herein have the same meaning as commonly understood by those of ordinary skill in the art to which the invention belongs.

As used herein, the term "effective amount" refers to at least an amount effective, at dosages and for periods of time necessary, to achieve the desired result, e.g., an enhanced immune response to an antigen, a decrease in monocyte recruitment to a lymph node following vaccination, an amplification of vaccine immunity, an inhibition of tumor growth and metastasis, etc. An effective amount can be provided in one or more administrations.

As used herein, the term "in conjunction with" refers to the temporal property of two events occurring at approximately the same time, e.g., between 0-12 hours of one another. For example, when an ARB or a compound of Formula (I) is administered in conjunction with an antigen or a vaccine, the ARB or the compound of Formula (I) and the antigen or vaccine are administered within less than a 12 hour period. The term "in conjunction with" is not limited by the order in which the two events occur.

As used herein, the term "individual" refers to a mammal, e.g., a human, a companion animal (e.g., dog, cat, rodent, rabbit, etc.), a sport animal (e.g., horse, dog, bull, etc.), a farm or food animal (e.g., pig, cow, sheep, goat, etc.), livestock (e.g., donkeys, goats, guinea pigs, sheep, cattle, llamas, etc.), or any other mammalian veterinary animal.

As used herein, the singular form "a", "an", and "the" includes plural references unless indicated otherwise.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the invention described herein include "comprising," "consisting," and "consisting essentially of" aspects and embodiments.

Compositions

During vaccination, an antigen is administered to an individual to stimulate antigen-specific immunity, thus increasing the individual's resistance (or decreasing his or her susceptibility) to a particular disease or infection. In order for vaccination to be effective, the antigen must be capable of provoking robust humoral (i.e., B cell) and/or cell-mediated (i.e., T cell) immune responses. However, CCR2 inflammatory monocytes, which are recruited to the site of vaccination and to the vaccine draining lymph nodes, have been shown to have a suppressive effect on B cell and T cell responses (Mitchell et al. (2012) J. Immunology 189: 5612-5621).

In certain embodiments, compositions that include both (i) an angiotensin II receptor blocker (ARB) or a compound of Formula (I); and (ii) an antigen, a vaccine, or an anti-tumor preparation, as described in greater detail herein, are used to reduce monocyte recruitment to lymph nodes, enhance the individual's immune response against the antigen, amplify vaccine immunity, or inhibit tumor growth or metastasis.

Similarly, in certain embodiments, a composition that includes an angiotensin II receptor blocker (ARB) or a compound of Formula (I), when used together with a separate composition that includes an antigen, a vaccine, or an anti-tumor preparation, as described in greater detail herein, are used to reduce monocyte recruitment to lymph nodes, enhance the individual's immune response against the antigen, amplify vaccine immunity, or inhibit tumor growth or metastasis.

Accordingly, in certain embodiments, the present invention provides a composition comprising an ARB or a Compound of Formula (I). In certain embodiments, the present invention includes a composition comprising an antigen, a vaccine, or a tumor preparation. In certain embodiments, the present invention provides a composition comprising (i) an ARB and (ii) an antigen, a vaccine, or a tumor preparation. In certain embodiments, the present invention provides a composition comprising (i) a Compound of Formula (I) and (ii) an antigen, a vaccine, or a tumor preparation. In certain embodiments, such compositions further comprise a pharmaceutically acceptable carrier. In certain embodiments, such compositions are pharmaceutically acceptable compositions. In certain embodiments, such compositions are administered to an individual. In certain embodiments, such compositions are used to reduce monocyte recruitment to lymph nodes, enhance the individual's immune response against the antigen, amplify vaccine immunity, or to inhibit tumor growth or metastasis.

Angiotensin II Receptor Blockers (ARBs)

Certain embodiments of the invention relate to Angiotensin II receptor blockers or "ARBs" herein (also known as angiotensin receptor antagonists. $AT_1$-receptor antagonists, or sartans). ARBs are a group of pharmaceuticals which modulate the renin-angiotensin-aldosterone system by selectively inhibiting the effects of angiotensin II (Ang II), a peptide hormone that plays an important role in the pathophysiology of hypertension. ARBs antagonize the action of Ang II at the Ang II type 1 ($AT_1$) receptor and produce their blood pressure lowering effects by reversing the effects of Ang II, including, e.g., vasoconstriction, aldosterone release, ADH secretion, ACTH secretion, increased sodium absorption by the kidney, and catecholamine release. Losartan was the first ARB to be developed and approved by the United States Food and Drug Administration (FDA), and it has served as the basis for the development of other ARBs, including Azilsartan, Candesartan, Eprosartan, Irbesartan, Olmesartan, Telmisartan, and Valsartan, each of which is also approved by the FDA for clinical use.

Accordingly, ARBs can be used treat hypertension; however, ARBs can be prescribed for other indications, as well. For example, Losartan can also be used to reduce the risk of stroke in patients with hypertension and left ventricular hypertrophy and/or to treat diabetic nephropathy in patients with type 2 diabetes, an elevated serum creatinine and proteinuria, and a history of hypertension. Candesartan can be used in the treatment of heart failure in adults with left ventricular systolic dysfunction to reduce the risk of death and/or hospitalizations due to heart failure. Irbesartan is indicated for the treatment of diabetic nephropathy in patients with type 2 diabetes, hypertension, and an elevated serum creatinine and proteinuria. Telmisartan can be used to reduce the risk myocardial infarction, stroke, or death from cardiovascular causes in patients at high risk of developing major cardiovascular events. Valsartan can be used for the treatment of heart failure and used to reduce the risk of death in patients with left ventricular failure or left ventricular dysfunction following myocardial infarction. The benefits of ARB treatment has also been tested for a variety of other diseases and disorders, including, e.g., congestive heart failure, chronic heart failure, migraine, stroke, and renal disease (Gales et al. (2010) *Ann. Pharmacother.* 44 (2): 360-6; Irie et al. (2012) *Int J. Cardiol.* Published online Jul. 16, 2012; Kobori et al. (2012) *Curr Pharm Des.* Published online Nov. 21, 2012; Cancian et al. (2012) *Eur J Gen Pract.* Published on line Sep. 24, 2012). Each of the ARBs described above is known by a number of trade names, the most common of which are listed in Table 1 below.

TABLE 1

ARBs and Trade Names

| Drug | Trade Names |
|---|---|
| Azilsartan | Edarbi ® |
| Candesartan | Blopress ®, Atacand ® |
| Eprosartan | Teveten ® |
| Irbesartan | Avapro ® |
| Losartan | Cozaar ®, Anzar ®, Arbloc ®, Angisartan ® Hartzar ®, Pharex ®, Neosartan ®, Hyoerthree ®, Getzar ®, Kenzar ®, Lozaris ®, Qxar ®, Normoten ®, Ecozar ®, Lifezar ® |
| Olmesartan | Olmezar ®, Olmetec ® |
| Telmisartan | Micardis ®, Pritor ®, Benicar ® |
| Valsartan | Diovan ® |

In certain embodiments, methods described herein comprise administering an ARB, and compositions and kits described herein comprise an ARB. In certain embodiments, compositions and kits of the invention include any ARB, any combination of ARBs, or any prodrug, salt, or derivative of any ARB shown in Table 1.

Accordingly, in certain embodiments, the compositions of the invention include Losartan and an antigen, vaccine, or anti-tumor preparation, where the Losartan in the composition is at a concentration sufficient to provide a dose of at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, at least about 60 mg, at least about 70 mg, at least about 80 mg, of Losartan, including any range in between these values, or less than about 50 mg, or less than about 25 mg of Losartan, including any range in between these values. In certain embodiments, the Losartan in the composition is at a concentration sufficient to provide a dose of more than about 80 mg, more than about 100 mg, more than about 125 mg, more than about 150 mg, more than about 175 mg, or more than about 200 mg or Losartan, including any range in between about 5 mg and about 200 mg.

In certain embodiments, compositions of the invention can include Losartan at a concentration sufficient to provide a dose of at least about 0.5 mg/kg, at least about 0.75 mg/kg, at least about 1.0 mg/kg, at least about 1.25 mg·kg, at least about 1.5 mg/kg, at least about 1.75 mg/kg, or at least about 2.0 mg/kg of Losartan, including any range between about 0.5 mg/kg and about 1.75 mg/kg. In certain embodiments, compositions of the invention can include Losartan at a concentration sufficient to provide a dose of more than about 1.75 mg/kg, at least about 2.0 mg/kg, at least about 5 mg/kg, at least about 7 mg/kg, at least about 10 mg/kg, at least about 12 mg/kg, at least about 15 mg/kg, at least about 17 mg/kg, at least about 20 mg/kg, at least about 22 mg/kg, at least about 25 mg/kg, at least about 27 mg/kg, or at least about 30 mg/kg or Losartan, including any range in between about 1.75 mg/kg and about 30 mg/kg. In certain embodiments, the compositions of the invention can include Losartan at a concentration sufficient to provide a dose of more than about 30 mg/kg, e.g., at least about 35 mg/kg or at least about 40 mg/kg of Losartan, including any range in between about 30 mg/kg and about 40 mg/kg.

In certain embodiments, the invention provides compositions that can include Azilsartan and an antigen, vaccine, or anti-tumor preparation, where the Azilsartan in the composition is at a concentration sufficient to provide a dose of at least about 10 mg, at least about 20 mg, at least about 40 mg, at least about 60 mg, at least about 70 mg, at least about 80 mg, of Losartan, including any range in between these values, or less than about 50 mg, or less than about 80 mg, including any range between these values. In certain embodiments, the Azilsartan in the composition is at a concentration sufficient to provide a dose of more than about 80 mg, more than about 100 mg, more than about 120 mg, more than about 140 mg, or more than about 160 mg, including any range in between these values.

In certain embodiments, the invention also provides compositions that can include Candesartan and an antigen, vaccine, or anti-tumor preparation, where the Candesartan in the composition is at a concentration sufficient to provide a dose of at least about 0.5 mg, at least about 1 mg, at least about 2 mg, at least about 3 mg, or less than about 4 mg, including any range between these values. In certain embodiments, the Candesartan in the composition is at a concentration sufficient to provide a dose of more than about 32 mg, more than about 40 mg, more than about 48 mg, more than about 56 mg, more than about 64 mg or more than about 84 mg, including any range in between these values. In certain embodiments, the Candesartan in the composition is at a concentration sufficient to provide a dose of less than about 32 mg, less than about 40 mg, less than about 48 mg, less than about 56 mg, less than about 64 mg or less than about 84 mg, including any range in between these values.

In certain embodiments, certain compositions of the invention can include Eprosartan and an antigen, vaccine, or anti-tumor preparation, where the Eprosartan in the composition is at a concentration sufficient to provide a dose of at least about 50 mg, at least about 100 mg, at least about 200 mg, at least about 300 mg, at least about 400 mg, at least about 500 mg, at least about 600 mg, at least about 700 mg, at least about 800 mg, including any range between these values, or less than about 400 mg, less than about 300 mg, less than about 200 mg, or less than about 100 mg, including any range between these values. In certain embodiments, the Eprosartan in the composition is at a concentration sufficient to provide a dose of more than about 600 mg, more than about 750 mg, more than about 900 mg, more than about 1050 mg, or more than about 1200 mg, including any range in between these values.

In certain embodiments compositions of the invention can include Irbesartan and an antigen, vaccine, or anti-tumor preparation, where the Irbesartan in the composition is at a concentration sufficient to provide a dose of at least about 12.5 mg, at least about 25 mg, at least about 50 mg, at least about 75 mg, at least about 100 mg, at least about 125 mg, at least about 150 mg, at least about 175 mg, at least about 200 mg, at least about 250 mg, at least about 275 mg, or at least about 300 mg, including any range between these values, or less than about 150 mg, less than about 100 mg, less than about 50 mg, including any range between these values. In certain embodiments, the Irbesartan in the composition is at a concentration sufficient to provide a dose of more than about 300 mg, more than about 375 mg, more than about 450 mg, more than about 525 mg, or more than about 600 mg, including any range in between these values.

Alternatively, in other embodiments, compositions of the invention can include Olmesartan and an antigen, vaccine, or anti-tumor preparation, where the Olmesartan in the composition is at a concentration sufficient to provide a dose of at least about 5 mg, at least about 10 mg, at least about 15 mg, at least about 20 mg, at least about 25 mg, at least about 30 mg, at least about 35 mg, at least about 40 mg, including any range between these values, or less than about 20 mg, less than about 15 mg, less than about 10 mg including any range between these values. In certain embodiments, the Olmesartan in the composition is at a concentration sufficient to provide a dose of more than about 40 mg, more than about 50 mg, more than about 60 mg, more than about 70 mg, or more than about 40 mg, including any range in between these values.

In certain embodiments, compositions of the invention can include Telmisartan and an antigen, vaccine, or anti-tumor preparation, where the Telmisartan in the composition is at a concentration sufficient to provide a dose of at least about 5 mg, at least about 10 mg, at least about 15 mg, at least about 20 mg, at least about 25 mg, at least about 30 mg, at least about 35 mg, at least about 40 mg, including any range between these values, or less than about 20 mg, less than about 15 mg, less than about 10 mg, including any range between these values. In certain embodiments, the Telmisartan in the composition is at a concentration sufficient to provide a dose of more than about 80 mg, more than about 100 mg, more than about 120 mg, more than about 140 mg, or more than about 160 mg, including any range in between these values.

In certain embodiments, compositions of the invention can include Valsartan and an antigen, vaccine, or anti-tumor preparation, where the Valsartan in the composition is present at a concentration sufficient to provide a dose of at least about 5 mg, at least about 10 mg, at least about 15 mg, at least about 20 mg, at least about 25 mg, at least about 30 mg, at least about 35 mg, at least about 40 mg, including any range between these values, or less than about 20 mg, less than about 15 mg, less than about 10 mg, including any range between these values. In certain embodiments, the Valsartan in the composition is at a concentration sufficient to provide a dose of more than about 320 mg, more than about 400 mg, more than about 480 mg, more than about 560 mg, or more than about 640 mg, including any range in between these values.

In some embodiments, the compositions comprise a mixture of 2 or more ARBs. In some aspects, the compositions may comprise about 2 to about 8, or about 2 to about 6, or about 2 to about 4, or 1, 2, 3, 4, 5, 6, 7, 8 or more ARBs as described herein. In some embodiments, methods of the present invention comprise administering 2 or more ARBs. In some aspects the methods comprise administering about 2 to about 8, or about 2 to about 6, or about 2 to about 4, or 1, 2, 3, 4, 5, 6, 7, 8 or more ARBs as described herein. Typically. ARBs are supplied in the form of tablets for oral administration. ARBs each exhibit different pharmacokinetic properties. For example, as shown below in Table 2, the biological half-lives and the bioavailability of ARBs vary widely, with Losartan having the lowest in vivo half-life.

TABLE 2

Comparison of ARB Pharmacokinetics

| Drug | Biological Half-Life | Bioavailability |
| --- | --- | --- |
| Azilsartan | 11 hours | 60% |
| Candesartan | 9 hours | 15% |
| Eprosartan | 5 hours | 13% |
| Irbesartan | 11-15 hours | 70% |
| Losartan | 2 hours | 33% |
| Olmesartan | 14-16 hours | 29% |
| Telmisartan | 24 hours | 42-58% |
| Valsartan | 6 hours | 25% |

Following administration (e.g., oral or otherwise), the presence and/or the levels of an ARB (or of its metabolites) can be detected in an individual's blood or urine using methods well known to those of skill in the art, including, for example, chromatographic and/or spectroscopic techniques. Details regarding such techniques are described in, e.g., Nakashima et al. (1996) *Blood Press. Suppl.* 2: 62-66; Sica et al. (2005) *Clin. Pharmacokinet.* 44(8): 797-814; Lu et al. (2011) *J. Pharm. Biomed. Anal.* 54(1): 100-105; Yeung et al. (2000) *Int. J. Pharmaceut.* 204: 17-22; Chando et al. (1998) *Drug Metab. Dispos.* 26(5): 408-417; McCarthy et al. (1998) *J. Pharm Biomed. Anal.* 17: 671-677; Ferreirós et al. (2007) *Ther. Drug Monitoring* 29(6): 824-834; González et al. (2002) *J. Chromatography A* 949: 49-60; and others.

Compounds of Formula (I)-(V)

Certain embodiments of the invention relate to compounds of any one of Formulae (I)-(V). In certain embodiments, methods described herein comprise administration of compositions comprising a compound of any one of Formulae (I)-(V), and compositions and kits described herein comprise a compound of any one of Formulae (I)-(V). Formulae (I)-(V) are described below.

Formula (I)

The present disclosure provides a compound of Formula (I) and compositions comprising a compound of Formula (I):

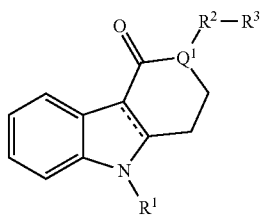

(I)

wherein $R^1$ is hydrogen or $C_{1-6}$ alkyl;

--- is a single bond or double bond;

$Q^1$ is N or CH;

$R^2$ is selected from hydrogen and $C_{1-6}$ alkylene, wherein one carbon unit of said alkylene is optionally replaced with —O—, —S—, —SO—, —SO$_2$—, —NR$^a$—, or —CO—; wherein $R^a$ is hydrogen or $C_{1-6}$ alkyl; and $R^3$ is hydrogen or an optionally substituted 5-membered heteroaryl ring; wherein the heteroaryl ring is optionally substituted with $C_{1-6}$ alkyl;

or pharmaceutically acceptable salts thereof.

In some embodiments of Formula (I), $R^1$ is hydrogen. In some embodiments, $R^1$ is $C_{1-6}$ alkyl. In some embodiments, $R^1$ is methyl or ethyl. In some embodiments, $R^1$ is methyl.

In some embodiments of Formula (I), --- is a single bond. In some embodiments, --- is a double bond.

In some embodiments of Formula (I), $Q^1$ is N. In some embodiments, $Q^1$ is CH.

In some embodiments of Formula (I), $R^2$ is hydrogen. In some embodiments, $R^2$ is a $C_{1-6}$ alkylene, such as $C_1$ alkylene, $C_2$ alkylene, $C_3$ alkylene, $C_4$ alkylene, $C_5$ alkylene, or $C_6$ alkylene. In some embodiments, $R^2$ is a $C_1$ alkylene. In some embodiments, $R^2$ is $C_{1-6}$ alkylene, wherein one carbon unit of said alkylene is replaced with —O—, —S—, —SO—, —SO$_2$—, —NR$^a$—, or —CO—; wherein $R^a$ is hydrogen or $C_{1-6}$ alkyl. In some embodiments, $R^2$ is $C_{1-6}$ alkylene, wherein one carbon unit of said alkylene is replaced with —O—, —S—, —SO—, or —SO$_2$—. In some embodiments, $R^2$ is $C_{1-6}$ alkylene, wherein one carbon unit of said alkylene is replaced with —NR$^a$—; wherein $R^a$ is hydrogen or $C_{1-6}$ alkyl. In some embodiments, $R^2$ is $C_{1-6}$ alkylene, wherein one carbon unit of said alkylene is replaced with —CO—.

In some embodiments of Formula (I), $R^3$ is hydrogen. In some embodiments, $R^3$ is an optionally substituted 5-membered heteroaryl ring; wherein the heteroaryl ring is optionally substituted with $C_{1-6}$ alkyl. In some embodiments, $R^3$ is an optionally substituted 5-membered heteroaryl ring containing one, two, three, or four heteroatoms. In certain instances, the $R^3$ heteroaryl ring contains one heteroatom. In certain instances, the $R^3$ heteroaryl ring contains two heteroatoms. In certain instances, the $R^3$ heteroaryl ring contains three heteroatoms. In certain instances, the $R^3$ heteroaryl ring contains four heteroatoms. In certain instances, the $R^3$ heteroaryl ring contains at least one heteroatom selected from nitrogen, sulfur, and oxygen. In certain instances, the $R^3$ heteroaryl ring contains two heteroatoms selected from nitrogen, sulfur, and oxygen. In certain instances, the $R^3$ heteroaryl ring contains two nitrogen heteroatoms. In certain instances, the $R^3$ heteroaryl ring contains carbon, nitrogen, and sulfur ring members. In certain instances, the $R^3$ heteroaryl ring contains carbon and nitrogen ring members. In certain instances, the $R^3$ heteroaryl ring contains carbon, nitrogen, and oxygen ring members.

In certain instances, the $R^3$ heteroaryl ring is furanyl, thiophenyl, pyrrolyl, oxazolyl, thiazolyl, imidazolyl, thiadiazolyl, oxadiazolyl, triazolyl, or tetrazolyl, each optionally substituted with $C_{1-6}$alkyl, as described for the $R^3$ heteroaryl ring. In certain instances, the $R^3$ heteroaryl ring is selected from the following:

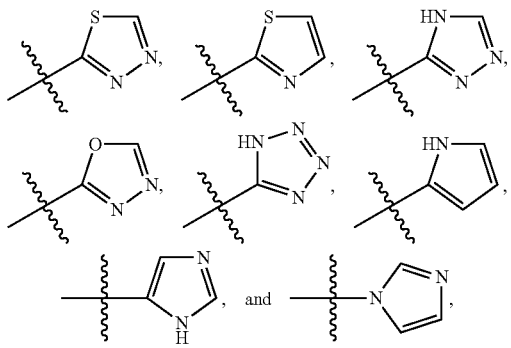

each optionally substituted with $C_{1-6}$ alkyl, as described for the $R^3$ heteroaryl ring. In certain instances, the $R^3$ heteroaryl ring is

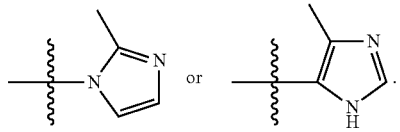

Formula (II)

The present disclosure provides a compound of Formula (II) and compositions comprising a compound of Formula (II):

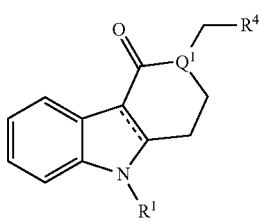

(II)

wherein $R^1$ is hydrogen or $C_{1-6}$ alkyl;

--- is a single bond or double bond;

$Q^1$ is N or CH; and $R^4$ is an optionally substituted 5-membered heteroaryl ring; wherein the heteroaryl ring is optionally substituted with $C_{1-6}$ alkyl;

or pharmaceutically acceptable salts thereof.

In some embodiments of Formula (II), $R^1$ is hydrogen. In some embodiments, $R^1$ is $C_{1-6}$ alkyl. In some embodiments, $R^1$ is methyl or ethyl. In some embodiments, $R^1$ is methyl.

In some embodiments of Formula (II), ⸺ is a single bond. In some embodiments, ⸺ is a double bond.

In some embodiments of Formula (II), $Q^1$ is N. In some embodiments, $Q^1$ is CH.

In some embodiments of Formula (II), $R^4$ is an optionally substituted 5-membered heteroaryl ring; wherein the heteroaryl ring is optionally substituted with $C_{1-6}$alkyl. In some embodiments, $R^4$ is an optionally substituted 5-membered heteroaryl ring containing one, two, three, or four heteroatoms. In certain instances, the $R^4$ heteroaryl ring contains one heteroatom. In certain instances, the $R^4$ heteroaryl ring contains two heteroatoms. In certain instances, the $R^4$ heteroaryl ring contains three heteroatoms. In certain instances, the $R^4$ heteroaryl ring contains four heteroatoms. In certain instances, the $R^4$ heteroaryl ring contains at least one heteroatom selected from nitrogen, sulfur, and oxygen. In certain instances, the $R^4$ heteroaryl ring contains two heteroatoms selected from nitrogen, sulfur, and oxygen. In certain instances, the $R^4$ heteroaryl ring contains two nitrogen heteroatoms. In certain instances, the $R^4$ heteroaryl ring contains carbon, nitrogen, and sulfur ring members. In certain instances, the $R^4$ heteroaryl ring contains carbon and nitrogen ring members. In certain instances, the $R^4$ heteroaryl ring contains carbon, nitrogen, and oxygen ring members.

In certain instances, the $R^4$ heteroaryl ring is furanyl, thiophenyl, pyrrolyl, oxazolyl, thiazolyl, imidazolyl, thiadiazolyl, oxadiazolyl, triazolyl, or tetrazolyl, each optionally substituted with $C_{1-6}$ alkyl, as described for the $R^4$ heteroaryl ring. In certain instances, the $R^4$ heteroaryl ring is selected from the following:

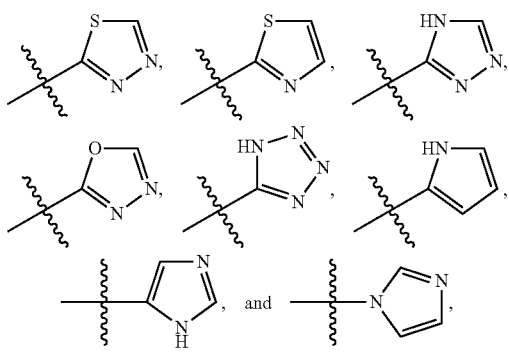

each optionally substituted with $C_{1-6}$alkyl, as described for the $R^3$ heteroaryl ring. In certain instances, the $R^4$ heteroaryl ring is

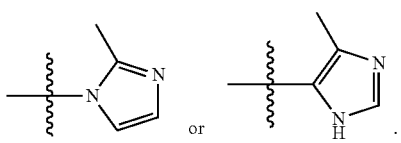

Formula (III)

The present disclosure provides a compound of Formula (III) and compositions comprising a compound of Formula (III):

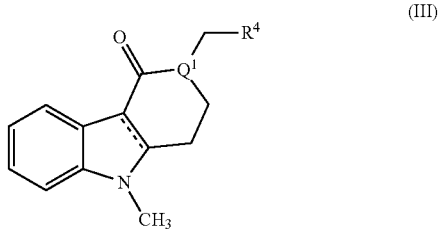

wherein
⸺ is a single bond or double bond;
$Q^1$ is N or CH; and
$R^4$ is an optionally substituted 5-membered heteroaryl ring; wherein the heteroaryl ring is optionally substituted with $C_{1-6}$ alkyl;
or pharmaceutically acceptable salts thereof.

In some embodiments of Formula (III), ⸺ is a single bond. In some embodiments, ⸺ is a double bond.

In some embodiments of Formula (III), $Q^1$ is N. In some embodiments, $Q^1$ is CH.

In some embodiments of Formula (III), $R^4$ is an optionally substituted 5-membered heteroaryl ring; wherein the heteroaryl ring is optionally substituted with $C_{1-6}$alkyl. In some embodiments, $R^4$ is an optionally substituted 5-membered heteroaryl ring containing one, two, three, or four heteroatoms. In certain instances, the $R^4$ heteroaryl ring contains one heteroatom. In certain instances, the $R^4$ heteroaryl ring contains two heteroatoms. In certain instances, the $R^4$ heteroaryl ring contains three heteroatoms. In certain instances, the $R^4$ heteroaryl ring contains four heteroatoms. In certain instances, the $R^4$ heteroaryl ring contains at least one heteroatom selected from nitrogen, sulfur, and oxygen. In certain instances, the $R^4$ heteroaryl ring contains two heteroatoms selected from nitrogen, sulfur, and oxygen. In certain instances, the $R^4$ heteroaryl ring contains two nitrogen heteroatoms. In certain instances, the $R^4$ heteroaryl ring contains carbon, nitrogen, and sulfur ring members. In certain instances, the $R^4$ heteroaryl ring contains carbon and nitrogen ring members. In certain instances, the $R^4$ heteroaryl ring contains carbon, nitrogen, and oxygen ring members.

In certain instances, the $R^4$ heteroaryl ring is furanyl, thiophenyl, pyrrolyl, oxazolyl, thiazolyl, imidazolyl, thiadiazolyl, oxadiazolyl, triazolyl, or tetrazolyl, each optionally substituted with $C_{1-6}$alkyl, as described for the $R^4$ heteroaryl ring. In certain instances, the $R^4$ heteroaryl ring is selected from the following:

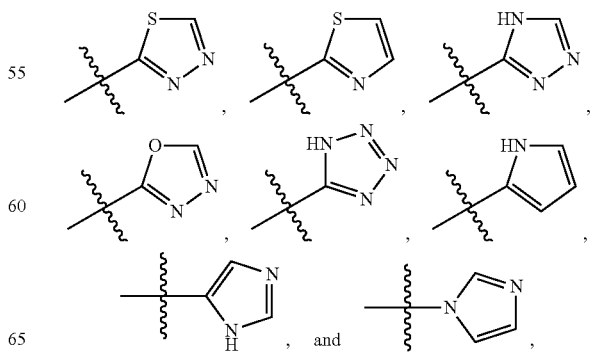

each optionally substituted with $C_{1-6}$alkyl, as described for the $R^3$ heteroaryl ring. In certain instances, the $R^4$ heteroaryl ring is

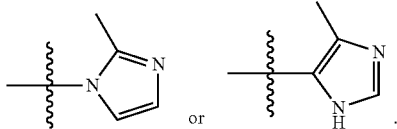

Formula (IV)

The present disclosure provides a compound of Formula (IV) and compositions comprising a compound of Formula (IV):

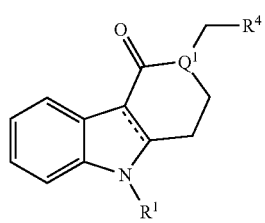

(IV)

wherein
$R^1$ is hydrogen or $C_{1-6}$ alkyl;
⸺ is a single bond or double bond;
$Q^1$ is N or CH; and
$R^4$ is selected from

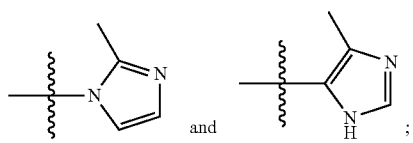

or pharmaceutically acceptable salts thereof.

In some embodiments of Formula (IV), $R^1$ is hydrogen. In some embodiments, $R^1$ is $C_{1-6}$ alkyl. In some embodiments, $R^1$ is methyl or ethyl. In some embodiments, $R^1$ is methyl.

In some embodiments of Formula (IV), ⸺ is a single bond. In some embodiments, ⸺ is a double bond.

In some embodiments of Formula (IV), $Q^1$ is N. In some embodiments, $Q^1$ is CH.

In some embodiments of Formula (IV), $R^4$ is

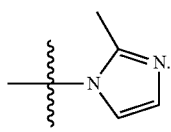

In some embodiments, $R^4$ is

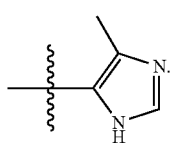

Formula (V)

The present disclosure provides a compound of Formula (V) and compositions comprising a compound of Formula (V):

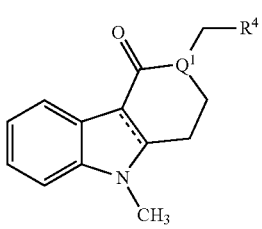

(V)

wherein
⸺ is a single bond or double bond;
$Q^1$ is N or CH; and
$R^4$ is selected from

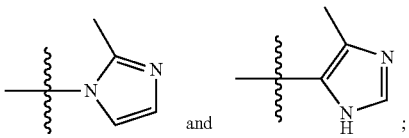

or pharmaceutically acceptable salts thereof.

In some embodiments of Formula (V), ⸺ is a single bond. In some embodiments, ⸺ is a double bond.

In some embodiments of Formula (V), $Q^1$ is N. In some embodiments, $Q^1$ is CH.

In some embodiments of Formula (V), $R^4$ is

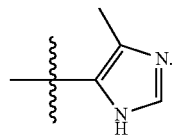

In some embodiments, $R^4$ is

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Particular compounds of interest are shown below:

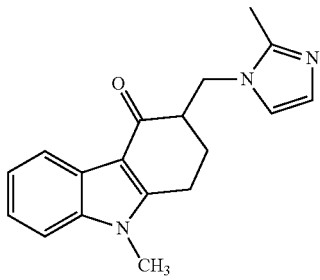 [SMILES: Cc1nccn1CC1CCc2c(c3ccccc3n2C)C1=O]

Ondansetron 9-methyl-3-((2-methyl-1H-imidazol-1-yl)methyl)-2,3-dihydro-1H-carbazol-4(9H)-one

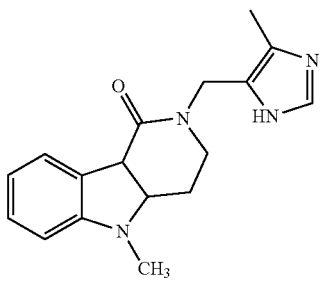 [SMILES: Cc1nc[nH]c1CN1CCC2C(C1=O)c1ccccc1N2C]

Alosetron 5-methyl-2-((4-methyl-1H-imidazol-5-yl)methyl)-2,3,4,4a,5,9b-hexahydro-1H-pyrido[4,3-b]indol-1-one Alosetron can be used in the management of severe diarrhea-predominant irritable bowel syndrome (IBS). Ondansetron can be prescribed to treat and/or prevent chemotherapy-induced nausea and vomiting (CINV). Ondansetron has been indicated in the prevention and treatment of radiation-induced nausea and vomiting (RINV), and post-operative nausea and vomiting (PONV). The benefits of Ondansetron treatment have also been tested for a variety of other diseases and disorders, including, e.g., motion sickness (Levine et al. (2000) Aviat Space Environ Med. 71: 1111-1114; Muth et al. (2007) Aviat Space Environ Med. 78: 686-92); lesional vestibular disorder (European Patent Application No. 2432467 A1 and US Patent Application Publication 2012/0064094); anti-psychotic induced tardive dyskinesia in people with schizophrenia (Zullino et al. (2001) Am. J. Psychiatry 158: 657-8 and Sirota et al. (2000) Am. J. Psychiatry 157: 287-289); and schizophrenia (Zhang et al. (2006) Schiz Res 88: 102-110). Other medical conditions that may be treated using ondansetron include, e.g., gastroenteritis, pediatric gastroenteritis, opioid-induced nausea, nausea and vomiting of pregnancy, and obsessive-compulsive disorder (Broocks et al. (1998) Psychiatry Res. 79: 11-20).

Ondansetron and Alosetron are each known by a number of trade names, the most common of which are listed in Table 3 below.

TABLE 3

| Trade Names | |
|---|---|
| Trade Names | |
| Alosetron | Lotronex ® |
| Ondansetron | Doran ®, Lupisetron ®, Mylan˜Ondansetron, Myset ®, Ranidom ®, Vomicare ®, Vomiven ®, Zofran ®, Zofran ODT ®, Zuplenz ® |

Accordingly, in certain embodiments, the compositions of the invention include Ondansetron and an antigen, vaccine, or anti-tumor preparation. In certain embodiments, the composition is administered orally. In certain embodiments, Ondansetron in the orally administered composition is at a concentration sufficient to provide a dose of at least about 0.5 mg, at least about 1 mg, at least about 2 mg, at least about 3 mg, at least about 4 mg, at least about 5 mg, at least about 6 mg, at least about 7 mg, at least about 8 mg, at least about 10 mg, or less than about 12 mg, or less than about 18 mg, or less than about 24 mg of Ondansetron, including any range in between these values. In certain embodiments, the Ondansetron in the orally administered composition is at a concentration sufficient to provide a dose of more than about 24 mg, more than about 26 mg, more than about 28 mg, more than about 30 mg, more than about 32 mg, or more than about 34 mg Ondansetron, including any range in between these values.

In certain embodiments, compositions of the invention are administered intravenously. In certain embodiments, compositions for intravenous administration can include Ondansetron at a concentration sufficient to provide a dose of at least about 0.5 mg/kg/day, at least about 0.75 mg/kg/day, at least about 1.0 mg/kg/day, at least about 1.5 mg/kg/day, at least about 2.0 mg/kg/day, at least about 2.5 mg/kg/day, at least about 3.0 mg/kg/day, at least about 3.5 mg/kg/day, at least about 4.0 mg/kg/day, at least about 4.5 mg/kg/day, at least about 5.0 mg/kg/day, at least about 5.5 mg/kg/day, at least about 6.0 mg/kg/day, at least about 6.5 mg/kg/day, at least about 7.0 mg/kg/day, at least about 7.5 mg/kg/day, at least about 8.0 mg/kg/day, or less than about 8.5 mg/kg/day of Ondansetron, including any range between these values.

In certain embodiments, the invention provides compositions that can include Alosetron and an antigen, vaccine, or anti-tumor preparation, where the Alosetron in the composition is at a concentration sufficient to provide a dose of at least about 0.1 mg, at least about 0.2 mg, at least about 0.3 mg, at least about 0.4 mg, at least about 0.6 mg, at least about 0.8 mg, at least about 0.9 mg, at least about 1 mg, including any range between these values, or less than about 0.5 mg or less than about 0.7 mg or less than about 0.9 mg, or less than about 1 mg of Alosetron, including any range between these values. In certain embodiments, the Alosetron in the composition is at a concentration sufficient to provide a dose of more than about 2 mg, more than about 3 mg, more than about 4 mg, more than about 5 mg, or more than about 6 mg Alosetron, including any range in between these values.

Ondansetron and Alosetron are supplied in the form of tablets or solutions for oral administration. In one embodiment, Ondansetron is also supplied in solution form for parenteral administration. Ondansetron and Alosetron each exhibit different pharmacokinetic properties. For example, the biological half-life of Alosetron is about 1.5 to about 1.7 hours, and the biological half-life of Ondansetron is about 3.9 hours.

Following administration (e.g., oral, intramuscular, subcutaneous, or otherwise), the presence and/or the levels of a compound of Formula (I) (or of its metabolites) can be detected in an individual's blood or urine using methods well known to those of skill in the art, including, for example, chromatographic and/or spectroscopic techniques. Details regarding such techniques are described in, e.g., Somers et al. (2007) Xenobiotica 37: 855-869; Koch et al. (2002) Br J Clin Pharmacol. 53: 238-242; Xu et al. (2000) J Mass Spectrom 35: 1329-1334; Roila et al. (1995) Clin Pharmacokinet 29: 95-103; and others.

Antigens

In certain embodiments, compositions and kits of the invention include an antigen, and certain methods of the invention comprise administering an antigen. In certain embodiments, the antigen present in the compositions provided by the invention can be any material or substance that can induce an immune response (i.e., cellular and/or humoral immune response) by the immune system of a human or animal. For example, the antigen can be a polypeptide of interest derived from an infectious agent, e.g., a bacterium, a virus, a fungus, a protozoan, a parasite, or a prion. In particular embodiments, the antigen can be a whole microbe or a mixture thereof, and the compositions can include a live whole infectious agent. In certain embodiments, the compositions can include a killed or inactivated (attenuated) infectious agent.

In certain embodiments, the antigen comprises, e.g., a polypeptide, nucleic acid, polysaccharide, a fatty acid or the like, derived from an infectious agent. In certain embodiments, the antigen can be a subunit or fragment of a polypeptide, or a fragment of a nucleic acid or polysaccharide derived from an infectious agent. In certain embodiments, the antigen is a recombinant polypeptide produced in a heterologous expression system, e.g., a recombinant protein derived from an infectious agent that was expressed in and purified from cells of another organism. However, in particular embodiments, an antigen can also be a recombinant nucleic acid construct which encodes a polypeptide antigen of interest (e.g., an expression construct). In certain embodiments, the antigen can comprise a viral subunit, a virus-like particle, a capsular (poly) saccharide; a bacterial outer membrane bleb formation containing one or more of bacterial outer membrane proteins, a phospholipid, a lipopolysaccharide, or a polysaccharide.

In certain embodiments, the antigen can be a naturally occurring substance. In certain embodiments, the antigen comprises or is derived from an allergen, e.g., pollen. In certain embodiments, the antigen comprises or is derived from a toxin. In certain embodiments, the antigen comprises or is derived from an addictive substance, including, without limitation, nicotine, caffeine, alcohol, and the like. In certain embodiments, the antigen can be a non-naturally occurring (i.e., synthetic) substance, e.g., a synthetic peptide, a synthetic polysaccharide, or a synthetic polymer.

In certain embodiments, the antigen can be provided in a vaccine, e.g., any vaccine known in the art. For example, the vaccine can be a nucleic acid construct (e.g., a DNA vaccine) or the vaccine can be a viral vector vaccine, which uses live viruses to carry DNA into an individual's cells. The DNA contained in the viral vaccine encodes antigen(s) that, once expressed in the infected cells, elicit an immune response. Alternatively, in certain embodiments, the vaccine can be a subunit vaccine, e.g., a specific protein from a virus. In certain embodiments, the vaccine can be a dendritic cell vaccine, in which an individual's dendritic cells are cultured with an antigen and then re-injected into the individual to stimulate an immune response. In certain embodiments, the vaccine can be a monovalent vaccine, i.e., containing a single antigen. In certain embodiments, the vaccine containing the antigen is a polyvalent or multivalent vaccine, i.e., containing more than one antigen.

Pharmaceutically Acceptable Compositions and Formulations

The compositions or formulations of the present invention include any composition or formulation described herein. The various compounds (e.g., the ARBs, the compounds of Formulae (I)-(V), the antigens, the vaccines, and the antitumor compositions) described herein may be present in various compositions or formulations, including those suitable for administration to an individual (e.g., pharmaceutical compositions). In some embodiments, a composition of the present invention includes any one of the combinations of compounds listed in Table 4, herein. The compositions of the invention can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers or diluents, which are defined as vehicles commonly used to formulate pharmaceutical compositions for animal or human administration. The carrier or diluent is selected so as not to affect the biological activity of the combination. Examples of such carriers or diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

For oral administration, the compositions of the invention can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include, e.g., aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Kits

The invention also provides kits and articles of manufacture comprising compositions described herein for use in the methods of enhancing an immune response, decreasing recruitment of monocytes to a lymph node, amplifying vaccine immunity, and inhibiting tumor growth and metastasis. In certain embodiments, kits of the invention include a container or compartment comprising a compound of Formula (I):

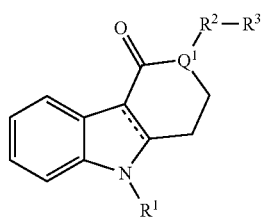

(I)

wherein $R^1$ is hydrogen or $C_{1-6}$alkyl;

═══ is a single bond or double bond;

$Q^1$ is N or CH;

$R^2$ is selected from hydrogen and $C_{1-6}$ alkylene, wherein one carbon unit of said alkylene is optionally replaced with —O—, —S—, —SO—, —SO$_2$—, —NR$^a$—, or —CO—; wherein $R^a$ is hydrogen or $C_{1-6}$ alkyl; and $R^3$ is hydrogen or an optionally substituted 5-membered heteroaryl ring; wherein the heteroaryl ring is optionally substituted with $C_{1-6}$alkyl;

or pharmaceutically acceptable salts thereof, and an antigen, a vaccine, or anti-tumor preparation. In certain embodiments, the kit includes Ondansetron. In certain embodiments, the kit includes Alosetron. In certain embodiments, kits of the invention provide the compound of Formula (I) (e.g., Ondansetron and/or Alosetron) in a first container or compartment and the antigen, vaccine, or anti-tumor preparation in a second container or compartment.

In certain embodiments, kits of the invention include a container or compartment comprising an ARB and an antigen, a vaccine, or anti-tumor preparation. In certain embodiments, kits of the invention provide the ARB in a first container or compartment and the antigen, vaccine, or anti-tumor preparation in a second container or compartment.

In certain embodiments, the kits of the invention comprise a single container comprising both a compound of Formula (I) (e.g., Ondansetron and/or Alosetron) and an antigen, vaccine, or anti-tumor preparation. In certain embodiments, the kits of the invention comprise a single container comprising both an ARB and an antigen, vaccine, or anti-tumor preparation. In one embodiment, the kit of the invention comprises Losartan and a tyrosine kinase inhibitor.

In one certain embodiment, a kit of the invention comprises a container comprising a composition (e.g., a pharmaceutically acceptable composition or formulation) comprising both a Compound of Formula (I) and an antigen, vaccine, or anti-tumor preparation.

In one certain embodiment, a kit of the invention comprises a container comprising a composition (e.g., a pharmaceutically acceptable composition or formulation) comprising both an ARB and an antigen, vaccine, or anti-tumor preparation.

In particular embodiments, the combination of (i) ARB or Compound of Formula (I) and (ii) antigen, vaccine or anti-tumor preparation, present in a kit or composition of the present invention (including compositions present within a kit of the present invention) is selected from any of the combinations listed in Table 4 below. In one certain embodiment, the kit of the invention comprises at least two separate containers, with each separate container comprising at least one of two separate compositions (e.g., pharmaceutically acceptable compositions or formulations), wherein a first of the two compositions comprises an ARB or a Compound of Formula (I) and the second of the two separate compositions comprises an antigen, vaccine, or anti-tumor preparation. In particular embodiments, the combination of the first and the second compositions is selected from any one of the combinations listed in Table 4.

TABLE 4

Combinations of monocyte migration inhibitors with antigens, vaccines, or anti-tumor preps

| Column A: Combination Number | Column B: ARB or Compound of Formula (I) | Column C: Antigen, Vaccine, or Anti-tumor preparation |
|---|---|---|
| 1 | Ondansetron | Antigen |
| 2 | Ondansetron | Vaccine |
| 3 | Ondansetron | Anti-tumor preparation |
| 4 | Ondansetron | Sunitinib |
| 5 | Alosetron | Antigen |
| 6 | Alosetron | Vaccine |
| 7 | Alosetron | Anti-tumor preparation |
| 8 | Alosetron | Antigen |
| 9 | Azilsartan | Antigen |
| 10 | Azilsartan | Vaccine |
| 11 | Azilsartan | Anti-tumor preparation |
| 12 | Azilsartan | Sunitinib |
| 13 | Candesartan | Antigen |
| 14 | Candesartan | Vaccine |
| 15 | Candesartan | Anti-tumor preparation |
| 16 | Candesartan | Sunitinib |
| 17 | Eprosartan | Antigen |
| 18 | Eprosartan | Vaccine |
| 19 | Eprosartan | Anti-tumor preparation |
| 20 | Eprosartan | Sunitinib |
| 21 | Irbesartan | Antigen |
| 22 | Irbesartan | Vaccine |
| 23 | Irbesartan | Anti-tumor preparation |
| 24 | Irbesartan | Sunitinib |
| 25 | Losartan | Antigen |
| 26 | Losartan | Vaccine |
| 27 | Losartan | Anti-tumor preparation |
| 28 | Losartan | Sunitinib |
| 29 | Olmesartan | Antigen |
| 30 | Olmesartan | Vaccine |
| 31 | Olmesartan | Anti-tumor preparation |
| 32 | Olmesartan | Sunitinib |
| 33 | Telmisartan | Antigen |
| 34 | Telmisartan | Vaccine |
| 35 | Telmisartan | Anti-tumor preparation |
| 36 | Telmisartan | Sunitinib |
| 37 | Valsartan | Antigen |
| 38 | Valsartan | Vaccine |
| 39 | Valsartan | Anti-tumor preparation |
| 40 | Valsartan | Sunitinib |

In certain embodiments, the kits of the invention further comprise instructions for use in accordance with any of the methods described herein.

Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of the compositions described herein generally include information as to dosage, dosing schedule, and route of administration for the intended treatment. In some embodiments, the instructions comprise instructions for administering an ARB or a compound of Formula (I) (e.g., Ondansetron and/or Alosetron) in conjunction with an antigen, a vaccine, or an anti-tumor preparation. Kits of the invention may further comprise a description of selecting an individual suitable or treatment.

The present invention also provides kits comprising an ARB, a compound of Formula (I), or a compositions described herein and further comprising instruction(s) on methods of using the composition or kit, such as uses further described herein. The kit may comprise one or more unit dosages of an ARB, a compound of Formula (I), or a composition described herein. The kit may contain instructions for administering the ARB or the compound of Formula (I) (e.g., Ondansetron and/or Alosetron) and the antigen, vaccine, or anti-tumor preparation simultaneously or sequentially, as described elsewhere herein. In some embodiments, the kit of the invention comprises the packaging described herein. In other embodiments, the kit of the invention comprises the packaging described herein and a second packaging comprising a buffer. The kit may further include other materials desirable from a commercial and user standpoint, including other buffers, diluents, filters, needles, syringes, and package inserts with instructions for performing any methods described herein.

In certain embodiments, kits may also include multiple unit doses of an ARB or a compound of Formula (I) (e.g., Ondansetron and/or Alosetron) and an antigen, a vaccine, or an anti-tumor preparation and instructions for use and packaged in quantities sufficient for storage and use in pharmacies, for example, hospital pharmacies and compounding pharmacies. In certain embodiments, the kits of the invention are in suitable packaging. Suitable packaging includes, but is not limited to, vials, bottles, jars, flexible packaging (e.g., sealed Mylar or plastic bags), and the like. In certain embodiments, a container or compartment is vials, bottles, jars, flexible packaging (e.g., sealed mylar or plastic bags), and the like. Kits may optionally provide additional components such as buffers and interpretative information.

Methods of Enhancing an Immune Response Against an Antigen in an Individual

A vaccine can be administered to an individual to elicit an immune response that can lessen the severity and/or duration of a disease or infection. Vaccines can include antigens. However, not all antigens are capable of stimulating a sufficiently robust B cell and/or T cell response to produce protective immunity. Certain individuals, for example, children, the elderly, or the immunocompromised, may not be capable of mounting a robust immune response. The methods and compositions described herein can be used to enhance an immune response in an individual to whom an antigen has been administered. Such methods/uses include administering a composition containing the antigen to the individual in conjunction with an ARB or a compound of Formula (I) (e.g., Ondansetron and/or Alosetron).

Accordingly, in one embodiment, the present invention includes a method of enhancing an immune response to an antigen in an individual, comprising administering to the individual an antigen and an ARB. In another embodiment, the present invention includes a method of enhancing an immune response to an antigen in an individual, comprising administering to the individual an antigen and a compound of Formula (I). In certain embodiments, the ARB or compound of formula (I) are administered in an effective amount, e.g., an amount sufficient to enhance the immune response to the antigen. In particular embodiments, the antigen, the ARB and/or the compound of Formula (I) are present in one or more composition, e.g., one or more pharmaceutical compositions. In certain embodiments, the methods include administering a composition containing the antigen to the individual with Ondansetron. In certain embodiments, the methods include administering a composition containing the antigen to the individual with Alosetron. In certain embodiments, the methods include administering a composition containing the antigen to the individual in conjunction with an ARB (e.g., Losartan, Candesartan, Eprosartan, Irbesartan, Olmesartan, Telmimsartan, Azilsaran, and/or Valsartan).

The compound of Formula (I) administered in conjunction with the antigen can be any compound, combination of compounds, or any prodrug, salt, or derivative of a compound described herein. The ARB administered in conjunction with the antigen can be any ARB, combination of ARBs, or any prodrug, salt, or derivative of an ARB described herein. The antigen administered in conjunction with the ARB or the compound of Formula (I) (e.g., Ondansetron or Alosetron) can be any antigen described herein.

In certain embodiments, the combination of antigen and ARB or compound of Formula (I) is any described herein (e.g., any ARB described herein combined with any antigen described herein; or e.g., any compound of Formula (I) described herein combined with any antigen described herein). The ARB or the compound of Formula (I) (e.g., Ondansetron or Alosetron) and the antigen can be present in a single pharmaceutical composition, or they can be provided in separate compositions that can be administered in any order relative to one another or administered simultaneously, as described herein. Compositions containing the ARB or the compound of Formula (I) (e.g., Ondansetron or Alosetron) and/or the antigen can be administered according to any method known in the art at dosages described elsewhere herein.

In certain embodiments, the individuals to whom a compound of Formula (I) can be administered in conjunction with the antigen can be those who are otherwise not receiving the Ondansetron or Alosetron for the treatment of, e.g., irritable bowel syndrome (IBS), post-operative nausea and vomiting (PONV), chemotherapy-induced nausea and vomiting (CINV), radiation-induced nausea and vomiting (RINV), and/or other conditions, as described herein. In some embodiments, an individual who has a condition or disease described herein, or is otherwise in need of treatment, can receive Ondansetron and/or Alosetron in conjunction with an antigen for the purpose of enhancing an immune response if the individual is not being treated with Ondansetron and/or Alosetron. Alternatively, in other embodiments, the individuals to whom a compound of Formula (I) is administered in conjunction with the antigen can be those who have temporarily suspended Ondansetron and/or Alosetron treatment and have been shown, using methods well known in the art, to not have detectable levels of Ondansetron and/or Alosetron in their blood and/or urine prior to the administration of the Ondansetron and/or Alosetron in conjunction with the antigen. Details regarding such techniques are described in, e.g., Somers et al. (2007) Xenobiotica 37: 855-869; Koch et al. (2002) Br J Clin Pharmacol. 53: 238-242; Xu et al. (2000) J Mass Spectrom 35: 1329-1334; Roila et al. (1995) Clin Pharmacokinet 29: 95-103; and others.

In certain embodiments, the individuals to whom an ARB is administered in conjunction with an antigen can be those who are otherwise not receiving an ARB for treatment of a pre-existing condition, e.g., hypertension, diabetic nephropathy, heart failure, and/or other conditions, as described herein. In some embodiments, an individual who has a condition or disease described herein, or who is otherwise in need of treatment, can receive an ARB in conjunction with an antigen for the purpose of enhancing an immune response if the individual is not being treated with an ARB. Alternatively, in certain embodiments, the individuals to whom an ARB is administered in conjunction with an antigen can be those who have temporarily suspended ARB treatment and have been shown, using methods well known in the art, to not have detectable levels of an ARB in their blood and/or urine prior to the administration of the ARB in conjunction with the antigen. Details regarding such techniques are described in, e.g., Nakashima et al. (1996) Blood Press. Suppl. 2: 62-66; Sica et al. (2005) Clin. Pharmacokinet. 44(8): 797-814; Lu et al. (2011) J. Pharm. Biomed. Anal. 54(1): 100-105; Yeung et al. (2000) Int. J. Pharmaceut. 204: 17-22; Chando et al. (1998) Drug Metab. Dispos. 26(5): 408-417; McCarthy et al. (1998) J. Pharm Biomed. Anal. 17: 671-677; Ferreirós et al. (2007) Ther. Drug Monitoring 29(6): 824-834; González et al. (2002) J. Chromatography A 949: 49-60; and others.

Detecting Enhanced Immune Responses

In certain embodiments, the methods of the invention can be used to enhance a humoral immune response (i.e., B cell response) and/or a cellular response (i.e., T cell response). An enhanced humoral immune response can be demonstrated by showing that the antibody titers against a specific antigen from, e.g., an individual who received an ARB or a compound of Formula (I) (e.g., Ondansetron and/or Alosetron) in conjunction with the antigen, are higher than antibody titers against the antigen from, e.g., an individual who received only the antigen. Antibody levels against a specific antigen can be determined via solid phase radioimmunoassay (RIA), in which serially diluted blood serum is incubated in microtiter wells previously coated with the antigen administered to the individual in conjunction with an ARB or a compound of Formula (I) (e.g., Ondansetron and/or Alosetron). Bound antibody is detected by employing 125I-labeled anti-immunoglobulin antibodies. The amount of specific antibody in the antiserum is then determined from a standard curve generated with a specific antibody of known concentration. Another method by which antibody titers can be determined is ELISA, in which an enzyme-conjugated secondary antibody, rather than radiolabeled secondary antibody, is used to detect the binding of primary antibodies to the antigen. Such methods are well known to those of skill in the art and are described in further detail in, e.g., Essentials of Immunology & Serology (Stanley, 2002); Clinical Immunology & Serology: A Laboratory Perspective (Stevens, 2009); Contemporary Clinical Immunology and Serology (Rittenhouse-Olson and DeNardin, 2012); Cooper et al. (2001) Curr Protoc Mol Biol. Chapter 11: Unit 11.17; Player et al. (1993) J Virol. Methods 45(1): 67-72; Gheesling et al. (1994) J Clin. Microbiol. 32(6): 1475-82; and others. Additionally, many commercial kits and automated systems are currently available, e.g., from Abcam, Imgenex, Cygnus, and others, to detect antigen-specific antibodies following vaccination.

An enhanced cellular immune response can be demonstrated by showing that T cells from, e.g., an individual who received an ARB or a compound of Formula (I) (e.g., Ondansetron and/or Alosetron) in conjunction with a specific antigen, are more highly activated by the antigen than T cells from, e.g., an individual who received only the antigen. One of the most common ways to assess T cell activation is to measure T-cell proliferation or T-cell cytokine elaboration upon in vitro stimulation of T-cells by the antigen administered in the methods (e.g., whole antigen or fragments thereof). This can be assessed via, e.g., ELISpot, a sensitive colorimetric assay based on ELISA that can detect secreted cytokine at the single cell level, rather than antigen-bound antibody. Details regarding ELISpot and related techniques (such as FLUROspot) are described in, e.g., Tobery et al. (2001) J. Immunol. Meth. 254: 59-66; Braun et al. (2006) Virology J. 3:53-68; Davis, et al. (2004) PNAS 101(29) 10697-10702; Posavad, et al. (2011) Vaccine 29(40): 7058-7066; Hutchings et al. (1989) J Immunol Methods. 120: 1-8; and others. ELISpot kits are also commercially available from, e.g., MABTECH AB, R&D Systems, BD Biosciences, ABCam, and other manufacturers.

T cell activation can also be assayed via flow cytometry. For example, T-cells can be stimulated with, e.g., a protein, peptide, or group of peptides derived from the antigen administered during the methods, and cultured for a period of time. During that time, an inhibitor is added which blocks the release of cytokines from the T cells. The T cells are then fixed and permeabilized to allow anti-cytokine-specific antibodies to stain the intracellular cytokines, allowing them to be visualized during FACS analysis in relatively high quantity. Further details regarding this technique are described in, e.g., Caruso et al. (1997) Cytometry 27(1): 71-76; Nomura et al. (2000) Cytometry. 40: 60-68; Suni et al. (1998) J Immunol Methods. 212: 89-98; and others.

In particular embodiments, an individual to whom an ARB or a compound of Formula (I) (e.g., Ondansetron and/or Alosetron) is administered in conjunction with an antigen can exhibit a humoral immune response that is at least about 2-fold, at least about 5-fold, at least about 10-fold, at least about 20-fold, at least about 50-fold, at least about 60-fold, at least about 70-fold, at least about 80-fold, at least about 90 fold, at least about 100-fold, at least about 110-fold, at least about 125-fold, at least about 150-fold, at least about 175-fold, at least about 200-fold, or more than 200-fold (e.g., about 250-fold, about 300-fold, or about 350-fold) higher than the humoral immune response exhibited by an individual to whom vaccine alone is administered, including any range in between about 2-fold and about 300-fold. An individual to whom an ARB or a compound of Formula (I) (e.g., Ondansetron and/or Alosetron) is administered in conjunction with an antigen can exhibit a cellular immune response that is at least about 1.2-fold, at least about 1.5-fold, at least about 2-fold, at least about 2.5-fold, at least about 3-fold, at least about 3.5 fold, at least about 4-fold, at least about 4.5-fold, at least about 5-fold, or more than about 5-fold (e.g., about 5.5-fold, about 6-fold, or about 6.5-fold) higher than the cellular immune response exhibited by an individual to whom vaccine alone is administered, including any range between about 1.2-fold and about 6.5 fold.

Antigens

In particular embodiments, the antigen is administered in conjunction with an ARB or a compound of Formula (I) (e.g., Ondansetron and/or Alosetron) in any suitable amount that is sufficient to generate an enhanced immune response. In certain embodiments, the antigen administered in conjunction with the ARB or a compound of Formula (I) (e.g., Ondansetron and/or Alosetron) can be any antigen or combination of antigens described herein. The amount of antigen to be included in the compositions and used in the methods of the present invention (i.e., any of the methods described herein) will depend on the immunogenicity of the antigen itself and the efficacy of any adjuvants co-administered therewith. In general, an immunologically effective dose comprises between about 1 µg to about 1000 µg of the antigen, preferably between about 5 µg to about 500 µg, more preferably between about 10 µg to about 200 µg. In some embodiments, an immunologically effective dose can be at least about 1 µg, at least about 5 µg, at least about 10 µg, at least about 25 µg, at least about 50 µg, at least about 100 µg, at least about 150 µg, at least about 200 µg, at least about 250 µg, at least about 300 µg, at least about 350 µg, at least about 400 µg, at least about 450 µg, at least about 500 µg, at least about 550 µg, at least about 600 µg, at least about 650 µg, at least about 700 µg, at least about 750 µg, at least about 800 µg, at least about 850 µg, at least about 950 µg, or up to about 1000 µg of antigen. In embodiments where the antigen is a recombinant protein or peptide, a suitable dose can be about 10-100 µg. In embodiments where the antigen is a recombinant protein or peptide, a suitable dose can be about 10-100 µg.

Methods of Decreasing Recruitment of Monocytes to a Lymph Node

Vaccination can trigger the mobilization and recruitment of antigen presenting cells (APC) to lymph nodes, e.g., vaccine draining lymph nodes. Monocytes, one subtype of APC, have recently been shown to have a suppressive effect on B cell and T cell proliferation, thus limiting immune responses during vaccination. The present invention is based in part on the observation that the administration of an effective amount of an ARB or a compound of Formula (I) (e.g., Ondansetron and/or Alosetron) in conjunction with an antigen decreases the recruitment of monocytes, e.g., $CD14^{hi}CD16^-$ human monocytes, to a lymph node.

Accordingly, in one embodiment, the present invention includes a method of decreasing the recruitment of monocytes to a lymph node in an individual, comprising administering to the individual an antigen and an ARB. In another embodiment, the present invention includes a method of decreasing the recruitment of monocytes to a lymph node in an individual, comprising administering to the individual an antigen and a compound of Formula (I). In certain embodiments, the ARB or compound of formula (I) are administered in an effective amount, e.g., an amount sufficient to decreasing the recruitment of monocytes to a lymph node. In particular embodiments, the antigen, the ARB and/or the compound of Formula (I) are present in one or more composition, e.g., one or more pharmaceutical compositions.

In certain embodiments, the methods of decreasing recruitment of monocytes to a lymph node provided by the invention include administering an effective amount of an ARB or a compound of Formula (I) (e.g., Ondansetron and/or Alosetron) to an individual in conjunction with an antigen. An individual to whom an ARB or a compound of Formula (I) (e.g., Ondansetron and/or Alosetron) is administered in conjunction with an antigen can exhibit a decrease in the number of monocytes that have migrated to lymph node. In certain embodiments, the decrease in the number of monocytes can be at least about 5% less, at least about 10% less, at least about 15% less, at least about 20% less, at least about 25% less, at least about 30% less, at least about 35% less, at least about 400 less, at least about 45% less, at least about 50% less, or more than about 50% less (e.g., about 55%, about 60% or about 65% less) relative to the number of monocytes that have migrated to a lymph node of an individual that has received the antigen alone, including any range between about 5% less and about 65% less. In certain embodiments, the number of monocytes that have migrated to a lymph node in an individual to whom an ARB or a compound of Formula (I) (e.g., Ondansetron and/or Alosetron) is administered in conjunction with an antigen can be more than 10% less, more than 20% less, more than 30% less, more than 40% less, more than 50% less, more than 60% less, more than about 65% less, more than about 70% less, or more than about 75% less, more than 80% less, more than about 81% more than about 82% less, more than 83% less, more than 84% less, more than 85% less, more than 86% less, more than 87% less, more than 88% less, more than 89% less, more than 90% less, at least about 91% less, at least about 93% less, or at least about 95% less than the number of monocytes that have migrated to a lymph node of an individual that has received the antigen alone, including any range between about 10% less and about 95% less.

In certain embodiments, the compound of Formula (I) (e.g., Ondansetron and/or Alosetron) administered in conjunction with the antigen can be any compound, combination of compounds, or any prodrug, salt, or derivative of a compound described herein. In certain embodiments, the combination of compound of Formula (I) and antigen is any of those described herein. In some embodiments, Ondansetron can be administered in conjunction with the antigen. In some embodiments, Alosetron can be administered in conjunction with the antigen. The antigen administered in conjunction with the compound of Formula (I) can be any antigen described herein. The antigen administered in conjunction with the compound of Formula (I) can be provided in any amount described herein. The compound of Formula (I) and the antigen can be present in a single pharmaceutical composition, or they can be provided in separate compositions that can be administered in any order relative to one another or administered simultaneously, as described herein. Compositions containing the compound of Formula (I) and/or the antigen can be administered according to any method known in the art at dosages described elsewhere herein.

In certain embodiments, the individuals to whom a compound of Formula (I) is administered in conjunction with the antigen can be those who are otherwise not receiving Ondansetron or Alosetron for the treatment of, e.g., irritable bowel syndrome (IBS), post-operative nausea and vomiting (PONV), chemotherapy-induced nausea and vomiting (CINV), radiation-induced nausea and vomiting (RINV), and/or other conditions, as described herein. In some embodiments, an individual who has a condition or disease described herein, or is otherwise in need of treatment, can receive Ondansetron and/or Alosetron in conjunction with an antigen for the purpose of enhancing an immune response if the individual is not being treated with Ondansetron and/or Alosetron. Alternatively, in certain embodiments, the individuals who are being treated with Ondansetron and/or Alosetron can temporarily suspend Ondansetron and/or Alosetron treatment. For example, an individual who is being treated with Ondansetron and/or Alosetron for a pre-existing condition can receive Ondansetron and/or Alosetron in conjunction with an antigen if the individual has taken Ondansetron and/or Alosetron for treatment of the pre-existing condition more than about 10 minutes, more than about 30 minutes, more than about 1 hour, more than about 3 hours, more than about 6 hours, more than about 12 hours, more than about 18 hours, more than about 24 hours, more than about 1 day more than about 2 days, more than about 3 days, more than about 4 days, more than about 5 days, more than about 6 days, more than about 1 week, more than about 3 weeks, more than about 1 month, more than about 2 months, more than about three months, more than about 4 months, more than about 5 months, more than about 6 months, more than about 7 months, more than about 8 months, more than about 9 months, more than about 10 months, more than about 11 months, or more than about 1 year before receiving the Ondansetron and/or Alosetron in conjunction with the antigen, including any range in between these values. Alternatively, in other embodiments, the individuals to whom a compound of Formula (I) is administered in conjunction with an antigen can be those who have temporarily suspended Ondansetron and/or Alosetron treatment and have been shown, using methods well known in the art, to not have detectable levels of Ondansetron and/or Alosetron in their blood and/or urine prior to the administration of Ondansetron and/or Alosetron in conjunction with the antigen.

In particular embodiments, the ARB administered in conjunction with the antigen can be any ARB, combination of ARBs, or any prodrug, salt, or derivative of an ARB described herein. The antigen administered in conjunction with the ARB can be any antigen described herein. In certain embodiments, the combination of the ARB and the antigen is any described herein. The antigen administered in conjunction with the ARB can be provided in any amount described herein. The ARB and the antigen can be present in a single pharmaceutical composition, or they can be provided in separate compositions that can be administered in any order relative to one another or administered simultaneously, as described herein.

In particular embodiments, the individuals to whom an ARB is administered in conjunction with an antigen can be those who are otherwise not receiving an ARB for treatment of a pre-existing condition, e.g., hypertension, diabetic nephropathy, heart failure, and/or other conditions, as described herein. In some embodiments, an individual who has a condition or disease described herein, or who is otherwise in need of treatment, can receive an ARB in conjunction with an antigen for the purpose of enhancing an immune response if the individual is not being treated with an ARB. Alternatively, in some embodiments, the individuals to whom an ARB is administered in conjunction with an antigen can be those who have temporarily suspended ARB treatment. For example, an individual who is being treated with an ARB for a pre-existing condition can receive an ARB in conjunction with an antigen if the individual has taken the ARB for treatment more than about 10 minutes, more than about 30 minutes, more than about 1 hour, more than about 3 hours, more than about 6 hours, more than about 12 hours, more than about 18 hours, more than about 24 hours, more than about 1 day more than about 2 days, more than about 3 days, more than about 4 days, more than about 5 days, more than about 6 days, more than about 1 week, more than about 3 weeks, more than about 1 month, more than about 2 months, more than about three months, more than about 4 months, more than about 5 months, more than about 6 months, more than about 7 months, more than about 8 months, more than about 9 months, more than about 10 months, more than about 11 months, or more than about 1 year before receiving the ARB in conjunction with the antigen, including any range in between these values. Alternatively, in certain embodiments, an individual who is being treated with an ARB for a pre-existing condition can suspend ARB treatment and be tested, using methods well known in the art, to determine that the individual does not have a detectable level of an ARB in their blood and/or urine prior to the administration of the ARB in conjunction with the antigen.

Monocytes

Monocytes are agranular leukocytes that originate in the bone marrow and are released to the peripheral circulation as non-dividing cells. Monocytes constitute approximately 10% of peripheral leukocytes in humans and approximately 4% of leukocytes in mice. Monocytes are equipped with chemokine receptors and adhesion receptors that mediate migration from blood to tissues during infection, where they engulf pathogens and produce immune effector molecules. They can also differentiate into inflammatory dendritic cells or macrophages during inflammation.

In mice, circulating monocytes can be classified into two distinct populations, inflammatory monocytes and resident monocytes, based on the expression of specific cell surface markers. Murine inflammatory monocytes are categorized as $CCR2^+$, $CX3CR1^{low}$, and $GR1^+$ (also known as Ly6). The monocyte cell population found to suppress vaccine immunity primarily includes $CCR2^+$ monocytes Mitchell et al. (2012) J. Immunology 189: 5612-5621. Human monocyte subpopulations have also been identified based on the differential expression of the antigenic markers CD16 and CD14. The human monocytes that correspond to murine inflammatory monocytes are categorized as $CD14^{high}CD16^-$.

Detecting a Reduction of Monocyte Recruitment to a Lymph Node

Vaccines can induce inflammation, which typically results in the recruitment of monocytes to the site of vaccination and to the lymph nodes, i.e., lymph nodes that lie immediately downstream of the vaccination site, or "vaccine draining lymph nodes." Decreased monocyte migration to a lymph node can be demonstrated by showing that the number of monocytes in, e.g., a vaccine draining lymph node of a human individual who received an ARB or a compound of Formula (I) (e.g., Ondansetron and/or Alosetron) in conjunction with the antigen, is lower than the number of monocytes in, e.g., a vaccine draining lymph node of a human individual who received only the antigen. This can be assayed by performing flow cytometry on tissue obtained from each individual's lymph nodes and, e.g., determining whether fewer $CD14^{hi}CD16^-$ monocytes are detected in the tissue from the individual who received the ARB or the compound of Formula (I) (e.g., Ondansetron and/or Alosetron) in conjunction with the antigen than in the tissue from an individual who did not receive the ARB or the compound of Formula (I). In certain embodiments, decreased monocyte migration to a lymph node, e.g., a vaccine draining lymph node, can be demonstrated by detecting a change in the circulating levels of, e.g., total monocytes or inflammatory monocyte, within the first 24 hours after the ARB or the compound of Formula (I) is administered to the individual in conjunction with the antigen.

Methods of determining the amount of circulating $CD14^{hi}CD16^-$ monocytes or circulating inflammatory monocytes are known in the art. For example, blood specimens can be collected from individuals and prepared for flow cytometry using labeled antibodies against $CD14^{hi}CD16^-$ monocyte-specific cell surface markers or against inflammatory monocyte cell surface markers, such as those described elsewhere herein. Absolute numbers of monocytes can be calculated using leukocyte counts derived from an automated blood cell counter. Alternatively, skin biopsies taken at or near, e.g., vaccine injection sites, can be collected from individuals within 24 hours of receiving a vaccine in conjunction with an ARB, and the biopsied tissue can prepared so that the number of monocytes in the tissue can be quantified and compared to the number of monocytes counted in a tissue obtained from an individual who received the vaccine alone. For example, an aspirate of the draining lymph node, e.g., nearest to the vaccine injection site, can be taken via ultrasound imaging, and the number of monocytes in the aspirate can be quantified and compared between an individual who received an ARB in conjunction with a vaccine and an individual who received the vaccine alone. Additional methods of determining levels of circulating monocytes that can be used are described in, e.g., Aldonyte et al. (2003) Resp. Res. 4:11; Janciauskiene et al. (2001) Atherosclerosis 158: 41-51; Nockher et al. (1998) Infect Immun. 66: 2782-2790; and others.

Methods of Amplifying Vaccine Immunity

Vaccines have played a key role in reducing the incidence of debilitating and/or fatal diseases. Vaccine immunity depends on the ability of individuals to mount a robust immune response. As noted above, inflammatory monocytes are rapidly recruited to the site of vaccination and to lymph nodes, where they suppress B cell and T cell responses. This a particular public health concern in, e.g., vulnerable populations that exhibit reduced immune responsiveness, such as the young, the elderly, and the immunocompromised. The invention provides methods that can be beneficially used to substantially amplify vaccine immunity. As used herein, "amplifying vaccine immunity" refers to increasing a vaccine-induced immune response, e.g., a vaccine-induced humoral (or B-cell) immune response and/or a vaccine-induced cellular (or T-cell) immune response.

Accordingly, in one embodiment, the present invention includes a method of amplifying vaccine immunity in an individual, comprising administering to the individual a vaccine and an ARB. In another embodiment, the present invention includes a method of amplifying vaccine immunity in an individual, comprising administering to the individual a vaccine and a compound of Formula (I). In certain embodiments, the ARB or compound of formula (I) are administered in an effective amount, e.g., an amount sufficient to amplify vaccine immunity. In particular embodiments, the antigen, the ARB and/or the compound of Formula (I) are present in one or more composition, e.g., one or more pharmaceutical compositions.

In certain embodiments, the methods include administering an ARB or a compound of Formula (I) (e.g., Ondansetron and/or Alosetron) to an individual in conjunction with a vaccine. An amplified humoral (or B-cell) immune response can be demonstrated by showing that the antibody titers from, e.g., an individual who received an ARB or a compound of Formula (I) (e.g., Ondansetron and/or Alosetron) in conjunction with the vaccine, are higher than antibody titers from, e.g., an individual who received only the vaccine. In certain embodiments, an individual to whom an ARB or a compound of Formula (I) (e.g., Ondansetron and/or Alosetron) was administered in conjunction with a vaccine or an antigen can exhibit a humoral immune response that is at least about 2-fold, at least about 5-fold, at least about 10-fold, at least about 20-fold, at least about 50-fold, at least about 60-fold, at least about 70-fold, at least about 80-fold, at least about 90 fold, at least about 100-fold, at least about 110-fold, at least about 125-fold, at least about 150-fold, at least about 175-fold, at least about 200-fold, or more than 200-fold (e.g., about 250-fold, about 300-fold, or about 350-fold) higher than the humoral immune response exhibited by an individual to whom vaccine alone was administered, including any range in between about 2-fold and about 300-fold. In certain embodiments, an individual to whom an ARB or a compound of Formula (I) (e.g., Ondansetron and/or Alosetron) was administered in conjunction with a vaccine or an antigen can exhibit a cellular immune response that is at least about 1.2-fold, at least about 1.5-fold, at least about 2-fold, at least about 2.5-fold, at least about 3-fold, at least about 3.5 fold, at least about 4-fold, at least about 4.5-fold, at least about 5-fold, or more than about 5-fold (e.g., about 5.5-fold, about 6-fold, or about 6.5-fold) higher than the cellular immune response exhibited by an individual to whom vaccine alone was administered, including any range between about 1.2-fold and about 6.5 fold.

In particular embodiments, the compound of Formula (I) administered in conjunction with the vaccine can be any compound, combination of compounds, or any prodrug, salt, or derivative of a compound described herein. In particular embodiments, the vaccine is any described herein. In particular embodiments, the combination of vaccine and compound of Formula (I) is any described herein. In some embodiments, the vaccine can be administered in conjunction with Ondansetron. In some embodiments, the vaccine can be administered in conjunction with Alosetron. The compound of Formula (I) and the vaccine can be present in a single pharmaceutical composition, or they can be provided in separate compositions that can be administered in any order relative to one another or administered simultaneously, as described herein. Compositions containing the compound of Formula (I) and/or the vaccine can be administered according to any method known in the art at dosages described elsewhere herein.

In particular embodiments, the ARB administered in conjunction with the vaccine can be any ARB, combination of ARBs, or any prodrug, salt, or derivative of an ARB described herein. In particular embodiments, the vaccine is any described herein. In particular embodiments, the combination of vaccine and ARB is any described herein. The ARB and vaccine can be present in a single pharmaceutical composition, or they can be provided in separate compositions that can be administered in any order relative to one another or administered simultaneously, as described herein. Compositions containing the ARB and/or the vaccine can be administered according to any method known in the art at dosages described elsewhere herein.

In particular embodiments, the individuals to whom an a compound of Formula (I) is administered in conjunction with the vaccine can be those who are otherwise not receiving Ondansetron or Alosetron for the treatment of, e.g., irritable bowel syndrome (IBS), post-operative nausea and vomiting (PONV), chemotherapy-induced nausea and vomiting (CINV), radiation-induced nausea and vomiting (RINV), and/or other conditions, as described herein. In some embodiments, an individual who has a condition or disease described herein, or is otherwise in need of treatment, can receive Ondansetron and/or Alosetron in conjunction with a vaccine for the purpose of enhancing an immune response if the individual is not being treated with Ondansetron and/or Alosetron. Alternatively, in some embodiments, the individuals on whom the methods are practiced have temporarily suspended Ondansetron and/or Alosetron treatment and have been shown, using methods well known in the art, to not have detectable levels of Ondansetron and/or Alosetron in their blood and/or urine prior to the administration of the Ondansetron and/or Alosetron in conjunction with the vaccine.

In particular embodiments, the individuals to whom an ARB is administered in conjunction with a vaccine can be those who are otherwise not receiving an ARB for treatment of a pre-existing condition, e.g., hypertension, diabetic nephropathy, heart failure, and/or other conditions, as described herein. In another embodiment, an individual who has a condition or disease described herein, or who is otherwise in need of treatment, can receive an ARB in conjunction with a vaccine for the purpose of enhancing an immune response if the individual is not being treated with an ARB. Alternatively, in some embodiments, the individuals to whom an ARB is administered in conjunction with a vaccine can be those who have temporarily suspended ARB treatment. For example, an individual who is being treated with an ARB for a pre-existing condition can receive an ARB in conjunction with a vaccine if the individual has taken the ARB for treatment more than about 10 minutes, more than about 30 minutes, more than about 1 hour, more than about 3 hours, more than about 6 hours, more than about 12 hours, more than about 18 hours, more than about 24 hours, more than about 1 day more than about 2 days, more than about 3 days, more than about 4 days, more than about 5 days, more than about 6 days, more than about 1 week, more than about 3 weeks, more than about 1 month, more than about 2 months, more than about three months, more than about 4 months, more than about 5 months, more than about 6 months, more than about 7 months, more than about 8 months, more than about 9 months, more than about 10 months, more than about 11 months, or more than about 1 year before receiving the ARB in conjunction with the vaccine, including any range in between these values. Alternatively, in some embodiments, an individual who is being treated with an ARB for a pre-existing condition can suspend ARB treatment and be tested, using methods well known in the art, to determine that the individual does not have a detectable level of an ARB in their blood and/or urine prior to the administration of the ARB in conjunction with the vaccine.

Vaccines

A vaccine is a composition that contains an antigen which, when administered to an individual, stimulates an immune response. Vaccines confer long-term immunity by inducing the development of immune memory cells that are able to mount a strong response if the pathogen is detected again. The vaccine that is administered in the methods can be any vaccine or vaccine formulation known to those of skill in the art. For example, the vaccine administered in conjunction with an ARB or a compound of Formula (I) (e.g., Ondansetron and/or Alosetron) can contain any antigen known in the art. In certain embodiments, the vaccine administered in conjunction with an ARB or a compound of Formula (I) (e.g., Ondansetron and/or Alosetron) can contain any antigen or combination of antigens described herein, e.g., a live infectious agent, a killed infectious agent, a polysaccharide, or a toxin produced by an infectious agent. In certain embodiments of the methods, the vaccine contains specific proteins, e.g., purified from an infection agent or recombinantly produced. In certain embodiments of the methods, the polysaccharide or protein present in the vaccine is conjugated to an immuno-stimulating molecule, such as a carrier protein.

In some embodiments, the vaccine administered in conjunction with the ARB or the compound of Formula (I) (e.g., Ondansetron and/or Alosetron) can be a DNA vaccine, which entails direct introduction into appropriate tissues of, e.g., a plasmid encoding the antigen(s) against which an immune response is sought, and which relies on the in situ production of the target antigen. Further details regarding DNA vaccines are described in, e.g., DNA Vaccines: Methods and Protocols (Douglas B. Lourie and Robert Whalen, eds., 2000) Humana Press; DNA Vaccines (Mark Saltzman, Hong Shen, and Janet Brandsma, eds. 2006) Human Press; and others.

In certain embodiments, the vaccine administered in conjunction with an ARB or a compound of Formula (I) (e.g., Ondansetron and/or Alosetron) can be a viral vector vaccine, which is typically a live attenuated virus that is genetically engineered to carry DNA encoding protein antigens from an unrelated organism. Viral vector vaccines carry DNA into a host cell for production of antigenic proteins that can be tailored to stimulate an immune responses. Viral vector vaccines, unlike DNA vaccines, also have the potential to actively invade host cells and replicate, much like a live attenuated vaccine, further activating the immune system like an adjuvant. Further details regarding viral vector vaccines are described in, I, Bråve et al. (2007) Mol Pharm. 4: 18-32; Kaufmann et al. (2012) Trends Mol Med. 18: 365-7; Ulmer et al. (2012) Vaccine. 30: 4414-4418; and others.

In certain embodiments, the vaccine administered in conjunction with an ARB or a compound of Formula (I) (e.g., Ondansetron and/or Alosetron) can be a dendritic cell vaccine. Dendritic cells (DCs) are antigen-presenting cells that are involved in the induction of primary immune responses. The unique ability of DCs to activate naive and memory $CD4^+$ and $CD8^+$ T cells suggests that they could be used, e.g., for the induction of a specific anti-tumor immunity. An individual's DCs can be harvested, pulsed with one or more antigens, and used to re-immunize the individual to induce a protective immune response. Further details regarding dendritic cell vaccines are described in, e.g., Pellegatta et al. (2009) Methods Mol Biol. 568: 233-247; Bhargava et al. (2012) Immunotherapy. 4: 703-718; Van Brussel et al. (2012) Mediators Inflamm. Article ID 690643; Yamanaka et al. (2012) Adv Exp Med Biol. 746:187-200; and others.

Methods of Inhibiting Tumor Growth or Metastasis

Therapeutic cancer vaccines stimulate the immune system to recognize tumor-specific antigens and to generate an immune response to find and destroy cells that express them. Producing effective therapeutic vaccines has been difficult, as genetically unstable cancer cells are capable of evading immune recognition. Recent evidence indicates that monocyte depletion can increase the efficacy of cancer vaccine (Mitchell et al. (2012) "Suppression of Vaccine Immunity by Inflammatory Monocytes." J. Immunology 189: 5612-5621 and U.S. Patent Application Publication No. US 2012/0156280). The angiotensin II receptor blockers (ARB) and the compounds of Formula (I) described herein (e.g., Ondansetron or Alosetron) can be used to inhibit monocyte migration, thus amplifying cancer vaccine immunity by enhancing an immune response.

Accordingly, in one embodiment, the present invention includes a method of inhibiting tumor growth or metastasis in an individual, comprising administering to the individual an anti-tumor preparation and an ARB. In another embodiment, the present invention includes a method of inhibiting tumor growth or metastasis in an individual, comprising administering to the individual an anti-tumor preparation and a compound of Formula (I). In particular embodiments, the anti-tumor preparation is any described herein. In particular embodiments, the combination of an anti-tumor preparation and a compound of Formula (I) is any described herein. In certain embodiments, the ARB or compound of formula (I) are administered in an effective amount, e.g., an amount sufficient to inhibit tumor growth or metastasis (e.g., when administered with an anti-tumor preparation). In particular embodiments, the antigen, the ARB and/or the compound of Formula (I) are present in one or more composition, e.g., one or more pharmaceutical compositions. In particular embodiments, the anti-tumor preparation and the ARB or compound of Formula (I) are present in a single composition. In particular embodiments, the individual has a tumor.

In particular embodiments, these uses/methods include administering an effective amount of an ARB or a compound of Formula (I) (e.g., Ondansetron and/or Alosetron) in conjunction with an anti-tumor preparation to an individual. In some embodiments, the ARB or the compound of Formula (I) (e.g., Ondansetron and/or Alosetron) is administered in conjunction with an anti-tumor preparation to inhibit the tumor growth or metastasis of an epithelial cancer, breast cancer, prostate cancer, colon cancer, a hematopoietic cancer, leukemia, lymphoma, a sarcoma, melanoma, a head sarcoma, a neck sarcoma, a squamous cell carcinoma, an osteosarcoma, or a brain tumor.

In some embodiments, tumor growth in an individual to whom an ARB or a compound of Formula (I) (e.g., Ondansetron and/or Alosetron) is administered in conjunction with an anti-tumor preparation is reduced by at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, or at least about 95% as compared to tumor growth in an individual who received the anti-tumor preparation alone. In some embodiments, tumor metastasis in an individual to whom an ARB or a compound of Formula (I) (e.g., Ondansetron and/or Alosetron) is administered in conjunction with an anti-tumor preparation is reduced by at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, or at least about 95% as compared to tumor metastasis in an individual who received the anti-tumor preparation alone.

Tumor metastasis can be measured by any suitable method known to the skilled artisan. In certain embodiments, tumor metastases are measured by counting the number of tumor nodules (i.e., the number of tumor metastases present in an individual). In certain embodiments, tumor metastases are measured by by determining the overall size of the tumor nodules, or the volume of tumor nodules as measured by CT or MRI.

In certain embodiments, the compound of Formula (I) (e.g., Ondansetron and/or Alosetron) administered in conjunction with the anti-tumor preparation can be any compound, combination of compounds, or any prodrug, salt, or derivative of compound of Formula (I) herein. In some embodiments, the anti-tumor preparation can be administered in conjunction with Alosetron. In some embodiments, the anti-tumor preparation can be administered in conjunction with Ondansetron. The compound of Formula (I) and an anti-tumor preparation can be present in a single pharmaceutical composition, or they can be provided in separate compositions that can be administered in any order relative to one another or administered simultaneously, as described herein. Compositions containing the compound of Formula (I) (e.g., Ondansetron and/or Alosetron) and/or the anti-tumor preparation can be administered according to any method known in the art at dosages described elsewhere herein.

In certain embodiments, the individuals to whom a compound of Formula (I) is administered in conjunction with the anti-tumor preparation can be those who are otherwise not receiving Ondansetron or Alosetron for the treatment of, e.g., irritable bowel syndrome (IBS), post-operative nausea and vomiting (PONV), chemotherapy-induced nausea and vomiting (CINV), radiation-induced nausea and vomiting (RINV), and/or other conditions, as described herein. In some embodiments, an individual who has a condition or disease described herein, or is otherwise in need of treatment, can receive Ondansetron and/or Alosetron in conjunction with an anti-tumor preparation for the purpose of enhancing an immune response if the individual is not being treated with Ondansetron and/or Alosetron. Alternatively, in some embodiments, the individuals on whom the methods are practiced have temporarily suspended Ondansetron and/or Alosetron treatment and have been shown, using methods well known in the art, to not have detectable levels of Ondansetron and/or Alosetron in their blood and/or urine prior to the administration of the Ondansetron and/or Alosetron in conjunction with the anti-tumor preparation.

In particular embodiments, the ARB administered in conjunction with the anti-tumor preparation can be any ARB, combination of ARBs, or any prodrug, salt, or derivative of an ARB described herein. The ARB and anti-tumor preparation can be present in a single pharmaceutical composition, or they can be provided in separate compositions that can be administered in any order relative to one another or administered simultaneously, as described herein. Compositions containing the ARB and/or the anti-tumor preparation can be administered according to any method known in the art at dosages described elsewhere herein.

In certain embodiments, the individuals to whom an ARB is administered in conjunction with an anti-tumor preparation can be those who are otherwise not receiving an ARB for treatment of a pre-existing condition, e.g., hypertension, diabetic nephropathy, heart failure, and/or other conditions, as described herein. In some embodiments, an individual who has a condition or disease described herein, or who is otherwise in need of treatment, can receive an ARB in conjunction with an anti-tumor preparation for the purpose of enhancing an immune response if the individual is not being treated with an ARB. Alternatively, in some embodiments, the individuals to whom an ARB is administered in conjunction with an anti-tumor preparation can be those who have temporarily suspended ARB treatment. For example, an individual who is being treated with an ARB for a pre-existing condition can receive an ARB in conjunction with an anti-tumor preparation if the individual has taken the ARB for treatment more than about 10 minutes, more than about 30 minutes, more than about 1 hour, more than about 3 hours, more than about 6 hours, more than about 12 hours, more than about 18 hours, more than about 24 hours, more than about 1 day more than about 2 days, more than about 3 days, more than about 4 days, more than about 5 days, more than about 6 days, more than about 1 week, more than about 3 weeks, more than about 1 month, more than about 2 months, more than about three months, more than about 4 months, more than about 5 months, more than about 6 months, more than about 7 months, more than about 8 months, more than about 9 months, more than about 10 months, more than about 11 months, or more than about 1 year before receiving the ARB in conjunction with the anti-tumor preparation, including any range in between these values. Alternatively, in some embodiments, an individual who is being treated with an ARB for a pre-existing condition can suspend ARB treatment and be tested, using methods well known in the art, to determine that the individual does not have a detectable level of an ARB in their blood and/or urine prior to the administration of the ARB in conjunction with the anti-tumor preparation.

Anti-Tumor Preparations

The anti-tumor preparation administered in conjunction with the ARB or the compound of Formula (I) (e.g., Ondansetron and/or Alosetron) can be any anti-tumor preparation known and used in the art. For example, certain anti-tumor preparations inhibit the synthesis of new DNA strands, thus preventing tumor cells from replicating. In certain embodiments, the anti-tumor preparation administered in conjunction with the ARB or the compound of Formula (I) (e.g., Ondansetron and/or Alosetron) can be an antimetabolite, such as 5-fluorouracil, methotrexate, capecitabine, Alimta, gemcitabine, etc. In certain embodiments, the anti-tumor preparation can be a platinum-based agent, such as cisplatin, carboplatin, oxaliplatin, and the like, which cross-link DNA and inhibit DNA repair in tumor cells. In certain embodiments, the anti-tumor preparation can be an alkylating agent, such as cyclophosphamide, carmustine (BCNU), methyl-CCNU, or piposulfan. In certain embodiments, the anti-tumor agent can be a tyrosine kinase inhibitor, such as gefitinib (Iressa®), imatinib (Gleevec®), lapatinib, sunitinib (Sutent®), or Tarceva. In certain embodiments, the anti-tumor preparation can be an anthracycline, such as actinomycin, doxil, doxorubicin (adriamycin), epirubicin, or mitoxantrone. In certain embodiments, the anti-tumor preparation can be a topoisomerase inhibitor, such as camptothecin, irinotecan, topotecan, etoposide, amsacrine, etoposide phosphate, or teniposide.

Other anti-tumor preparations interfere with microtubule assembly or disassembly, thus interrupting tumor cell division. In certain embodiments, the anti-tumor preparation can be a vinca alkaloid, such as vinblastine, vincristine, vindesine, VP-16, or vinorelbine (Navelbine®). Other anti-tumor agents that exhibit anti-microtubule activity include colchicine, taxanes and taxane derivatives. Additional anti-tumor preparations that can be administered in conjunction with an ARB or a compound of Formula (I) include proteasome inhibitors (e.g., bortezomib (Velcade)); anti-angiogenesis agents; and therapeutic antibodies (e.g., anti-VEGF antibody/Avastin®/bevacizumab, anti-HER2 antibody/Herceptin®/trastuzumab, Erbitux®/cetuximab, Campath/Alemtuzumab, Myelotarg/gemtuzumab, Zevalin/ibritumomab tiuextan, Rituxan/rituximab, and Bexxar/tositumomab). In certain embodiments, two or more anti-tumor preparations can be administered in conjunction with an ARB or a compound of Formula (I) (e.g., Ondansetron and/or Alosetron).

In certain embodiments, the anti-tumor preparation that is administered in conjunction with an ARB or a compound of Formula (I) (e.g., Ondansetron and/or Alosetron) can be a cancer vaccine, e.g., a cancer vaccine designed to increase the targeted immune response against cancer cells already present in the individual. In certain embodiments, the cancer vaccine administered in conjunction with an ARB or a compound of Formula (I) (e.g., Ondansetron and/or Alosetron) can contain whole inactivated tumor cells, parts of tumor cells, or tumor cell lysates. In certain embodiments, the cancer vaccine includes a tumor-specific antigen, such as a protein, peptide, or carbohydrate. In certain embodiments, the cancer vaccine that is administered in conjunction with an ARB or a compound of Formula (I) (e.g., Ondansetron and/or Alosetron) can include a nucleic acid, viral vector, or bacterial vector that encodes a tumor-specific antigen. In certain embodiments, the cancer vaccine that is administered in conjunction with an ARB or a compound of Formula (I) (e.g., Ondansetron and/or Alosetron) can be a dendritic cell vaccine that has been pulsed with a tumor-specific antigen. The tumor-specific antigen can be any tumor-specific antigen known in the art, including, but not limited to, e.g., melanA/MART-, NY-ESO-1, MAGE, ETA, CEA, CA-125, CA15-3, CA27-29, CA19-9, MUC-1, AFP, an abnormal product of the ras gene, an abnormal product of the p53 gene, CAMEL, Ep-CAM, her-2/neu, WT-1, EBNA3, CD10, CD34, CD99, CD117, CD45 (PTPRC), chromogranin, mucin, LMP2, E6, E7, K12, K8.1, tyrosinase, proteinase 3, GM2, GD2, GD3, polysialic acid, fucosyl GM1, globo H, KSA, sialyl Le$^a$, Le$^y$, TF, Tn, sTn, PSMA, PSA, MUC16, SAGE1, HBA-71, calretinin, carcinoembryonic antigen, a cytokeratin, desmin, EMA, Factor VIII, CD31 FL1, GFAP, GCDFP-15, HMB-25, an immunoglobulin, inhibin, keratin, a lymphocyte marker, Myo D1, MSA, neuofilament, NSE, PLAP, S100, SMA, synaptophysin, thyroglobulin, vimentin, tumor M2-PK, thyroid transcription factor-1, a squamous cell carcinoma tumor-specific antigen, an osteosarcoma tumor-specific antigen, or a brain tumor-specific antigen. Alternatively, the cancer vaccine can include a peptide or polysaccharide derived from any of the tumor-specific antigen listed above.

Administering an ARB or a Compound of Formula (I) in Conjunction with an Antigen, Vaccine, or Anti-Tumor Preparation Various methods described above entail administering an ARB or a compound of Formula (I) (e.g., Ondansetron and/or Alosetron) in conjunction with an antigen, a vaccine, or an anti-tumor preparation. The ARB or the compound of Formula (I) (e.g., Ondansetron and/or Alosetron) and the antigen, vaccine, or anti-tumor preparation can be present in a single composition. Alternatively, the ARB or the compound of Formula (I) (e.g., Ondansetron and/or Alosetron) and the antigen, vaccine, or anti-tumor preparation can be provided in separate compositions. For example, the ARB or the compound of Formula (I) (e.g., Ondansetron and/or Alosetron) can be provided as a tablet for oral administration, and the antigen, vaccine, or anti-tumor preparation can be provided in an injectable composition. Where the ARB or the compound of Formula (I) (e.g., Ondansetron and/or Alosetron) and the antigen, vaccine, or anti-tumor preparations are present in separate compositions, the two compositions can be administered in any order relative to one another. For example, the ARB or the compound of Formula (I) (e.g., Ondansetron and/or Alosetron) can be administered before the antigen, vaccine, or anti-tumor preparation. Alternatively, the antigen, vaccine, or anti-tumor preparation can be administered before the ARB or the compound of Formula (I) (e.g., Ondansetron and/or Alosetron). The pharmaceutical composition containing the ARB or the compound of Formula (I) (e.g., Ondansetron and/or Alosetron) and the pharmaceutical composition containing the antigen, vaccine, or anti-tumor preparation can be administered within at least about 12 hours, within at least about 11 hours, within at least about 10 hours, within at least about 9 hours, within at least about 8 hours, within at least about 7 hours, within at least about 6 hours, within at least about 5 hours, within at least about 4 hours, within at least about 3 hours, within at least about 2 hours, within at least about 1 hour, or less than 1 hour (e.g., within about 45 minutes, within about 30 minutes, within about 15 minutes, within about 10 minutes, within about 5 minutes, less than 5 minutes, less than 4 minutes, less than 3 minutes, less than 2 minutes, or less than 1 minute) of one another, including any ranges between these values. In certain embodiments, the two compositions can be administered simultaneously, e.g., premixed and administered.

Accordingly, in certain embodiments, the compositions of the invention include Ondansetron and an antigen, vaccine, or anti-tumor preparation. In certain embodiments, the composition is administered orally. In certain embodiments, Ondansetron in the orally administered composition is at a concentration sufficient to provide a dose of at least about 0.5 mg, at least about 1 mg, at least about 2 mg, at least about 3 mg, at least about 4 mg, at least about 5 mg, at least about 6 mg, at least about 7 mg, at least about 8 mg, at least about 10 mg, or less than about 12 mg Ondansetron, including any range in between these values. In certain embodiments, the Ondansetron in the orally administered composition is at a concentration sufficient to provide a dose of more than about 24 mg, more than about 26 mg, more than about 28 mg, more than about 30 mg, more than about 32 mg, or more than about 34 mg Ondansetron, including any range in between these values.

In certain embodiments, compositions are administered intravenously. Compositions for intravenous administration can include Ondansetron at a concentration sufficient to provide a dose of at least about 0.01 mg/kg/day, at least about 0.05 mg/kg/day, at least about 0.1 mg/kg/day, at least about 0.15 mg/kg/day, at least about 0.2 mg/kg/day, at least about 0.3 mg/kg/day, at least about 0.4 mg/kg/day, at least about 0.5 mg/kg/day, at least about 0.75 mg/kg/day, at least about 1.0 mg/kg/day, at least about 1.5 mg/kg/day, at least about 2.0 mg/kg/day, at least about 2.5 mg/kg/day, at least about 3.0 mg/kg/day, at least about 3.5 mg/kg/day, at least about 4.0 mg/kg/day, at least about 4.5 mg/kg/day, at least about 5.0 mg/kg/day, at least about 5.5 mg/kg/day, at least about 6.0 mg/kg/day, at least about 6.5 mg/kg/day, at least about 7.0 mg/kg/day, at least about 7.5 mg/kg/day, at least about 8.0 mg/kg/day, or less than about 8.5 mg/kg/day of Ondansetron, including any range between these values.

For example, the invention provides compositions that can include Alosetron and an antigen, vaccine, or anti-tumor preparation, where the Alosetron in the composition is at a concentration sufficient to provide a dose of at least about 0.1 mg, at least about 0.2 mg, at least about 0.3 mg, at least about 0.4 mg, or less than about 0.5 mg Alosetron, including any range between these values. In certain embodiments, the Alosetron in the composition is at a concentration sufficient to provide a dose of more than about 2 mg, more than about 3 mg, more than about 4 mg, more than about 5 mg, or more than about 6 mg Alosetron, including any range in between these values.

In certain embodiments, the ARB administered in conjunction with the antigen, vaccine, or anti-tumor preparation can be any ARB, combination of ARBs, or any prodrug, salt, or derivative of an ARB described herein. For example, Losartan can be administered in conjunction with the antigen, vaccine, or anti-tumor preparation at a concentration sufficient to provide a dose of at least about 5 mg, at least about 10 mg, at least about 15 mg, at least about 20 mg, or less than about 25 mg of Losartan, including any range in between these values. In certain embodiments, the Losartan in the composition is at a concentration sufficient to provide a dose of more than about 80 mg, more than about 100 mg, more than about 125 mg, more than about 150 mg, more than about 175 mg, or more than about 200 mg or Losartan, including any range in between about 5 mg and about 200 mg.

In certain embodiments, compositions of the invention can include Losartan at a concentration sufficient to provide a dose of at least about 0.5 mg/kg, at least about 0.75 mg/kg, at least about 1.0 mg/kg, at least about 1.25 mg·kg, at least about 1.5 mg/kg, at least about 1.75 mg/kg, or at least about 2.0 mg/kg of Losartan, including any range between about 0.5 mg/kg and about 1.75 mg/kg. In certain embodiments, compositions of the invention can include Losartan at a concentration sufficient to provide a dose of more than about 1.75 mg/kg, at least about 2.0 mg/kg, at least about 5 mg/kg, at least about 7 mg/kg, at least about 10 mg/kg, at least about 12 mg/kg, at least about 15 mg/kg, at least about 17 mg/kg, at least about 20 mg/kg, at least about 22 mg/kg, at least about 25 mg/kg, at least about 27 mg/kg, or at least about 30 mg/kg or Losartan, including any range in between about 1.75 mg/kg and about 30 mg/kg. In certain embodiments, the compositions of the invention can include Losartan at a concentration sufficient to provide a dose of more than about 30 mg/kg, e.g., at least about 35 mg/kg or at least about 40 mg/kg of Losartan, including any range in between about 30 mg/kg and about 40 mg/kg.

In certain embodiments, Candesartan can be administered in conjunction with an antigen, vaccine, or anti-tumor preparation at a dosage of less than about 4 mg, less than about 3 mg, less than about 2 mg, or less than about 1 mg, including any range between these values. In certain embodiments, Candesartan can be administered in conjunction with an antigen, vaccine, or anti-tumor preparation at a dosage of more than about 32 mg, more than about 40 mg, more than about 48 mg, more than about 56 mg, or more than about 64 mg, including any range in between these values.

In certain embodiments, Erposartan can be administered in conjunction with an antigen, vaccine, or anti-tumor preparation at a dosage of less than about 400 mg, less than about 300 mg, less than about 200 mg, less than about 100 mg, or less than about 50 mg, including any range between these values. In certain embodiments, Eprosartan can be administered in conjunction with an antigen, vaccine, or anti-tumor preparation at a dosage of more than about 600 mg, more than about 750 mg, more than about 900 mg, more than about 1050 mg, or more than about 1200 mg, including any range in between these values.

In certain embodiments, Irbesartan can be administered in conjunction with an antigen, vaccine, or anti-tumor preparation at a dosage of about less than 150 mg, less than about 100 mg, less than about 50 mg, or less than about 25 mg, including any range between these values. In certain embodiments, Irbesartan can be administered in conjunction with an antigen, vaccine, or anti-tumor preparation at a dosage of more than about 300 mg, more than about 375 mg, more than about 450 mg, more than about 525 mg, or more than about 600 mg, including any range in between these values.

In certain embodiments, Olmesartan can be administered in conjunction with an antigen, vaccine, or anti-tumor preparation at a dosage of less than about 20 mg, less than about 15 mg, less than about 10 mg, or less than about 5 mg, including any range between these values. In certain embodiments, Olmesartan can be administered in conjunction with an antigen, vaccine, or anti-tumor preparation at a dosage of more than about 40 mg, more than about 50 mg, more than about 60 mg, more than about 70 mg, or more than about 40 mg, including any range in between these values.

In certain embodiments, Telmisartan can be administered in conjunction with an antigen, vaccine, or anti-tumor preparation at a dosage of less than about 20 mg, less than about 15 mg, less than about 10 mg, or less than about 5 mg, including any range between these values. In certain embodiments, Telmisartan can be administered in conjunction with an antigen, vaccine, or anti-tumor preparation at a dosage of more than about 80 mg, more than about 100 mg, more than about 120 mg, more than about 140 mg, or more than about 160 mg, including any range in between these values.

In certain embodiments, Valsartan can be administered in conjunction with an antigen, vaccine, or anti-tumor preparation at a dosage of less than about 20 mg, less than about 15 mg, less than about 10 mg, or less than about 5 mg, including any range between these values. In certain embodiments, Valsartan can be administered in conjunction with an antigen, vaccine, or anti-tumor preparation at a dosage of more than about 320 mg, more than about 400 mg, more than about 480 mg, more than about 560 mg, or more than about 640 mg, including any range in between these values.

In certain embodiments. Azilsartan can be administered in conjunction with an antigen, vaccine, or anti-tumor preparation at a dosage of less than about 40 mg, less than about 30 mg, less than about 20 mg, or less than about 10 mg, including any range between these values. In certain embodiments. Azilsartan can be administered in conjunction with an antigen, vaccine, or anti-tumor preparation at a dosage of more than about 80 mg, more than about 100 mg, more than about 120 mg, more than about 140 mg, or more than about 160 mg, including any range in between these values.

Modes of Administration

Administration of the ARB or the compound of Formula (I) (e.g., Ondansetron and/or Alosetron) in conjunction with an antigen, vaccine, or anti-tumor preparation can be achieved by a variety of routes, including, e.g., topical application, inhalation, intravenous injection, application to a wound site, application to a surgical site, intracavitary injection, by suppository, subcutaneously, intradermally, transcutaneously, by nebulization, intraplurally, intraventricularly, intra-articularly, intraocularly, intraspinally, or by other methods well known to those of skill in the art. In certain embodiments, the ARB or the compound of Formula (I) (e.g., Ondansetron and/or Alosetron) and the antigen, vaccine, or anti-tumor preparation can be systemic after administration or may be localized by the use of regional administration, intramural administration, or use of an implant that acts to retain the active dose at the site of implantation. When the ARB or the compound of Formula (I) (e.g., Ondansetron and/or Alosetron) and the antigen, vaccine, or anti-tumor preparation are present in two separate pharmaceutical compositions, each composition can be administered through a different route or through the same route. In certain embodiments, the ARB or the compound of Formula (I) (e.g., Ondansetron and/or Alosetron) can be administered in conjunction with the antigen, vaccine, or anti-tumor preparation using any medically appropriate procedure, e.g. intravascular (intravenous, intraarterial, intracapillary) administration, injection into the cerebrospinal fluid, intracavity or direct injection in the brain. Intrathecal administration may be carried out through the use of an Ommaya reservoir, in accordance with known techniques. (F. Balis et al., Am J. Pediatr. Hematol. Oncol. 11, 74, 76 (1989). In certain embodiments, the ARB or the compound of Formula (I) (e.g., Ondansetron and/or Alosetron) can be administered in conjunction with the antigen, vaccine, or anti-tumor preparation prior to exposure of the individual to, e.g., an infectious agent, so that the resulting immune response upon subsequent exposure to the infectious agent can reduce the severity and/or duration of, e.g., the infection or disease caused by the infectious agent. In certain embodiments, an effective amount of the ARB or the compound of Formula (I) (e.g., Ondansetron and/or Alosetron) can be provided in one or more administrations. For example, where the antigen, vaccine, or anti-tumor preparation and the ARB or the compound of Formula (I) (e.g., Ondansetron and/or Alosetron) are provided in separate pharmaceutical compositions, an individual can receive the antigen, vaccine, or anti-tumor preparation and effective amount of an ARB or a compound of Formula (I) (e.g., Ondansetron and/or Alosetron), and then receive additional administrations of the ARB or the compound of Formula (I) (e.g., Ondansetron and/or Alosetron) 12 hours, 24 hours, 36 hours, 48 hours, and/or more than 48 hours after the initial administration.

For therapeutic treatment, in certain embodiments, the ARB or the compound of Formula (I) (e.g., Ondansetron and/or Alosetron) can be administered in conjunction with the antigen, vaccine, or anti-tumor preparation to an individual who is already exposed to the pathogen or has the infection or disease, e.g., cancer. The resulting enhanced immune response can reduce the duration and/or severity of the existing diseases or infection, as well as minimize any harmful consequences of untreated disease or infection. The ARB or the compound of Formula (I) (e.g., Ondansetron and/or Alosetron) can be administered in conjunction with the antigen, vaccine, or anti-tumor preparation along with any other therapeutic regimen.

Individuals Who can be Treated Using the Methods

Various individuals can be treated using the methods described herein. In certain embodiments, the individual who can be treated using the methods described above can be a patient.

In certain embodiments, an ARB (e.g., Losartan) or a combination of ARBs can be administered in conjunction with the antigen, vaccine, or anti-tumor preparation to individuals who are otherwise not receiving an ARB for treatment of a pre-existing condition. As noted elsewhere herein, ARBs can be prescribed for the treatment and/or prevention of a variety of diseases. Accordingly, it will be appreciated by one of skill in the art that an individual on whom any method of the invention is practiced does not have, e.g., congestive heart failure, chronic heart failure, hypertension, diabetic neuropathy, migraine, a predisposition to myocardial infarction, or any other condition for which ARBs are indicated, or is not otherwise in need of treatment. An individual who has a condition or disease described herein can receive an ARB in conjunction with an antigen for the purpose of enhancing an immune response if the individual is not being treated with an ARB.

In certain embodiments, a compound of Formula (I) (e.g., Ondansetron or Alosetron), or a combination of compounds of Formula (I) can be administered in conjunction with the antigen, vaccine, or anti-tumor preparation. In certain embodiments, a compound or combination of compounds of Formula (I) (e.g., Ondansetron and/or Alosetron) can be administered in conjugation with an antigen, vaccine, or anti-tumor preparation to individuals who are otherwise not receiving Ondansetron and/or Alosetron for treatment of a pre-existing condition. As noted elsewhere herein, Ondansetron and/or Alosetron can be prescribed for the treatment and/or prevention of a variety of diseases. Accordingly, it will be appreciated by one of skill in the art that an individual on whom any method of the invention is practiced does not have, e.g., irritable bowel syndrome (IBS), post-operative nausea and vomiting (PONV), radiation-induced nausea and vomiting (RINV), chemotherapy-induced nausea and vomiting (CINV), or is not otherwise in need of Ondansetron treatment and/or Alosetron treatment. An individual who has a condition or disease described herein, or is otherwise in need of treatment, can receive Ondansetron, Alosetron in conjunction with an antigen, vaccine, or anti-tumor preparation for the purpose of enhancing an immune response if the individual is not being treated with Ondansetron and/or Alosetron.

Alternatively, in some embodiments, the individuals who are being treated with Ondansetron and/or Alosetron can temporarily suspended Ondansetron and/or Alosetron treatment. For example, an individual who is being treated with Ondansetron and/or Alosetron can receive Ondansetron, Alosetron, and/or a combination of compounds of Formula (I) comprising Ondansetron and/or Alosetron in conjunction with an antigen, vaccine, or anti-tumor preparation if the individual has taken Ondansetron and/or Alosetron more than about 1 hour, more than about 3 hours, more than about 6 hours, more than about 12 hours, more than about 18 hours, more than 24 hours, more than 1 day more than 2 days, more than 3 days, more than 4 days, more than 5 days, more than 6 days, more than 1 week, more than 3 weeks, more than 1 month, more than three months, more than 6 months, or more than 1 year before receiving Ondansetron, Alosetron, and/or a combination of compounds of Formula (I) comprising Ondansetron and/or Alosetron in conjunction with the antigen, including any range in between these values. Individuals receiving Ondansetron and/or Alosetron therapy can temporarily suspend treatment prior to being administered Ondansetron, Alosetron, and/or a combination compounds of Formula (I) comprising Ondansetron and/or Alosetron in conjunction with an antigen, vaccine, or anti-tumor preparation for the purpose of enhancing an immune response, inhibiting monocyte migration to a lymph node, amplifying vaccine immunity, or treating cancer. For example, blood and/or urine samples provided by such an individual can be assayed for the presence of Ondansetron and/or Alosetron (and/or its metabolites) using chromatographic or spectroscopic methods described elsewhere herein. The methods of the invention can be practiced on the individual once it has been determined that Ondansetron and/or Alosetron (and/or its metabolites) is undetectable in the individual's blood and/or urine. Such methods are described elsewhere herein.

Similarly, in some embodiments, the individuals who are being treated with an ARB can temporarily suspended ARB treatment. For example, an individual who is being treated with an ARB for a pre-existing condition can receive an ARB in conjunction with an antigen, vaccine, or anti-tumor preparation if the individual has taken the ARB more than about 1 hour, more than about 3 hours, more than about 6 hours, more than about 12 hours, more than about 18 hours, more than 24 hours, more than 1 day more than 2 days, more than 3 days, more than 4 days, more than 5 days, more than 6 days, more than 1 week, more than 3 weeks, more than 1 month, more than three months, more than 6 months, or more than 1 year before receiving the ARB in conjunction with the antigen, including any range in between these values. Alternatively, in some embodiments, an individual who is being treated with an ARB for a pre-existing condition can suspend ARB treatment and be tested, using methods well known in the art, to determine that the individual does not have a detectable level of an ARB in their blood and/or urine prior to the administration of the ARB in conjunction with the antigen, the vaccine, or the anti-tumor preparation. For example, blood and/or urine samples provided by such an individual can be assayed for the presence of an ARB (and/or its metabolites) using chromatographic or spectroscopic methods described elsewhere herein. The methods of the invention can be practiced on the individual once it has been determined that the ARB (and/or its metabolites) is undetectable in the individual's blood and/or urine. Such methods are described elsewhere herein.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Losartan Blocked Canine and Human Monocyte Migration In Vitro

Boyden Chamber Assay.

The Boyden chamber assay is based on a chamber of two medium-filled compartments separated by a microporous membrane. In general, cells are placed in the upper compartment and are allowed to migrate through the pores of the membrane into the lower compartment, in which chemotactic agents are present. After an appropriate incubation time, the membrane between the two compartments is fixed and stained, and the number of cells that have migrated to the lower side of the membrane is determined. Experiments using this assay were performed as described in Mitchell et al. (2012) Int. Immunopharmacol. 15: 357-363 to assess the migration of monocytes.

Figure 2:
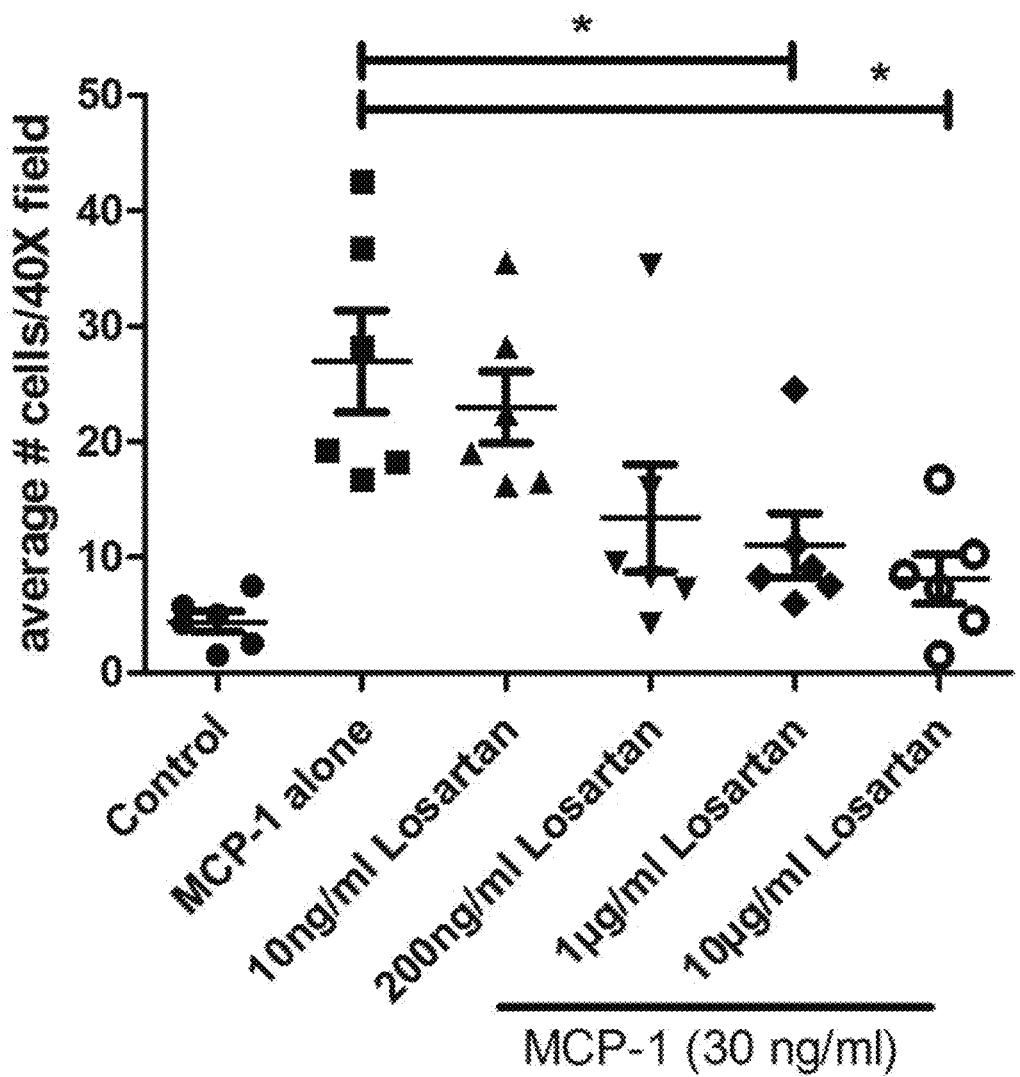
FIG. 2 shows the results of experiments conducted to assess the ability of Losartan to inhibit canine monocyte migration in vitro.

A Boyden chamber assay was performed to assess the migration of dog monocytes and of human monocytes (i.e., the human monocyte cell line THP-1) in response to a CCL2 (MCP-1) gradient and to assess the ability of Losartan to inhibit monocyte migration in vitro. As shown in FIG. 1, Losartan potently blocked human monocyte migration (THP-1) in vitro in a dose dependent manner at concentrations easily achievable in vivo (hpf=high power field). The asterisk in FIG. 1 indicates statistical differences, i.e., a p-value<0.05. FIG. 2 shows that Losartan potently blocked canine monocyte migration in vitro in a dose dependent manner at concentrations easily achievable in vivo. The asterisks in FIG. 2 indicate statistical differences, i.e., a p-value<0.05. Moreover, at concentrations of 1 μg/ml and 10 μg/ml, Losartan blocked canine monocyte migration even in the presence of MCP-1. Taken together, these results indicate that Losartan is an inhibitor of monocyte migration in vitro.

Example 2

Ondansetron Blocked Human Monocyte Migration In Vitro

Figure 3:
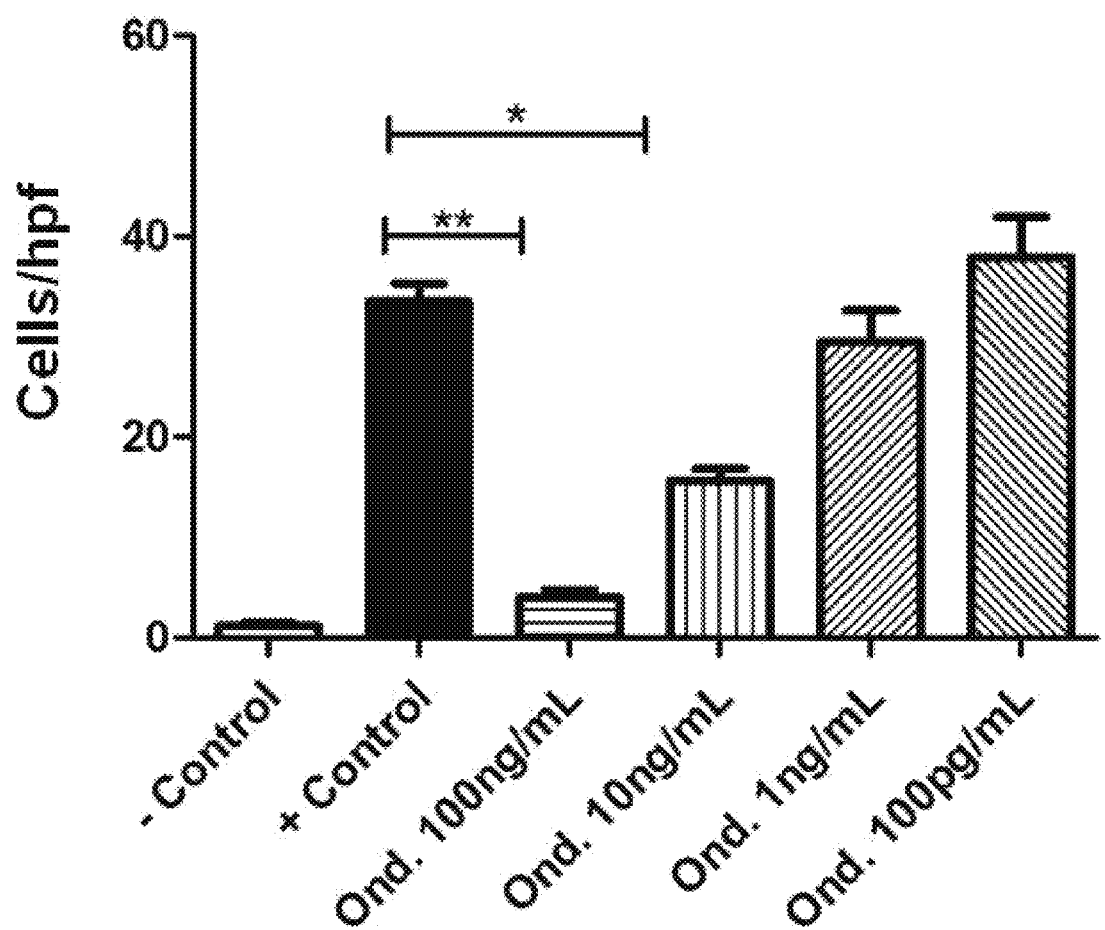
FIG. 3 shows the results of experiments conducted to assess the ability of Ondansetron to inhibit human monocyte migration in vitro.

A Boyden chamber assay was performed (as described in Mitchell et al. (2012) Int. Immunopharmacol, supra) to assess the migration of human monocytes (i.e., the human monocyte cell line THP-1) in response to a CCL2 (MCP-1) gradient and to assess the ability of Ondansetron to inhibit monocyte migration in vitro. As shown in FIG. 3, Ondansetron potently blocked THP-1 monocyte migration in vitro in a dose dependent manner at concentrations easily achievable in vivo. The single asterisk in FIG. 3 indicates statistical differences, i.e., a p-value<0.05. The double asterisks in FIG. 3 indicates statistical differences, i.e., a p-value<0.01. These results indicate that Ondansetron is an inhibitor of monocyte migration in vitro.

Example 3

Ondansetron Treatment Inhibited Monocyte Migration to Lymph Nodes in Mice

Footpad inflammation-induced monocyte migration assays were performed as previously described (Mitchell et al. (2012), J. Immunology 189: 5612-5621) to determine whether Ondansetron inhibits monocyte migration in vivo in mice. Briefly, two groups of mice (n=4 per group) were injected with 50 μl of liposomal vaccine adjuvant in one footpad. The first group of mice was treated by injection of 3 mg/kg Ondansetron administered IP at the time of footpad injection and the Ondansetron injections were repeated 12, 24, and 36 hours following footpad injection. The second group of mice did not receive any additional treatment. The third group received neither the vaccine nor the Ondansetron. Inflammatory monocyte migration to the draining popliteal lymph nodes was assessed in all three groups of mice via flow cytometry (as described in Mitchell et al. (2012), J. Immunology, supra) 24 hours following vaccination.

Figure 4:
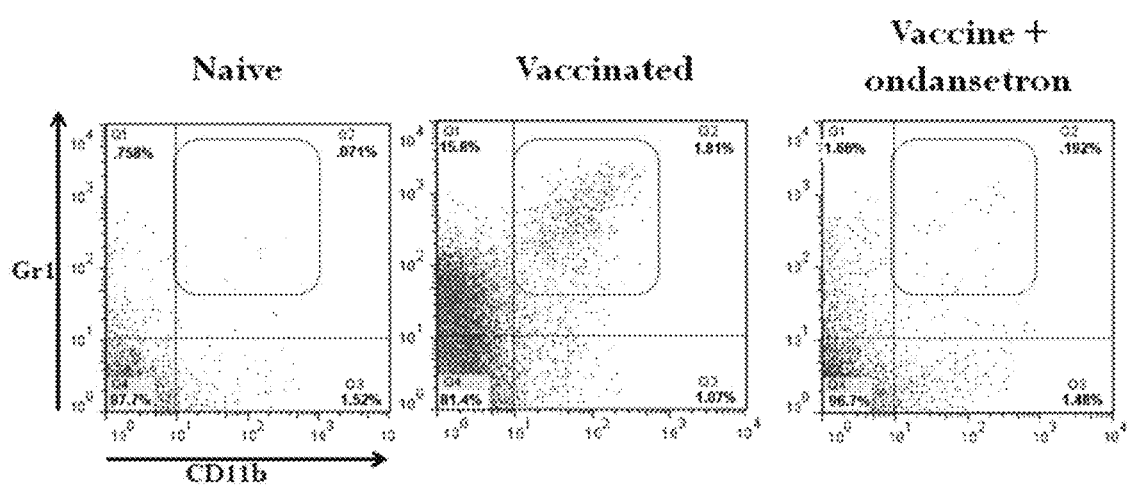
FIG. 4 shows the results of experiments conducted to determine the effect of Ondansetron treatment on the migration of immune suppressive inflammatory monocytes to lymph nodes following vaccination in mice.
Figure 5:
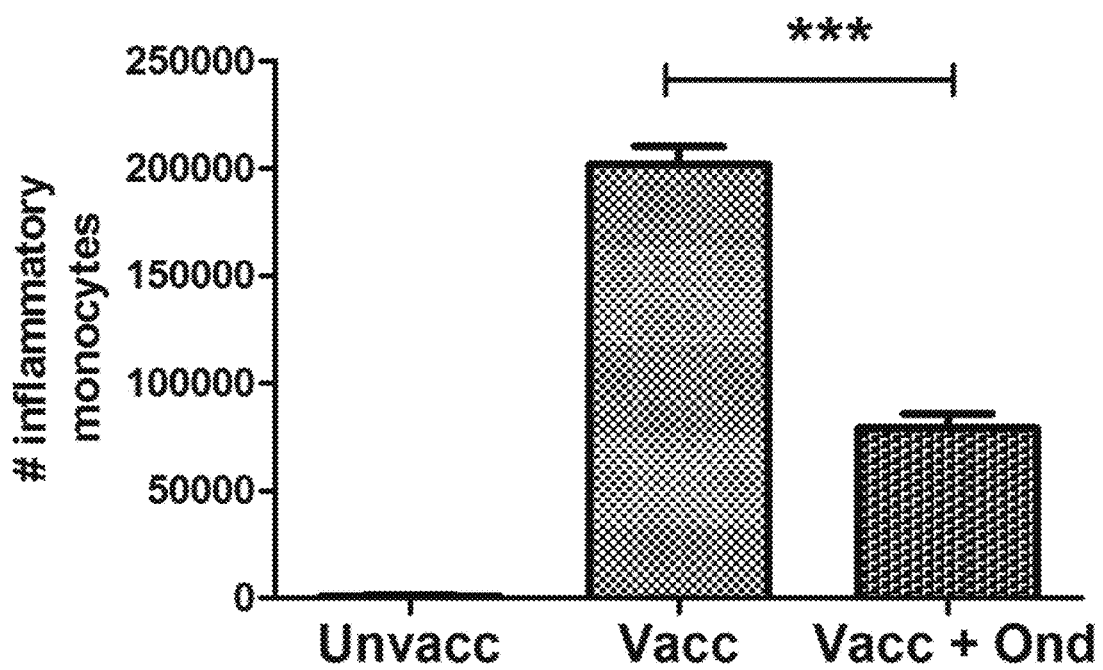
FIG. 5 provides a quantitative analysis of the results shown in FIG. 4.

As shown in FIG. 4, the migration of inflammatory monocytes to the draining lymph nodes was significantly reduced in mice who received Ondansetron in conjunction with the vaccine as compared to mice who received no additional treatment with vaccination. FIG. 5 provides a quantitative analysis of the results depicted in FIG. 4. The triple asterisks in FIG. 5 indicates statistical differences, i.e., a p-value<0.001. These results indicate that Ondansetron acts as a potent inhibitor of inflammatory monocyte migration in vivo.

Example 4

Losartan Treatment Inhibited Monocyte Migration to Lymph Nodes in Mice

Footpad inflammation-induced monocyte migration assays were performed as described previously (as described in Mitchell et al. (2012), J. Immunology, supra) to determine whether Losartan inhibits monocyte migration in vivo in mice. Briefly, two groups of mice (n=4 per group) were vaccinated in the right rear footpad. The first group of mice was treated by injection of 30 mg/kg Losartan at the time of injection and 12 hours following injection. The second group of mice did not receive any additional treatment. Inflammatory monocyte migration to the draining popliteal lymph nodes was assessed in all three groups of mice via flow cytometry (as described in Mitchell et al. (2012), J. Immunology, supra) 24 hours following vaccination.

Figure 6:
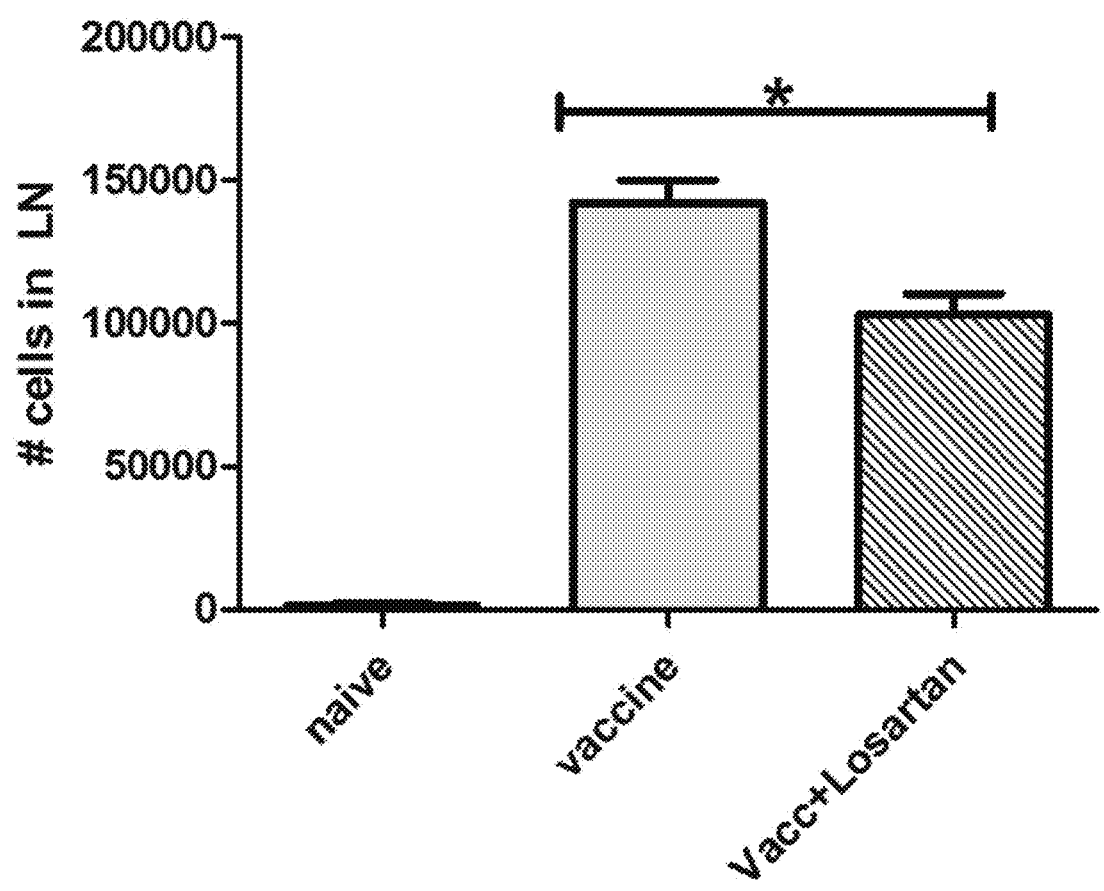
FIG. 6 shows the results of experiments conducted to determine the effect of Losartan treatment on the migration of immune suppressive inflammatory monocytes to lymph nodes following vaccination in mice.

As shown in FIG. 6, the migration of inflammatory monocytes to the draining lymph nodes was significantly reduced in mice who received Losartan in conjunction with the vaccine as compared to mice who received no additional treatment with vaccination. The asterisk in FIG. 6 indicates statistical differences, i.e., a p-value<0.05. These results indicate that Losartan acts as a potent inhibitor of inflammatory monocyte migration in vivo.

Example 5

Losartan Treatment Inhibited Monocyte Migration to Lymph Nodes in Dogs

Figure 7A:
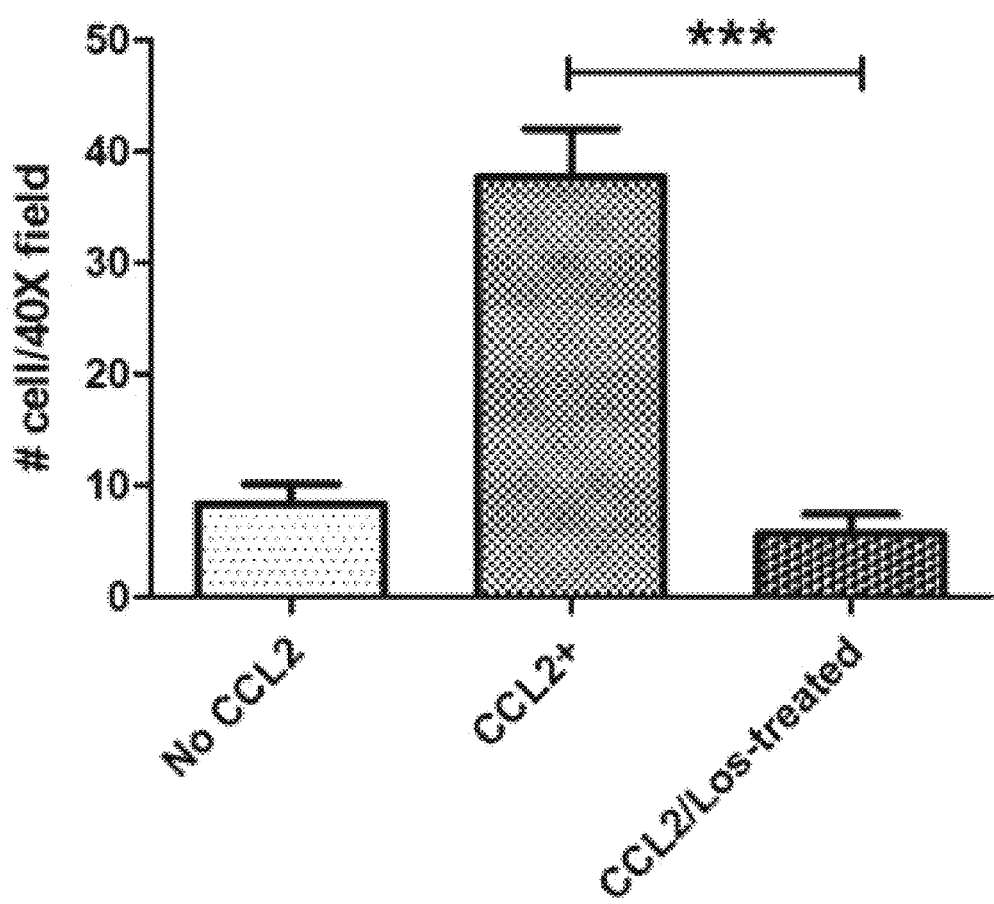
FIGS. 7a and 7b show the results of experiments conducted to determine the effect of Losartan treatment on the migration of circulating immune suppressive inflammatory monocytes in healthy dogs. (a) and (b) show the results from two different dogs.
Figure 7B:
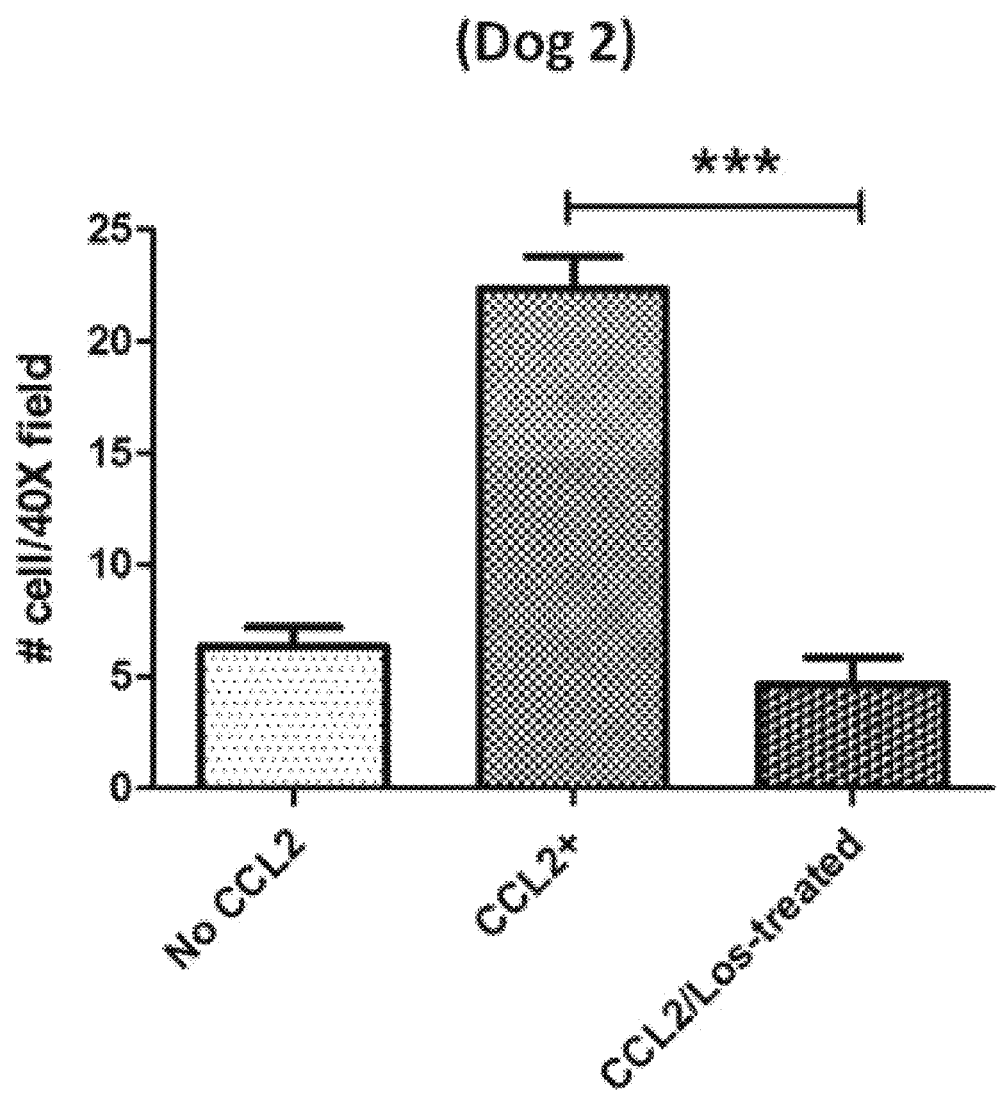
Figure 8:
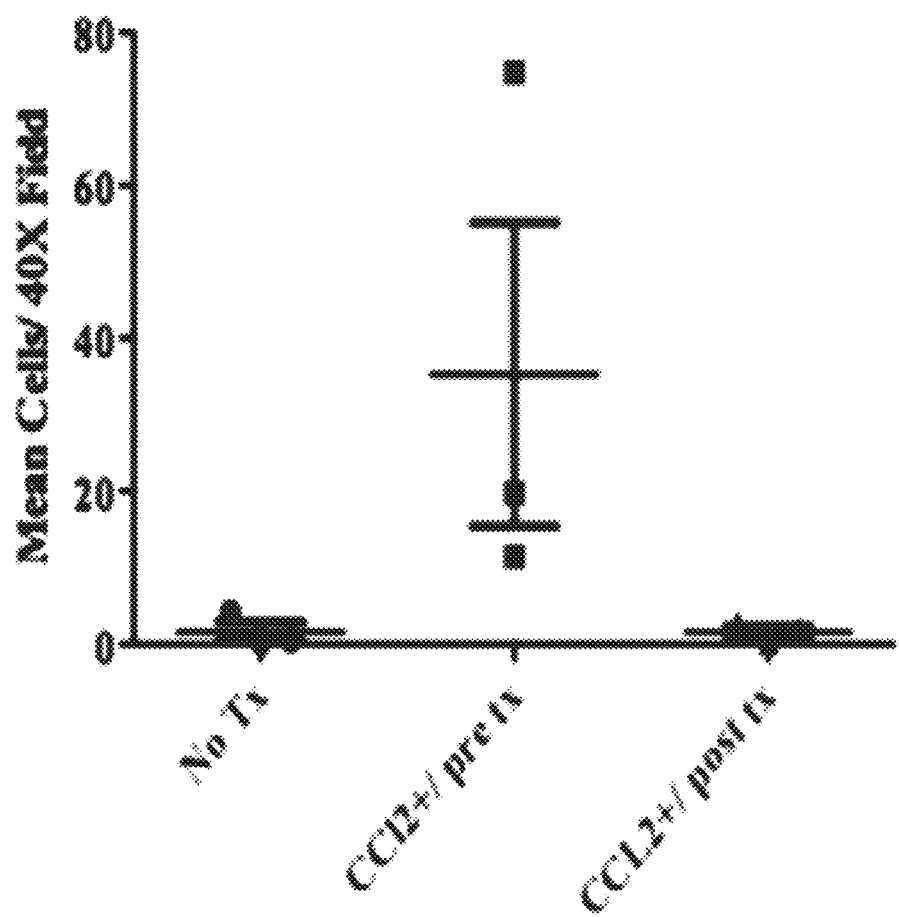
FIG. 8 shows the results of experiments conducted to determine the effect of Losartan treatment on the migration of circulating immune suppressive inflammatory monocytes in dogs with cancer.

To determine whether Losartan inhibits monocyte migration in vivo, dogs [n=2] were treated with Losartan at 2 mg/kg/day for 48 hours. Blood samples were then taken from the dogs, and Boyden chamber assays were performed as described previously (Mitchell et al. (2012) Int. Immunopharmacol, supra) As shown in FIG. 7(a and b), monocyte migration was significantly inhibited in blood samples obtained from the dogs after Losartan treatment (FIG. 7a shows dog 1, FIG. 7b shows dog 2; the left panel is a no migration control, the middle panel shows monocyte migration prior to losartan treatment, and the right panel shows monocyte migration after 48 hours of Losartan treatment). The triple asterisks in FIGS. 7a and 7b indicate statistically significant differences (p<0.05). This experiment was repeated in 3 dogs with cancer. Briefly, each of the three dogs was treated for two weeks with 2 mg/kg/day Losartan before the Boyden chamber assay was performed. FIG. 8 provides the results of pooled monocyte migration data (the left panel is a no migration control, the middle panel shows monocyte migration prior to Losartan treatment, and the right panel shows monocyte migration after 2 weeks of Losartan treatment). Monocyte migration was inhibited in blood samples obtained from the 3 dogs with cancer who had been receiving Losartan treatment for two weeks. Taken together, these results indicate that Losartan treatment at a concentration of 2 mg/kg/day for at least 48 hours can inhibit monocyte migration in vivo.

Example 6

Losartan Treatment at Time of Vaccination Significantly Improved Humoral and Cellular Immunity To assess the effects of Losartan on humoral immunity, mice were treated with Losartan at the time of vaccination. Briefly, two groups of mice (n=5) were vaccinated with 5 µg of ovalbumin. The first group of mice received 30 mg/kg Losartan via injection at the time of vaccination, and at 12, 24, and 36 hours following vaccination. The second group of mice received no additional treatment following vaccination. Second vaccinations were repeated 10 days following the initial vaccinations. Second Losartan treatments were repeated for the first group of mice as described. Anti-ovalbumin antibodies from each group of mice were titered (as described in Mitchell et al. (2012), J. Immunology, supra) to assess the degree to which humoral immunity was enhanced in the mice receiving Losartan treatment.

Figure 9:
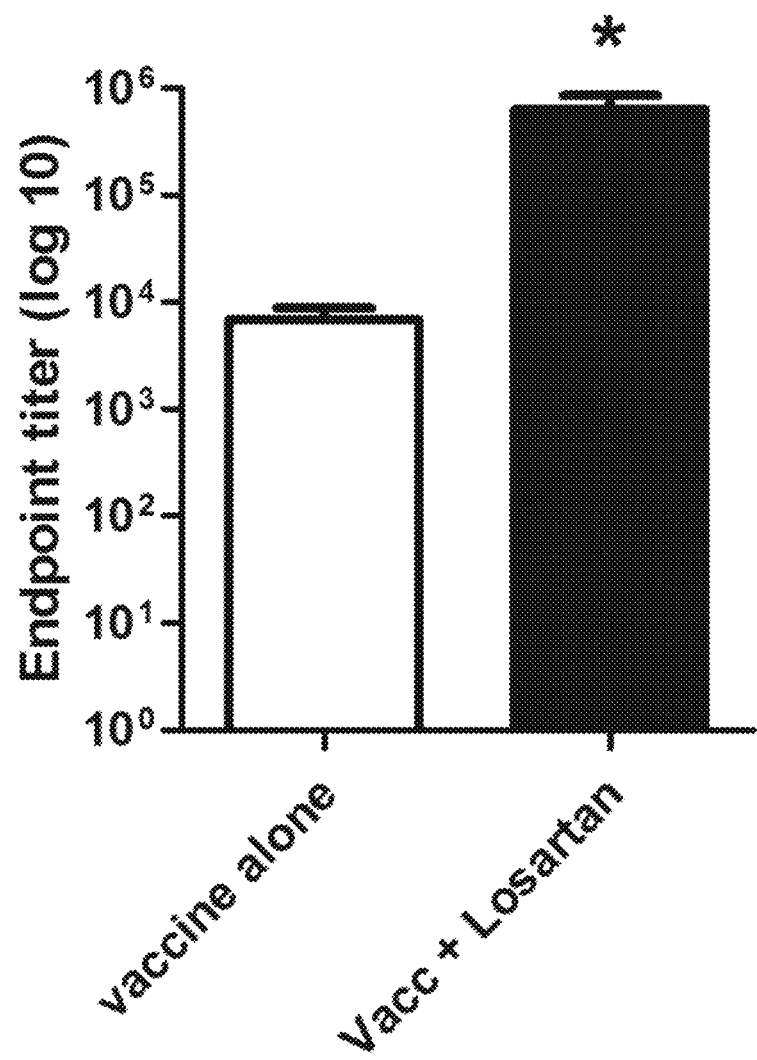
FIG. 9 shows the results of experiments conducted to determine the effect of Losartan treatment on a humoral immune response.

As shown in FIG. 9, mice treated with Losartan were found to have significantly higher anti-ovalbumin antibody titers than mice who received no additional treatment with vaccination, indicating that administration of Losartan in conjunction with the antigen ovalbumin enhanced humoral immunity. The asterisk in FIG. 9 indicates statistical differences, i.e., a p-value<0.05.

Example 7

Ondansetron Treatment at Time of Vaccination Significantly Improved Humoral Immunity To assess the effects of Ondansetron on humoral immunity, mice were treated with Ondansetron at the time of vaccination. Briefly, two groups of mice (n=4 per group) were vaccinated subcutaneously with 1 µg of ovalbumin in a liposomal adjuvant. The first group of mice received 3 mg/kg Ondansetron via i.p. injection at the time of vaccination, and at 12, 24, and 36 hours following vaccination. The second group of mice received no additional treatment following vaccination. A third group of mice received neither the vaccine nor the Ondansetron. Second vaccinations were repeated for the first two groups of mice 10 days following the initial vaccinations, and second Ondansetron treatments were repeated for the groups as described for the first cycle of vaccination. Anti-ovalbumin antibodies from each group of mice were titered (as described in Mitchell et al. (2012), J. Immunology, supra) to assess the degree to which humoral immunity was enhanced in the mice receiving Ondansetron treatment.

Figure 10:
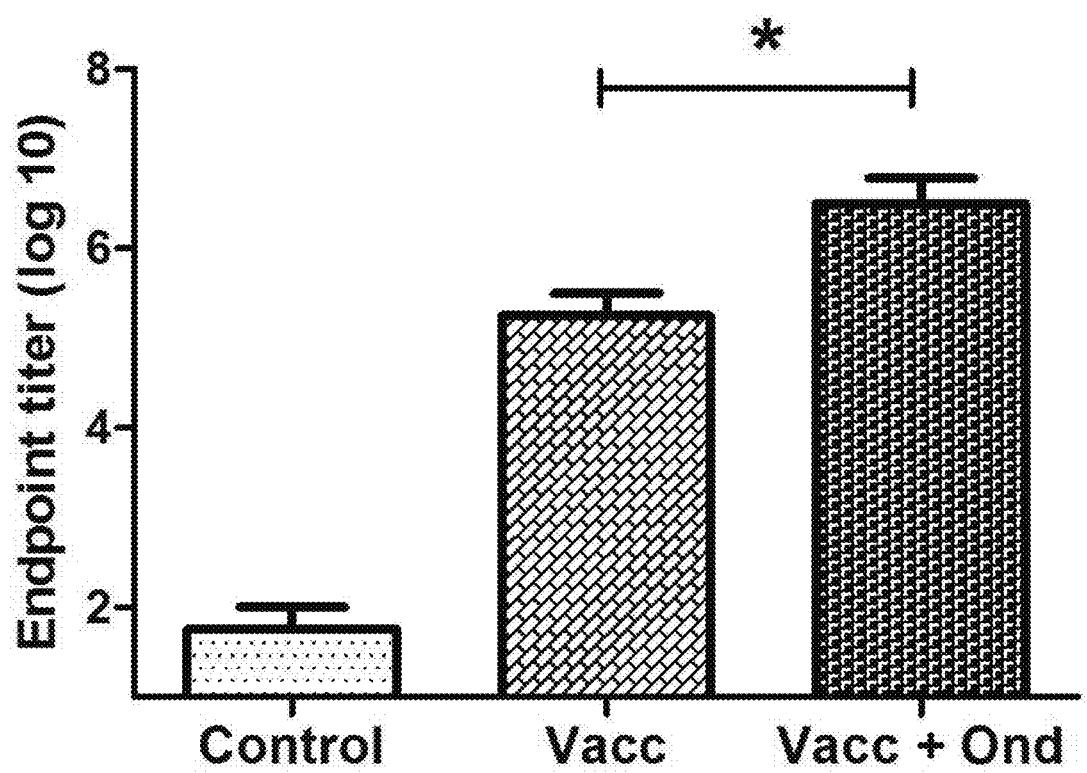
FIG. 10 shows the results of experiments conducted to determine the effect of Ondansetron treatment on a humoral immune response.

As shown in FIG. 10, mice treated with Ondansetron were found to have significantly higher anti-ovalbumin antibody titers than mice who received no additional treatment with vaccination, indicating that administration of Ondansetron in conjunction with the antigen ovalbumin enhanced humoral immunity. The asterisk in FIG. 10 indicates indicate statistical differences, i.e., a p-value<0.05.

Example 8

Losartan Amplifies Vaccine Cellular Immunity

Two groups of mice were immunized as noted in Example 7 above. To determine whether cellular immunity was enhanced in the Losartan-treated mice, mice from both the first and second groups were euthanized, and their spleen cells were assayed to determine IFNγ secretion levels in response to ovalbumin restimulation. Splenectomies and restimulation assays for cellular immune responses were performed as previously described (Mitchell et al. (2012), J. Immunology, supra). Spleen cells were restimulated in vitro for 72 hours with 5 µg/ml ovalbumin protein.

Figure 11:
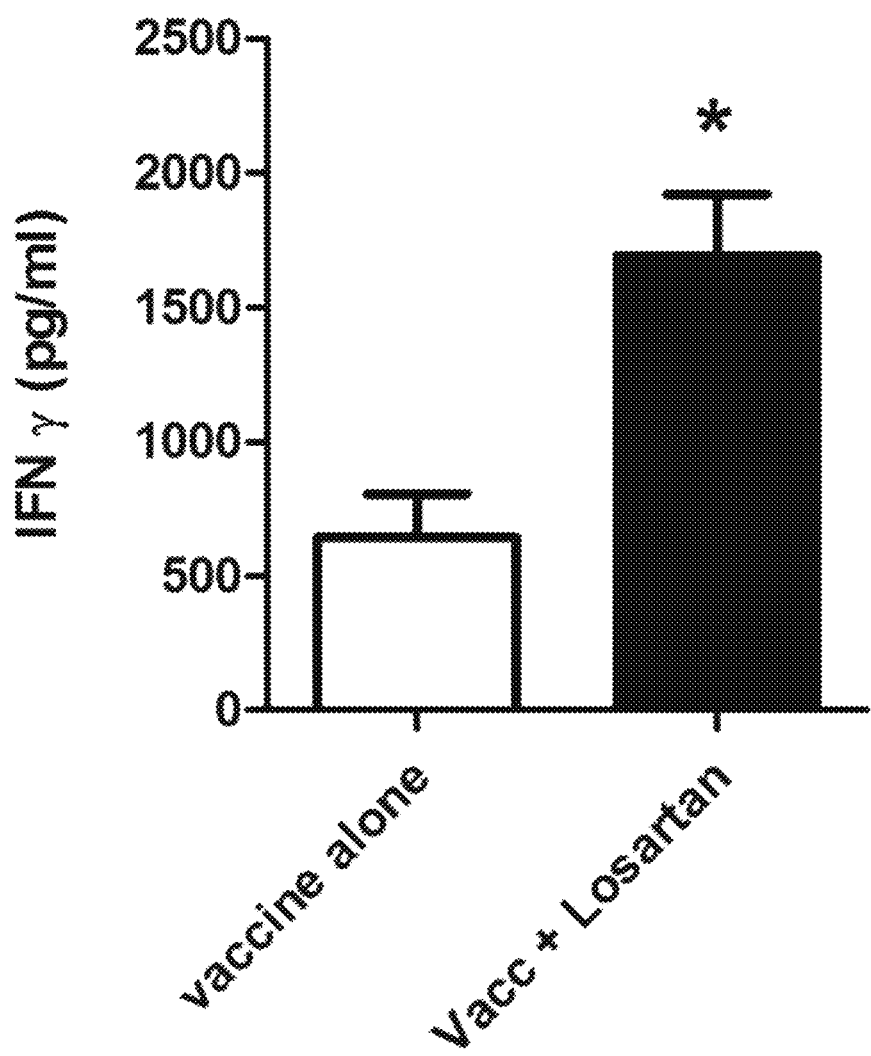
FIG. 11 shows the results of experiments conducted to determine the effect of Losartan treatment on a cellular immune response.

As shown in FIG. 11, spleen cells from mice that were vaccinated and treated concurrently with Losartan produced significantly more IFNγ, indicating a significant increase in T cell responses to vaccination when losartan was administered in conjunction with the antigen ovalbumin. The asterisks in FIG. 11 indicate statistical differences, i.e., a p-value<0.05.

Example 9

Ondansetron Administration Enhanced Tumor Vaccine Responses

The A20 mouse B-cell lymphoma model was used to assess the effects of Ondansetron on tumor vaccine responses. Briefly, two groups of mice (n=5 per group) with established d3 A20-HA tumors (i.e., tumors expressing HA) were vaccinated weekly for 3 weeks with HA antigen (1 µg per mouse in liposome adjuvant), either without or with concurrently administered ondansetron (3 mg/kg i.p., administered 4 times at 12 h intervals). A third group of mice received neither the HA nor the Ondansetron. Tumor measurements were made using calipers every 2-3 days. Mice were sacrificed when their tumors reached a diameter of 1.5 cm.

Figure 12:
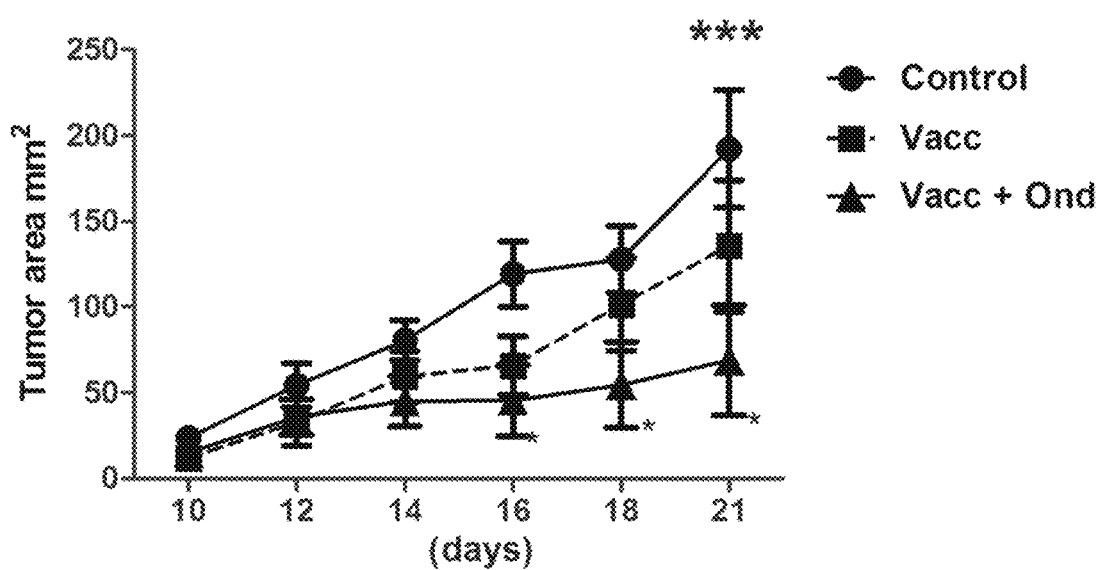
FIG. 12 shows the results of experiments conducted to determine the effect of Ondansetron on tumor vaccine responses.

As shown in FIG. 12, tumor growth rates were significantly reduced in the mice that received the vaccine in conjunction with the Ondansetron, as compared to tumor growth rates in mice that received only the vaccine. The triple asterisks in FIG. 12 indicate statistical differences, i.e., a p-value<0.001. Single asterisks indicate that there are statistically significant differences in tumor sizes between the group of mice who had received Ondansetron and the vaccine and the group of mice that received only the vaccine.

Figure 13:
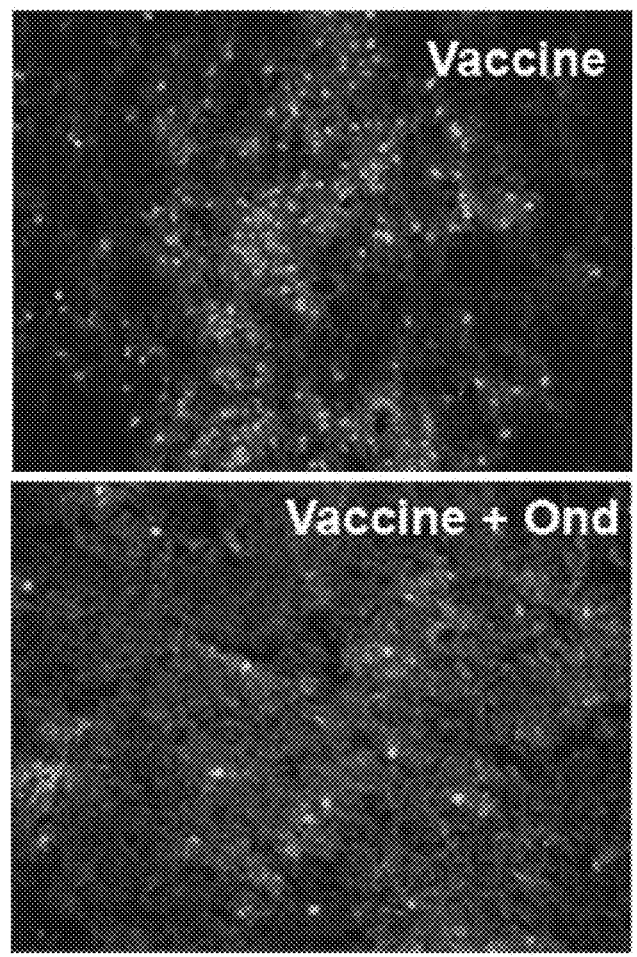
FIG. 13 shows the results of experiments conducted to determine the effect of Ondansetron treatment on myeloid cell accumulation in tumor tissues following vaccination.

FIG. 13 shows tumor tissues from a mouse that received only the vaccine (top panel) and tumor tissues from a mouse that received vaccine in conjunction with Ondansetron (bottom panel) that were evaluated via immunohistochemistry. Labeled anti-CD11b antibodies were used to quantitate the numbers of infiltrating CD11b+ monocyte/macrophages in the tumor tissues. Tumors of mice treated with ondansetron had markedly fewer monocyte/macrophages than tumors of mice that received the vaccine alone. Taken together, the results provided in FIGS. 12 and 13 demonstrate that administering Ondansetron in conjunction with an anti-tumor vaccine reduced inflammatory monocyte migration into tumor tissues and reduced tumor growth.

Example 10

Synergistic Combination of Losartan and Sunitinib

To assess the effect of a Losartan/Sunitinib combination therapy approach for tumor treatment, tumors were seeded in mice (BALB/c, n=5 per group) via intravenous injection with $2.5 \times 10^5$ K7M2 osteosarcoma cells expressing a luciferase reporter gene. Three days later, treatment was started with losartan (6 mg/kg, i.p. BID) and sunitinib (0.8 mg/kg, ip, once daily for 5 days on, 2 off). Drugs were injected separately. Tumor growth was monitored by IVIS imaging every 2-3 days.

Figure 14:
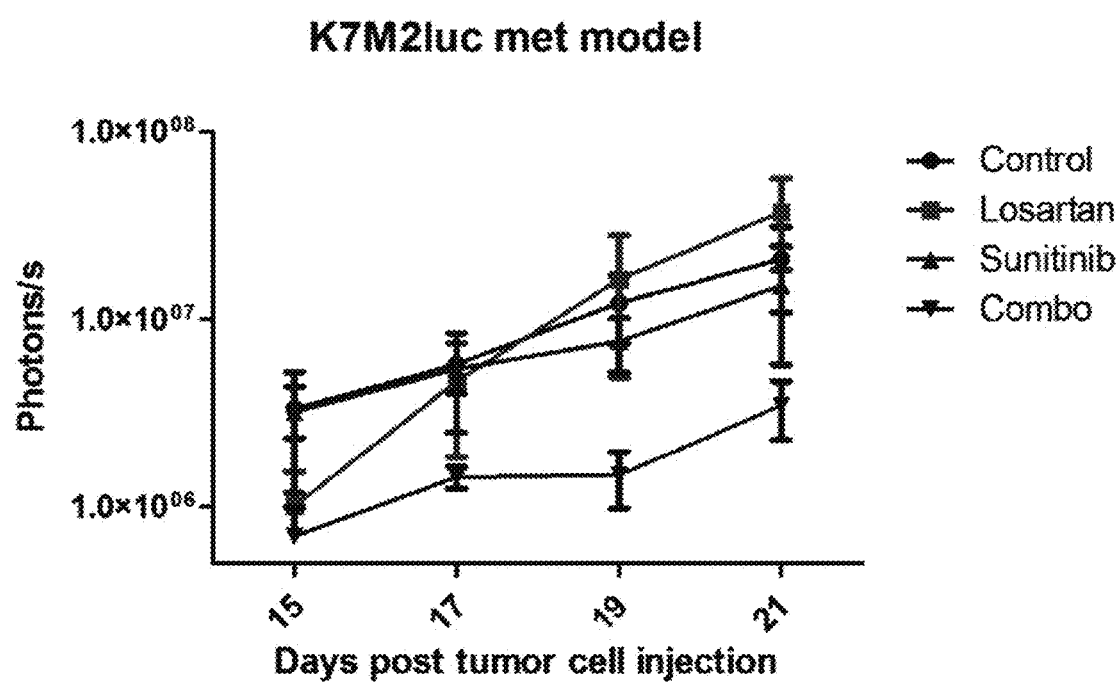
FIG. 14 shows the results of an experiment conducted to determine the synergistic interactions between losartan and sunitinib for inhibiting tumor growth.
Figure 15A:
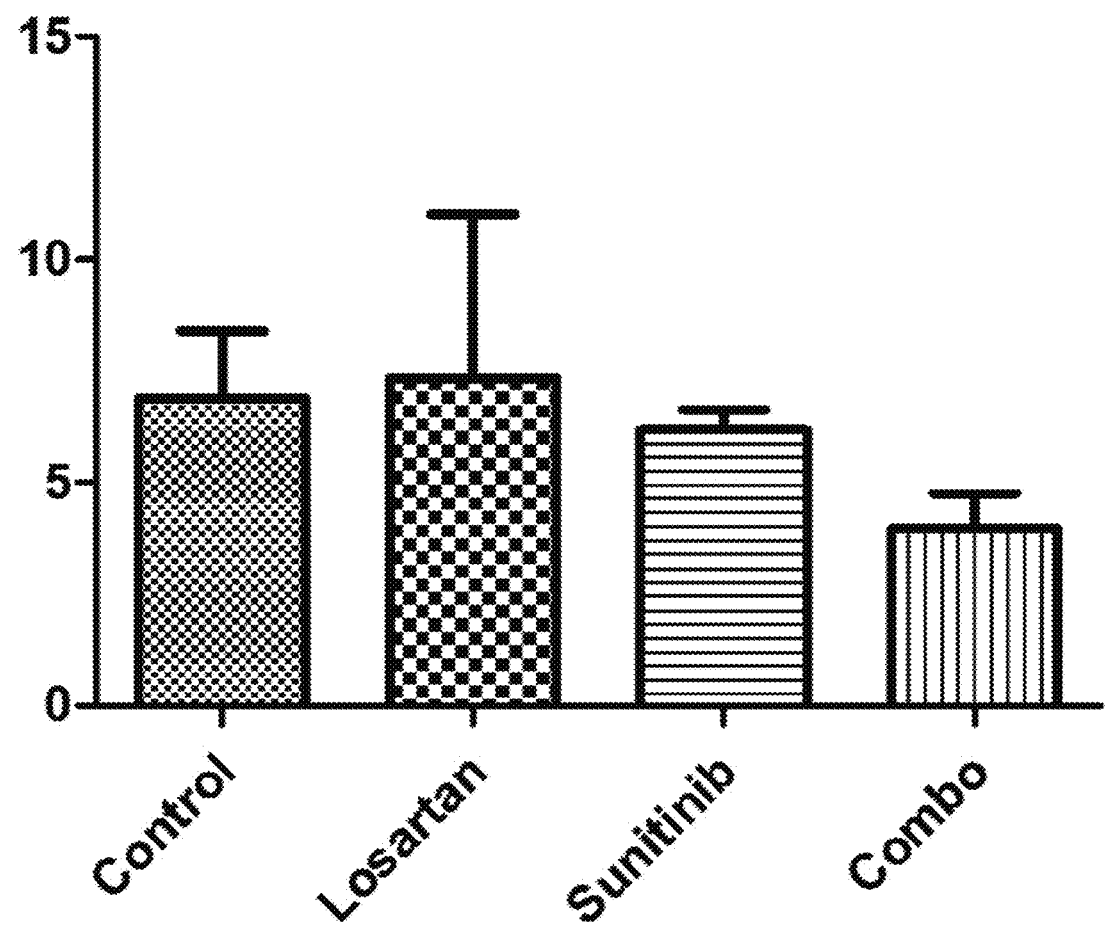
FIGS. 15a and 15b show the results of preliminary experiments conducted to determine the synergistic interactions between losartan and sunitinib for inhibiting monocyte migration. (a) shows the percentage of CD11 b+Ly6C+ monocytes present in the lungs of the mice having lung metastases. (b) shows the frequency of PDL1+ monocytes to total cells present in the lungs of the mice having lung metastases.
Figure 15B:
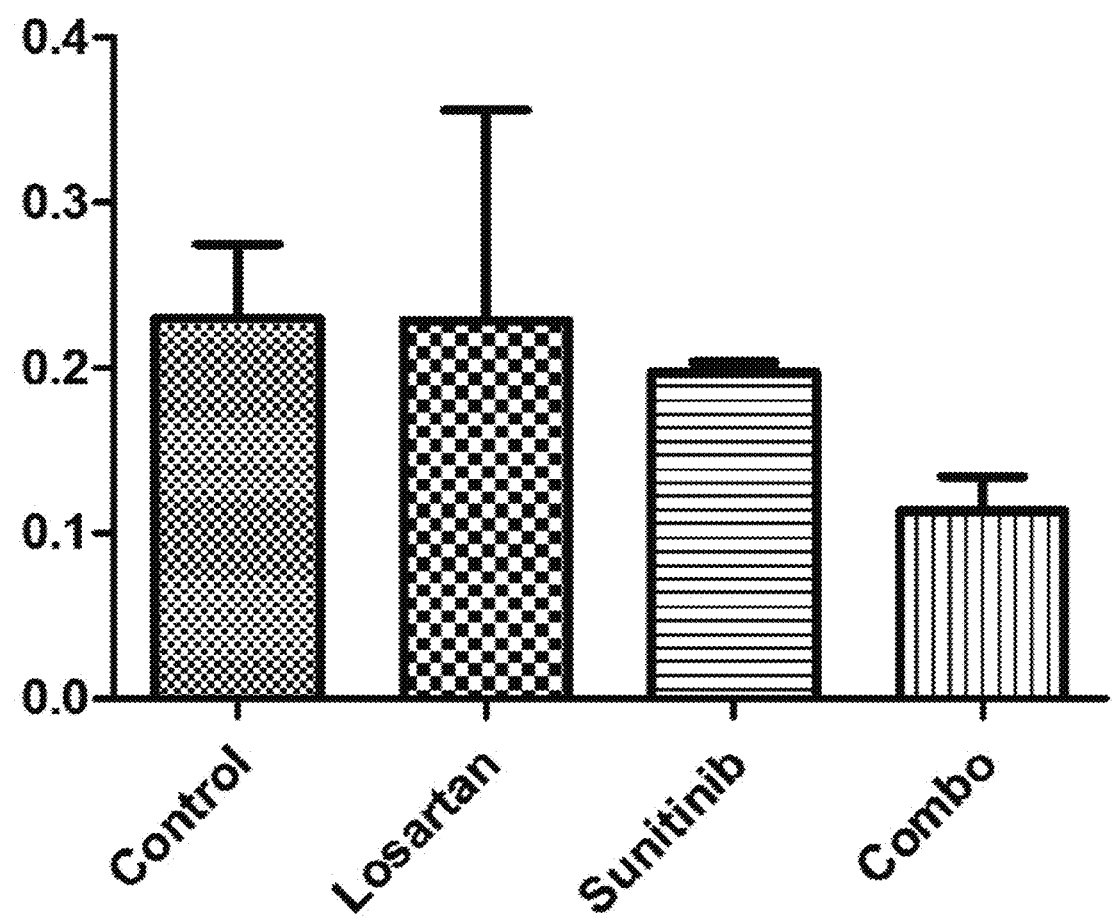

As shown in FIG. 14, tumors in mice receiving the Losartan/Sunitinib combination, had a decreased rate of growth as compared to mice receiving Losartan or Sunitinib alone (data not significant), suggesting that these drugs may interact synergistically to suppress tumor growth and metastasis. At the completion of the experiment, all animals were euthanized and lung tissues collected to evaluate myeloid cell responses by flow cytometry. FIG. 15(a) shows the percentage of CD11b+/Ly6C+ monocytes, as compared to total monocytes present in the lungs of these mice, and FIG. 15(b) shows the percentage of CD11b+/Ly6C+/PDL1+ monocytes compared to the total cells present in the lungs of these mice. Using each of these metrics, a trend was observed suggesting that Losartan/Sunitinib combination results in a synergistic inhibition of monocyte migration to the lung tissue having tumors.

All of the U.S. patents, U.S. patent application publications, U.S. patent applications, PCT patent application, PCT patent application publications, foreign patents, foreign patent applications and non-patent publications referred to in this specification or listed in any Application Data Sheet are incorporated herein by reference in their entirety. From the foregoing it will be appreciated that, although specific embodiments of the invention have been described herein for purposes of illustration, various modifications may be made without deviating from the spirit and scope of the invention.

REFERENCES CITED

1. Bronte V. Myeloid-derived suppressor cells in inflammation: Uncovering cell subsets with enhanced immunosuppressive functions. Eur J Immunol 2009.
2. Condamine T. Gabrilovich D I. Molecular mechanisms regulating myeloid-derived suppressor cell differentiation and function. Trends Immunol 2011; 32:19-25.
3. Diaz-Montero C M, Salem M L, Nishimura M I, et al. Increased circulating myeloid-derived suppressor cells correlate with clinical cancer stage, metastatic tumor burden, and doxorubicin-cyclophosphamide chemotherapy. Cancer Immunol Immunother 2009; 58:49-59.
4. Gabrilovich D I, Nagaraj S. Myeloid-derived suppressor cells as regulators of the immune system. Nat Rev Immunol 2009; 9:162-174.
5. Almand B, Clark J I, Nikitina E, et al. Increased production of immature myeloid cells in cancer patients: a mechanism of immunosuppression in cancer. J Immunol 2001; 166:678-689.
6. Mantovani A. Molecular pathways linking inflammation and cancer. Curr Mol Med 2010; 10:369-373.
7. Ostrand-Rosenberg S, Sinha P. Myeloid-derived suppressor cells: linking inflammation and cancer. J Immunol 2009; 182:4499-4506.
8. Pollard J W. Tumour-educated macrophages promote tumour progression and metastasis. Nat Rev Cancer 2004; 4:71-78.
9. Serafini P, Borrello I, Bronte V. Myeloid suppressor cells in cancer: recruitment, phenotype, properties, and mechanisms of immune suppression. Semin Cancer Biol 2006; 16:53-65.
10. Youn J I, Gabrilovich D I. The biology of myeloid-derived suppressor cells: the blessing and the curse of morphological and functional heterogeneity. Eur J Immunol 2010; 40:2969-2975.
11. Ostrand-Rosenberg S, Sinha P, Danna E A, et al. Antagonists of tumor-specific immunity: tumor-induced immune suppression and host genes that co-opt the anti-tumor immune response. Breast Dis 2004; 20:127-135.
12. Kusmartsev S, Su Z, Heiser A, et al. Reversal of myeloid cell-mediated immunosuppression in patients with metastatic renal cell carcinoma. Clin Cancer Res 2008; 14:8270-8278.
13. Gazzaniga S, Bravo A I, Guglielmotti A, et al. Targeting tumor-associated macrophages and inhibition of MCP-1 reduce angiogenesis and tumor growth in a human melanoma xenograft. J Invest Dermatol 2007; 127:2031-2041.
14. De Santo C, Serafini P, Marigo I, et al. Nitroaspirin corrects immune dysfunction in tumor-bearing hosts and promotes tumor eradication by cancer vaccination. Proc Natl Acad Sci USA 2005; 102:4185-4190.
15. Sica A. Role of tumour-associated macrophages in cancer-related inflammation. Exp Oncol 2010; 32:153-158.
16. Solinas G, Marchesi F, Garlanda C, et al. Inflammation-mediated promotion of invasion and metastasis. Cancer Metastasis Rev 2010; 29:243-248.
17. Witz I P. Tumor-microenvironment interactions: dangerous liaisons. Adv Cancer Res 2008; 100:203-229.
18. Qian B Z, Li J, Zhang H, et al. CCL2 recruits inflammatory monocytes to facilitate breast-tumour metastasis. Nature 2011; 475:222-225.
19. Tacke F, Alvarez D, Kaplan T J, et al. Monocyte subsets differentially employ CCR2, CCR5, and CX3CR1 to accumulate within atherosclerotic plaques. J Clin Invest 2007; 117:185-194.
20. Randolph G J, Inaba K, Robbiani D F, et al. Differentiation of phagocytic monocytes into lymph node dendritic cells in vivo. Immunity 1999; 11:753-761.
21. Jakubzick C, Tacke F, Ginhoux F, et al. Blood monocyte subsets differentially give rise to CD103+ and CD103− pulmonary dendritic cell populations. J Immunol 2008; 180:3019-3027.
22. Jakubzick C, Helft J, Kaplan T J, et al. Optimization of methods to study pulmonary dendritic cell migration reveals distinct capacities of DC subsets to acquire soluble versus particulate antigen. J Immunol Methods 2008; 337:121-131.
23. Randolph G J, Furie M B. A soluble gradient of endogenous monocyte chemoattractant protein-1 promotes the transendothelial migration of monocytes in vitro. J Immunol 1995; 155:3610-3618.
24. Mirzadegan T, Diehl F, Ebi B, et al. Identification of the binding site for a novel class of CCR2b chemokine receptor antagonists: binding to a common chemokine receptor motif within the helical bundle. J Biol Chem 2000; 275:25562-25571.
25. Kusmartsev S, Gabrilovich D I. Role of immature myeloid cells in mechanisms of immune evasion in cancer. Cancer Immunol Immunother 2006; 55:237-245.
26. Mantovani A, Sica A. Macrophages, innate immunity and cancer: balance, tolerance, and diversity. Curr Opin Immunol 2010, 22:231-237.

What is claimed is:

1. A pharmaceutical composition, comprising:
an agent comprising a vaccine and;
one or more angiotensin II receptor blocker (ARB) agent, wherein the one or more angiotensin II receptor blocker (ARB) agent is selected from the group consisting of Losartan, Candesartan, Eprosartan, Irbesartan, Olmesartan, Telmisartan, Azilsartan, Valsartan, or a combination thereof; and
a pharmaceutically acceptable carrier.

2. The pharmaceutical composition of claim 1, wherein the vaccine is a live whole virus, a killed whole virus, an attenuated whole virus, a killed bacteria, an attenuated bacteria, a virus-like particle, or a bacterial, viral, or parasite protein, recombinant protein, or peptide.

3. The pharmaceutical composition of claim 1, wherein the one or more angiotensin II receptor blocker (ARB) agent is Candesartan.

4. The pharmaceutical composition of claim 1, wherein the one or more angiotensin II receptor blocker (ARB) agent is Losartan.

5. The pharmaceutical composition of claim 1, further comprising one or more anti-tumor preparation, wherein the one or more anti-tumor preparation comprises a therapeutic antibody, a topoisomerase inhibitor, an antimetabolite, a platinum-based agent, an alkylating agent, a tyrosine kinase inhibitor, an Anthracycline antibiotic, an anti-angiogenic agent, or a vinca alkaloid.

6. The pharmaceutical composition of claim 5, wherein the one or more anti-tumor preparation is Sunitinib.

7. The pharmaceutical composition of claim 1, wherein the vaccine is a viral vector vaccine.

8. A pharmaceutical composition, comprising:
an agent comprising a vaccine and;
a compound of Formula (I):

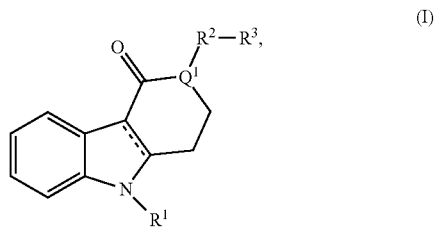

wherein:
$R^1$ is hydrogen or $C_{1-6}$ alkyl;
⸺ is a single bond or a double bond;
$Q^1$ is N or CH;
$R^2$ is selected from hydrogen and $C_{1-6}$ alkylene, wherein one carbon unit of said alkylene is optionally replaced with —O—, —S—, —SO—, SO2-, —$NR^a$—, or —CO—; wherein $R^a$ is hydrogen or $C_{1-6}$ alkyl; and
$R^3$ is hydrogen or an optionally substituted 5-membered heteroaryl ring; wherein the heteraryl ring is optionally substituted with $C_{1-6}$ alkyl;
or pharmaceutically acceptable salts thereof;
and a pharmaceutically acceptable carrier.

9. The pharmaceutical composition of claim 8, wherein the compound of Formula (I) is Ondansetron or Alosetron.

10. The pharmaceutical composition of claim 1, wherein the agent is an anti-tumor vaccine and the one or more angiotensin II receptor blocker (ARB) agent is Losartan.

11. The pharmaceutical composition of claim 8, wherein the agent is an anti-tumor vaccine and the one or more angiotensin II receptor blocker (ARB) agent is Ondansetron.

12. The pharmaceutical composition of claim 1, wherein the vaccine is a DNA vaccine.

13. The pharmaceutical composition of claim 1, wherein the vaccine is a dendritic vaccine.

* * * * *